(12) United States Patent
Slater et al.

(10) Patent No.: US 8,367,403 B2
(45) Date of Patent: Feb. 5, 2013

(54) VECTORS FOR DIRECTIONAL CLONING

(75) Inventors: Michael R. Slater, Madison, WI (US); Ethan Edward Strauss, Madison, WI (US); Keith V. Wood, Mt. Horeb, WI (US); James Robert Hartnett, Madison, WI (US)

(73) Assignee: Promega Corporation, Madison, WI (US)

(*) Notice: Subject to any disclaimer, the term of this patent is extended or adjusted under 35 U.S.C. 154(b) by 0 days.

(21) Appl. No.: 12/648,119

(22) Filed: Dec. 28, 2009

(65) Prior Publication Data

US 2010/0216231 A1    Aug. 26, 2010

Related U.S. Application Data

(63) Continuation of application No. 10/987,411, filed on Nov. 12, 2004, now abandoned, which is a continuation of application No. 10/678,961, filed on Oct. 3, 2003.

(51) Int. Cl.
*C12N 15/00* (2006.01)
*C12N 15/09* (2006.01)

(52) U.S. Cl. .................. 435/320.1; 435/69.1

(58) Field of Classification Search .......... None
See application file for complete search history.

(56) References Cited

U.S. PATENT DOCUMENTS

| | | | |
|---|---|---|---|
| 4,403,036 | A | 9/1983 | Hartley et al. |
| 4,724,202 | A | 2/1988 | Dattagupta et al. |
| 4,784,949 | A | 11/1988 | Gelfand et al. |
| 4,952,496 | A | 8/1990 | Studier et al. |
| 5,179,015 | A | 1/1993 | Wilson et al. |
| 5,200,333 | A | 4/1993 | Wilson |
| 5,320,957 | A | 6/1994 | Brooks et al. |
| 5,342,782 | A | 8/1994 | Thach |
| 5,366,882 | A | 11/1994 | Lunnen et al. |
| 5,370,957 | A | 12/1994 | Nishikiori et al. |
| 5,391,487 | A | 2/1995 | Kappelman et al. |
| 5,460,941 | A | 10/1995 | Camerini-Otero et al. |
| 5,498,535 | A | 3/1996 | Fomenkov et al. |
| 5,595,895 | A | 1/1997 | Miki et al. |
| 5,637,476 | A | 6/1997 | Van Cott |
| 5,663,067 | A | 9/1997 | Xu et al. |
| 5,693,489 | A | 12/1997 | Studier et al. |
| 5,707,811 | A | 1/1998 | Ferrin et al. |
| 5,731,411 | A | 3/1998 | Voloshin et al. |
| 5,811,093 | A | 9/1998 | Merril et al. |
| 5,830,731 | A | 11/1998 | Seed et al. |
| 5,851,808 | A | 12/1998 | Elledge et al. |
| 5,869,320 | A | 2/1999 | Studier et al. |
| 5,910,438 | A | 6/1999 | Bernard et al. |
| 6,096,523 | A | 8/2000 | Parrott et al. |
| 6,187,589 | B1 | 2/2001 | Bertling |
| 6,248,569 | B1 | 6/2001 | Dunn et al. |
| 6,800,453 | B2 | 10/2004 | Labaer et al. |
| 2001/0029027 | A1 | 10/2001 | Innerarity et al. |
| 2002/0019049 | A1 | 2/2002 | Lok |
| 2002/0106797 | A1 | 8/2002 | Miles et al. |
| 2003/0143522 | A1 | 7/2003 | Perler et al. |
| 2003/0162249 | A1 | 8/2003 | Gray et al. |
| 2004/0166567 | A1 | 8/2004 | Santi et al. |
| 2005/0048580 | A1 | 3/2005 | Labaer et al. |
| 2005/0074785 | A1 | 4/2005 | Slater et al. |
| 2005/0074883 | A1 | 4/2005 | Slater et al. |
| 2005/0130205 | A1 | 6/2005 | Slater et al. |
| 2007/0212762 | A1 | 9/2007 | Slater et al. |

FOREIGN PATENT DOCUMENTS

| | | |
|---|---|---|
| AU | 2003288189 | 6/2004 |
| DE | 19514310 | 10/1996 |
| DE | 10038573 | 2/2002 |
| EP | 0178863 | 4/1986 |
| EP | 0517111 | 12/1992 |
| EP | 437100 | 12/1995 |
| EP | 0792934 | 9/1997 |
| EP | 0931835 | 7/1999 |
| EP | 951539 | 10/1999 |
| EP | 1184462 | 3/2002 |
| RU | 2105064 | 2/1998 |
| WO | WO 91/02077 | 2/1991 |
| WO | WO 91/05866 | 5/1991 |
| WO | WO 96/01313 | 1/1996 |
| WO | WO 98/58067 | 12/1998 |
| WO | WO 00/12687 | 3/2000 |
| WO | WO 01/07633 | 2/2001 |
| WO | WO 01/21817 | 3/2001 |
| WO | WO 01/55369 | 8/2001 |
| WO | WO 02/095037 | 11/2002 |
| WO | WO 2004/050877 | 6/2004 |
| WO | WO 2005/087932 | 9/2005 |

OTHER PUBLICATIONS

United States Patent Office Action for U.S. Appl. No. 10/678,961 dated May 10, 2011 (6 pages).
United States Patent Office Action for U.S. Appl. No. 10/702,228 dated Oct. 7, 2010 (9 pages).
Japanese Patent Office Action for Application No. 2006-534051 dated Aug. 3, 2010 (8 pages) English translation.
Oldenburg, D.J. et al., "Mitochondrial DNA from the liver wort *Marchantia polymorpha*: circularly permuted linear molecules, head-to-tail concatemers, and a 5' protein," J. Mol. Biol. (2001) 310:549-582.
Zolotukhin, S. et al., "Production and purification of serotype 1, 2, and 5 recombinant adeno-associated viral vectors," Methods (2002) 28:158-167.
Japanese Patent Office Action for Application No. 2006-534051 dated Jun. 2, 2011 (10 pages).
United States Patent Office Action for U.S. Appl. No. 10/678,961 dated Oct. 28, 2010 (12 pages).
Uberlacker, B. et al., "Vectors with Rare-Cutter Restriction Enzyme Sites for Expression of Open Reading Frames in Transgenic Plants," Molecular Breeding (1996) 2:293-295.
United States Patent Office Action for U.S. Appl. No. 10/702,228 dated Jun. 15, 2011 (9 pages).
United States Patent Office Notice of Allowance for U.S. Appl. No. 10/678,961 dated Jun. 25, 2012 (6 pages).

(Continued)

*Primary Examiner* — Nancy T Vogel
(74) *Attorney, Agent, or Firm* — Michael Best & Friedrich LLP

(57) ABSTRACT

The invention provides vectors and methods for directional cloning.

7 Claims, 29 Drawing Sheets

OTHER PUBLICATIONS

United States Patent Office Supplemental Notice of Allowance for U.S. Appl. No. 10/678,961 dated Jul. 12, 2012 (2 pages).

"Belgian Coordinated Collections of Micro-organisms," BCCM/LMBP Plasmids Catalogue [online] retrieved Sep. 14, 2007, http://bccm.belspo.be/db/lmbp_plasmid_details.php?NM=pAT153 (Sep. 14, 2007) 3 pages.

"BL21-A1™ Oen Shot® chemicall competent *E. coli*," Catalog No. C6070-03 (Version B) (Oct. 7, 2002) 19 pages.

"Creator™ DNA cloning kit user manual," Protocol #PT3460-1, Version #PR 17851, 5 pages, 2001.

"Enzyme Finder by End-Biolabs," New England Biolabs catalog website, http://web.archive.org/web/20020802223809/www.neb.com/neb/frame_cat.html (3 pages).

"Gateway™ Gateway cloning technology," Instruction Manual, published by Life Technologies (Published before Oct. 2003) 59 pages.

Aebi, M. et al., "Sequence requirements for splicing of higher eukaryotic nuclear pre-mRNA," Cell (1986) 47(4):555-565.

Berg, C.M. et al., "Transposable element tools for microbial genetics," *Escherichia* and Samonellea (1996) 2:2588-2612.

Berger, S.L. et al., "Phoenix mutagenesis: one-step reassembly of multiply cleaved plasmids with mixtures of mutant and wild-type fragments," Anal. Biochem. (1993) 214:571-579.

Berger, S.L., "Gene modification with hapaxoterministic restriction enzymes—easing the way," Meth. Mol. Biol. 160:Nuclease Methods and Protocols (2001) 443-458.

Berger, S.L., "Prospective—expanding the potential of restriction endonucleases: use of hapaxoterministic enzymes," Anal. Biochem. (1994) 222:1-8.

Bilcock, D.T. et al., "Reactions of type II restriction endonucleases with 8-base pair recognition sites," J. Biol. Chem. (1999) 274(51):36379-36386.

Bolton, B.J. et al., "Ksp6321, a novel class-HS restriction endonuclease from *Kluyvera* sp. strain 632 with the asymmetric hexanucleotide recognition sequence: 5'-CTCTTC(N)1-3' 3'-GAGAAG(N)4-5," Gene (1988) 66:31-43.

Chappell, S.A. et al., "A 9nt segment of a cellular mRNA can function as an internal ribosome entry site (IRES) and when present in linked multiple copies greatly enhances IRES activity," Proc. Natl. Acad. Sci. USA (2000) 97(4):1536-1541.

Chen, M. et al., "The roles of signal peptide and mature protein in Rnase (Barnase) export from *Bacillus subtills*," Mol. Gen. genet. (1993) 239(3):409-415.

Csirik, J. et al., "A computer algorithm to determine the recognition site of restriction enzymes," Computer Applications in the Biosciences (1987) 3(3):245-246.

Dennis, J.J. et al., "Rapid generation of hested deletions by differential restriction digestion," BioTechniques (2002) 33(2):310, 312, 314-315.

Deyev, S.M. et al., "Ribonuclease-charge vector for facile direct cloning with positive selection," Mol. Gen. Genet. (1998) 379-382.

Egan, S.M. et al., "A regulatory cascade in the induction of rhaBAD," J. Mol. Biol. (1993) 234(1):87-98.

Ellrott, K.P. et al., "Restriction enzyme recognition sequence search program," BioTech. (2002) 33(6):1322-1326.

Haldimann, A. et al., "Use of new methods for construction of tightly regulated arabinose and rhamnose promoter fusions in studies of the *Escherichia coli* phosphate regulon," J. Bacter. (1998) 180(5):1277-1286.

Han, J.H. et al., "Lambda gt22S, a phage expression vector for the directional cloning of cDNA by the use of a single restriction enzyme sfil," Nucl. Acids Res. (1988) 16(24):11837.

Hartley, R.W., "Barnase and Barstar—expression of its cloned inhibitor permits expression of a cloned ribonuclease," J. Mol. Biol. (1988) 202(4):913-915.

Holt "Method: Plasmid subcloning," http://wheat.pw.usda.gov/~lazo/methods/donis/plasmid/plsmid10.html, May 20, 1990, 5 pages.

Jucovic, M. et al., "In vivo system for the detection of low level activity barnase mutants," Prot. Eng. (1995) 8(5):497-499.

Kappelman, J.R. et al., "Sgfl, a new type-II restriction endonuclease that recognizes the octanucleotide sequence 5'-GCGAT/CGC-3'," Gene (1995) 160(1):55-58.

Kasarjian, J.K. et al., "New restriction enzymes discovered from *Escherichia coli* clinical strains using a plasmid transformation method," Nucl. Acids Res. (2003) 31(5):e22 (10 pages).

Koob, M. et al., "Conferring operator specificity on restriction endonucleases," Science (1988) 241:1084-1086.

Koob, M. et al., "Cleaving yeast and *Escherichia coli* genomes at a single site," Reports (1990) 271-273.

Koob, M. et al., "RecA-AC: single-site cleavage of plasmids and chromosomes at any predetermined restriction site," Nucl. Acids. Res. (1992) 20(21):5831-5836.

Martinez-Salas, E., "Internal ribosome entry site biology and its use in expression vectors," Curr. Opin. Biotech. (1999) 10(5):458-464.

Monaco, L. et al., "An in vitro amplification approach for the expression of recombinant proteins in mammalian cells," Biotech Appl. Biochem. (1994) 20(2):157-171.

pBAD-DEST49 Gateway™ vector, Instruction manual—Catalog No. 12283-016 (Version C), published by Invitrogen Life Technologies (Aug. 13, 2002) 30 pages.

Paddon, C.J. et al., "Expression of *Bacillus amyloliquefaciens* extracellular ribonuclease (barnase) in *Escherichia coli* following an inactivating mutation," Gene (1987) 53(1):11-19.

Prior, T.I. et al., "Barnase toxin: a new chimeric toxin composed of *Pseudomonas* exotoxin A and barnase," Cell (1991) 64(5):1017-1023.

Schoenfeld, T. et al., "Simplified protocols for using RecA cleavage and protection to target restriction enzyme action," http://www.promega.com/pnotes/50/2883m2/2883m2.html (Observed Aug. 13, 2002) 7 pages.

Schoenfeld, T., "RecA cleavage and protection for genomic mapping and subcloning," http://www.promega.com/pnotes/50/2883e/2883e.html, (Observed on Aug. 13, 2002) 7 pages.

Stuckle, E.E. et al., "Statistical analysis of nucleotide sequences," Nucl. Acids Res. (1990) 18(22):6641-6647.

Stumpp, T. et al., "Ein neues, L-rhamnose-induzierbares expressionssystem fur *Escherichia coli*," Biospektrum, Spektrum Akademischer Verlag (2000) 6(1):33-36.

Szomolanyi, e. et al., "Cloning the modification methylase gene of *Bacillus spaericus* R in *Eschericia coli*," Gene (1980) 10:219-225.

Tabor, S. et al., "A bacteriophage T7 RNA polymerase/promoter system for controlled exclusive expression of specific genes," Proc. Natl. Acad. Sci. USA (1985) 82(4):1074-1078.

Vincze, T. et al., "NEBcutter: a program to cleave DNA with restriction enzymes," Nucl. Acids Res. (2003) 31(13):3688-3691.

Wilms, B. et al., "High-cell-density fermentation for production of 1-N-carbamoylase using an expression system based on the *Escherichi coli* rhaBAD promoter," Biotech. Bioend. (2001) 73(2):95-103.

Yazynin, S.A. et al., "A new phagemid vector for positive selection of recombinants based on a conditionally lethal barnase gene," FEBS Letts. (1999) 452:351-354.

Yazynin, S.A. et al., "A plasmid vector with positive selection and directional cloning based on a conditionally lethal gene," Gene (1996) 169:131-132.

Zelenetz, A.D. et al., "Directional cloning of cDNA using a selectable sfil cassette," Gene (1990) 89(1):123-127.

European Patent Office Action for Application No. 04821603.0 dated Jan. 26, 2007 (10 pages).

European Patent Office Action for Application No. 04821603.0 dated Jul. 18, 2007 (10 pages).

European Patent Office Action for Application No. 04821603.0 dated Dec. 28, 2007 (7 pages).

European Patent Office Action for Application No. 04821603.0 dated Jun. 30, 2008 (4 pages).

European Patent Office Extended Search Report for Application No. 07013756.7 dated Sep. 28, 2007 (11 pages).

European Patent Office Action for Application No. 07013756.7 dated Jun. 19, 2008 (5 pages).

European Patent Office Extended Search Report for Application No. 09011477.8 dated May 10, 2010 (6 pages).

International Preliminary Report on Patentability for Application No. PCT/US2004/031912 dated Apr. 13, 2006 (32 pages).
International Search Report and Written Opinion for Application No. PCT/US2004/031912 dated Nov. 29, 2005 (47 pages).
Invitation to Pay Additional Fees for Application No. PCT/US2004/031912 dated Sep. 22, 2005 (13 pages).
United States Patent Office Action for U.S. Appl. No. 10/678,961 dated Apr. 2, 2009 (11 pages).
United States Patent Office Action for U.S. Appl. No. 10/678,961 dated Aug. 24, 2007 (6 pages).
United States Patent Office Action for U.S. Appl. No. 10/678,961 dated Mar. 3, 2008 (9 pages).
United States Patent Office Action for U.S. Appl. No. 10/678,961 dated Mar. 8, 2007 (9 pages).
United States Patent Office Action for U.S. Appl. No. 10/678,961 dated Oct. 15, 2009 (13 pages).
United States Patent Office Action for U.S. Appl. No. 10/678,961 dated Oct. 23, 2006 (10 pages).
United States Patent Office Action for U.S. Appl. No. 10/678,961 dated Sep. 11, 2008 (11 pages).
United States Patent Office Action for U.S. Appl. No. 10/702,228 dated Jul. 22, 2008 (8 pages).
United States Patent Office Action for U.S. Appl. No. 10/702,228 dated Sep. 19, 2007 (8 pages).
United States Patent Office Action for U.S. Appl. No. 10/702,228 dated Apr. 5, 2007 (9 pages).
United States Patent Office Action for U.S. Appl. No. 10/702,228 dated Oct. 20, 2006 (8 pages).
United States Patent Office Action for U.S. Appl. No. 10/987,411 dated Jan. 7, 2009 (8 pages).
United States Patent Office Action for U.S. Appl. No. 10/987,411 dated Jun. 11, 2008 (10 pages).
United States Patent Office Action for U.S. Appl. No. 10/987,411 dated Jun. 25, 2009 (9 pages).
United States Patent Office Action for U.S. Appl. No. 11/505,650 dated Jul. 23, 2009 (9 pages).
United States Patent Office Action for U.S. Appl. No. 11/505,650 dated Mar. 9, 2010 (8 pages).
Japanese Patent Office Action for Application No. 2006-534051 dated Mar. 15, 2012 (7 pages).

TWO TYPES OF HAPAXOMERS

- INTERNAL PALINDROMIC TYPE II ENZYMES
  -e.g., Sfi I

G G C C N N N N^N G G C C  (SEQ ID NO:20)
  C C G G N^N N N N C C G G

- OUTSIDE CUTTERS (TYPE IIS)
  -e.g., Sap I

G C T C T T C N^N N N  (SEQ ID NO:16)
  C G A G A A G N N N^

FIG. 1

CAGNNN▼CTG
GTCNNN▪GAC
      ▲

FIG. 2A

GGATGNNNNNNNNN▼NNNN (SEQ ID NO:73)
CCTACNNNNNNNNNNNNN▲ (SEQ ID NO:74)
▼NNNNNNNNNNNNNCATCC (SEQ ID NO:74)
NNNN▲NNNNNNNNNGTAGG (SEQ ID NO:73)

FIG. 2B

| | Sap I (0) | Sfi I (0) | Sfi I (0+1) | Sfi (0-2) | Sgf I/Pme I | Sap I (0) | Sap I (0+1) | Sap I (0-2) |
|---|---|---|---|---|---|---|---|---|
| Hs_Fna | 56.72 | 85.93 | 96.72 | 98.91 | 97.45 | 56.72 | 84.67 | 94.82 |
| Mgc | 61.98 | 87.02 | 97.94 | 99.70 | 98.14 | 61.98 | 90.31 | 97.60 |
| E coli | 86.71 | 99.35 | 100.00 | 100.00 | 93.52 | 86.71 | 98.37 | 99.53 |
| C elegans | 65.93 | 99.46 | 99.97 | 100.00 | 98.55 | 65.93 | 90.38 | 97.19 |
| S cerevisiae | 80.02 | 99.15 | 99.98 | 100.00 | 97.17 | 80.02 | 96.68 | 99.29 |
| Arabidopsis | 70.83 | 99.56 | 100.00 | 100.00 | 97.57 | 70.83 | 93.37 | 98.63 |

FIG. 4

7+ Cutters

| Enzymes | Recognition Sequence | HsFna | MGC | Ec | Ce | Sc | At |
|---|---|---|---|---|---|---|---|
| AarI (SEQ ID NO:75) | CACCTGCNNNN^NNNN | 7142 | 5355 | | | | 1138 |
| AbeI | CC^TCA_GC not available | 7970 | 5836 | 141 | 90 | 374 | 1833 |
| AscI | GG^CGCG_CC | 515 | 336 | 152 | 10 | 13 | 26 |
| AsiSI | GCG_AT^CGC | 108 | 62 | 207 | 39 | 29 | 178 |
| BbvCI | CC^TCA_GC | 7970 | 5836 | 141 | 90 | 374 | 1833 |
| CciNI | GC^GGCC_GC | 1444 | 823 | 19 | 33 | 31 | 97 |
| CpoI | CG^GWC_CG | 1119 | 781 | 347 | | | |
| CspI | CG^GWC_CG | 1119 | 781 | 347 | | | |
| CspBI | GC^GGCC_GC not available | 1444 | 823 | 19 | 33 | 31 | 97 |
| FseI | GG_CCGG^CC | 1139 | 740 | 5 | 9 | 10 | 70 |
| MabI | A^CCWGG_T | | | | | | |
| McHAI | GC^GGCC_GC not available | 1444 | 823 | 19 | 33 | 31 | 97 |
| Mlu1106I | RGGWCCY not available | | | | | | |
| NotI | GC^GGCC_GC | 1444 | 823 | 19 | 33 | 31 | 97 |
| PacI | TTA_AT^TAA | 708 | 395 | 66 | 8 | 213 | 138 |
| Pfl27I | RG^GWC_CY not available | | | | | | |
| PpuMI | RG^GWC_CY | | | | | | |
| PpuXI | RG^GWC_CY | | | | | | |
| Psp5II | RG^GWC_CY | | | | | | |
| PspPPI | RG^GWC_CY | | | | | | |
| RsrII | CG^GWC_CG | 1119 | 781 | 347 | | | |
| Rsr2I | CG^GWC_CG | 1119 | 781 | 347 | | | |
| SanDI | GG^GWC_CC | | | | | | |
| SapI (SEQ ID NO:94) | GCTCTTCN^NNN_ | 7260 | 4785 | 584 | 1296 | 1362 | 8870 |
| SbfI | CC_TGCA^GG | 2591 | 1802 | 60 | 13 | 66 | 251 |
| SdaI | CC_TGCA^GG | 2591 | 1802 | 60 | 13 | 66 | 251 |
| SdiI (SEQ ID NO:20) | GGCCN_NNN^NGGCC not available | 2214 | 1634 | 28 | 18 | 54 | 121 |
| SexAI | A^CCWGG_T | | | | | | |
| SfiI (SEQ ID NO:77) | GGCCN_NNN^NGGCC | 2214 | 1634 | 28 | 18 | 54 | 121 |
| SgfI | GCG_AT^CGC | 108 | 62 | 207 | 39 | 29 | 178 |
| SgrAI | CR^CCGG_YG | | | | | | |
| Sse232I | CG^CCGG_CG not available | 708 | 448 | 29 | 43 | 23 | 446 |
| Sse1825I | GG^GWC_CC not available | | | | | | |
| Sse8387I | CC_TGCA^GG | 2591 | 1802 | 60 | 13 | 66 | 251 |
| Sse8647I | AG^GWC_CT not available | | | | | | |
| VpaK32I (SEQ ID NO:76 & SEQ ID NO:78) | GCTCTTCN^NNN_ not available | 7260 | 4785 | 584 | 1296 | 1362 | 8870 |

FIG. 5A

Six Cutters

| Enzymes | Recognition Sequence | HsFna | MGC | Ec | Ce | Sc | At |
|---|---|---|---|---|---|---|---|
| NruI | TCG^CGA | 830 | 607 | 1070 | 558 | 507 | 2422 |
| SplI | C^GTAC_G | 701 | 449 | 498 | 263 | 549 | 1705 |
| SnaBI | TAC^GTA | 1080 | 621 | 435 | 165 | 885 | 2164 |
| PvuI | CG_AT^CG | 842 | 512 | 1000 | 705 | 537 | 3078 |
| MluI | A^CGCG_T | 1049 | 1019 | 976 | 295 | 337 | 1824 |
| BgI | GCCN_NNN^NGGC | 8827 | 6868 | 1333 | 469 | 750 | 2576 |
| EarI | CTCTTCN^NNN | | | | | | |
| BsrGI | TGTACA | 6683 | 4551 | 442 | 760 | 1583 | 5450 |
| XmnI | GAANN^NNTTC | 8401 | 5850 | 1167 | 1652 | 2911 | 12141 |
| SalI | G^TCGA_C | 1515 | 944 | 463 | 792 | 856 | 3616 |
| BamHI | G^GATC_C | 6426 | 4305 | 438 | 1047 | 1238 | 6782 |
| KpnI | G_GTAC^C | 4098 | 2755 | 442 | 305 | 1317 | 2992 |
| EcoRI | G^AATT_C | 6536 | 4132 | 470 | 1346 | 2466 | 8244 |
| XhoI | C^TCGA_G | 3651 | 2402 | 156 | 800 | 737 | 7092 |
| EcoRV | GAT^ATC | 3789 | 2435 | 1378 | 919 | 2289 | 8419 |
| | AAA^TTT | 7484 | 5167 | 1008 | 1049 | 3843 | 8078 |
| DraI | TTT^AAA | 8455 | 6243 | 967 | 494 | 3018 | 6778 |

(SEQ ID NO:95) — BgI
(SEQ ID NO:96) — EarI
(SEQ ID NO:55) — XmnI

FIG. 5B

7+ Blunt Cutters

| Enzymes | Recognition Sequence | HsFna | MGC | Ec | Ce | Sc | At |
|---|---|---|---|---|---|---|---|
| BstRZ246I | ATTT^AAAT | 1204 | 648 | 55 | 38 | 379 | 317 |
| BstSWI | ATTT^AAAT | 1204 | 648 | 55 | 38 | 379 | 317 |
| MspSWI | ATTT^AAAT | 1204 | 648 | 55 | 38 | 379 | 317 |
| MssI | GTTT^AAAC | 297 | 173 | 71 | 9 | 152 | 490 |
| PmeI | GTTT^AAAC | 297 | 173 | 71 | 9 | 152 | 490 |
| SmiI | ATTT^AAAT | 1204 | 648 | 55 | 38 | 379 | 317 |
| SwaI | ATTT^AAAT | 1204 | 648 | 55 | 38 | 379 | 317 |
| SrfI | GCCC^GGGC | 1433 | 887 | 40 | 11 | 11 | 30 |

FIG. 5C

Sfi

- HOW TO MAKE Sfi I "ONE WAY"
  -METHYLASES
  -Bgl, NOT Sfi I SITS, IN ACCEPTOR VECTORS

G G C C N N N N^N G G C C
  C C G G N^N N N N C C G G   (SEQ ID NO:80)

G C C N N N N^N G G C
  C G G N^N N N N C C G   (SEQ ID NO:7)

-LETHAL GENES IN STUFFER FRAGMENTS

FIG. 7

REs THAT CAN MAKE Sfi I ONE-WAY

| 3' 3b OVERHANG | RESTICTION ENZYME | RECOGNITION SEQUENCE |
|---|---|---|
| CNG | FmuI | G_GNC^C |
| CNG | PssI | RG_GNC^CY |
| CWG | Psp03I | G_GWC^C |
| GNC | BthCI | G_CNG^C |
| GSC | TauI | G_CSG^C |
| NNN | AlwNI | CAG_NNN^CTG |
| NNN | BglI | GCCN_NNN^NGGC (SEQ ID NO:7) |
| NNN | BsiYI | CCNN_NNN^NNGG (SEQ ID NO:79) |
| NNN | BstAPI | GCAN_NNN^NTGC (SEQ ID NO:81) |
| NNN | DraIII | CAC_NNN^GTG |
| NNN | MwoI | GCNN_NNN^NNGC (SEQ ID NO:12) |
| NNN | PflMI | CCAN_NNN^NTGG (SEQ ID NO:14) |
| NNN | RleAI | CCCACANNNNNNNN_NNN^ (SEQ ID NO:82) |
| NNN | SfiI | GGCCN_NNN^NGGCC (SEQ ID NO:20) |

FIG. 11

Sap I

- HOW TO MAKE Sap I "ONE WAY"
  - METHYLASES
  - ORIENTATION OF SITES IN VECTOR BACKBONE
    IN DONOR VECTOR AND IN ACCEPTOR VECTOR
  - LETHAL GENES IN STUFFER FRAGMENTS
  - Ear I, NOT Sap I SITES,
    IN ACCEPTOR VECTORS

```
    G C T C T T C N^N N N
    C G A G A A G N N N N^
    ```
    (SEQ ID NO:16)

```
    C T C T T C N^N N N
    G A G A A G N N N N^
    ```
    (SEQ ID NO:4)

- KEY ADVANTAGE OF Sap I
  - ONLY THREE BASES PER EXCHANGE SITE
    LEFT IN ACCEPTOR VECTOR

FIG. 13

TWO ENZYME APPROACH

- Sgf I -
  CUTTER OF HUMAN cDNAs, TWO BASE 3' OVERHANG

G C G A T^C G C
  C G C^T A G C G

- Pme I -
  CUTTER, BLUNT END CUTTER

G T T T^A A A C
  C A A A^T T T G

N-TERMINAL Sgf I SITE CAN ALLOW
N-TERMINAL FUSION OR NO FUSION

VAAGGAGCGATCGCCATGg (SEQ ID NO:83)
--RBS--      Kozak--

VAAGGAGCGATCGCCATG (SEQ ID NO:84)
K/E/QGlyAlaIleAlaMet (SEQ ID NO:85)

FIG. 16

C-TERMINAL Pme I SITE ALLOWS TERMINATION
(+1AA) OR C-TERMINAL FUSIONS

NNNGTTTAAACN (SEQ ID NO:86)
XaaValTer

NNNGTTTATCN with EcoRV (SEQ ID NO:87)
XaaValTyr

NNNGTTTCCAN with BalI, etc. (SEQ ID NO:88)
XaaValSer

FIG. 17

N-TERMINAL Pac I--Sgf I FUSION SITE

VAAGGA(T)TAATCGCCATGg  (SEQ ID NO:89)

K/E/QGlyLeuIleAlaMet  (SEQ ID NO:90)

C-TERMINAL Pme I--Swa I FUSION SITE

NNNGTTTAAATN  (SEQ ID NO:91)

XaaValTer

FIG. 19A

N-TERMINAL Pac I--Sgf I FUSION SITE

VAAGGA(T)TAATCGCCATGg  (SEQ ID NO:89)

--RBS        Kozak--

C-TERMINAL Pme I--Swa I FUSION SITE

NNNGTTTAAATN  (SEQ ID NO:91)

XaaValTer

FIG. 19B

VECTORS FOR DIRECTIONAL CLONING

CROSS-REFERENCE TO RELATED APPLICATIONS

This application is a continuation of U.S. application Ser. No. 10/987,411, filed Nov. 12, 2004, which is a continuation of U.S. application Ser. No. 10/678,961, filed Oct. 3, 2003, each of which is incorporated herein by reference in its entirety.

BACKGROUND OF THE INVENTION

Molecular biotechnology has revolutionized the production of protein compounds of pharmacological importance. The advent of recombinant DNA technology permitted for the first time the production of proteins on a large scale in a recombinant host cell rather than by the laborious and expensive isolation of the protein from cells or tissues which may contain minute quantities of that protein. The production of proteins, including human proteins, on a large scale in a host requires the ability to express the protein of interest in a host cell, e.g., a heterologous host cell. This process typically involves isolation or cloning of the gene encoding the protein of interest followed by transfer of the coding region (open reading frame) into an expression vector which contains elements (e.g., promoters) which direct the expression of the desired protein in the host cell. The most commonly used means of transferring or subcloning a coding region into an expression vector involves the in vitro use of restriction endonucleases and DNA ligases. Restriction endonucleases are enzymes which generally recognize and cleave a specific DNA sequence in a double-strand DNA molecule. Restriction enzymes are used to excise a DNA fragment which includes a coding region of interest from the cloning vector and the excised DNA fragment is then joined using DNA ligase to a suitably cleaved vector with transcription regulatory sequences in such a manner that a functional protein can be expressed when the resulting expression vector is introduced to a cell or an in vitro transcription/translation mixture.

A problem in controlling fragment orientation in fragments generated by restriction enzymes is that many of the commonly used restriction enzymes produce termini that are rotationally equivalent, and therefore, self-ligation of DNA fragments with such termini is random with regard to fragment orientation. Hartley and Gregori (*Gene*, 13:347 (1981)) reported a technique to control fragment orientation during ligation, which required the introduction of AvaI sites flanking either end of the cloned fragment (also see Hartley and Gregori, U.S. Pat. No. 4,403,036). Since AvaI cleavage produces distinguishable ends, self-ligation of the fragment results in a strong bias toward head-to-tail orientation. This is so because head-to-head and tail-to-tail ligation results in base mismatches. The polymerized molecules were then inserted into a vector and used to transform *E. coli*.

In a similar approach, Ikeda et al. (*Gene*, 71:19 (1988)) produced head-to-tail tandem arrays of a DNA fragment encoding a human major histocompatibility antigen that was flanked by SfiI cleavage sites. SfiI produces single-strand DNA overhangs that are not rotationally equivalent. SfiI sites have also been used to produce copolymers of gene expression cassettes and selection markers, which can be used to transfect cells (Monaco et al., *Biotechnol. Appl. Biochem.*, 20:157 (1994); Asselbergs et al., *Anal. Biochem.*, 243:285 (1996)). Monaco et al. treated the copolymer with NotI to cleave the DNA at the 3' end of the selectable marker gene. In this way, transfected DNA molecules contain only one selectable marker gene per copolymer.

Class IIS restriction enzymes can generate totally asymmetric sites and complementary cohesive ends. Kim and Szybalski (*Gene*, 71:1 (1988)) introduced sites for BspMI, a class IIS restriction enzyme, at either end of cloned DNA. Self-ligation of the cloned DNA provided multimers comprising repeat units in the same orientation. Similarly, Takeshita et al. (*Gene*, 71:9 (1988)) achieved tandem gene amplification by inserting a fragment encoding human protein C into a plasmid to introduce asymmetric cohesive ends into the fragment. In this case, sites for the class IIS enzyme, BstXI, were used. The multimer was then cloned into a cosmid vector comprising a neo gene, packaged into lambda phage particles, and amplified in *E. coli*. The cosmid vectors were then introduced into Chinese hamster ovary DHFR-cells, which were treated with G418 to select for cells that expressed the neo gene. Takeshita et al. also found that cells expressed human protein C, albeit at lower levels, following transfection with unpackaged tandem ligated DNA comprising copies of the cosmid vector and the human protein C gene.

A similar approach was described by Lee et al. (*Genetic Analysis: Biomolecular Engineering*, 13:139 (1996)), who amplified target DNA as tandem multimers by cloning the target DNA into a class IIS restriction enzyme cleavage site of a vector, excising a monomeric insert with the class IIS restriction enzyme, isolating monomeric inserts, self-ligating the inserts, and cloning the multimers into a vector. According to Lee et al., such a method is useful for polymerizing short DNA fragments for the mass production of peptides.

Another approach for forcing directional ligation is to devise synthetic linkers or adapters that are used to create asymmetric cohesive ends. For example, Taylor and Hagerman (*Gene*, 53:139 (1987)) modified the Hartley-Gregori approach by attaching synthetic directional adapters to a DNA fragment in order to establish control over fragment orientation during ligation. Following polymerization, the multimers were ligated to a linearized vector suitable for *E. coli* transformation. Stahl et al. (*Gene*, 89:187 (1990)) described a similar method for polymerizing DNA fragments in a head-to-tail arrangement. Here, synthetic oligonucleotides were designed to encode an epitope-bearing peptide with 5'-protruding ends complementary to the asymmetric cleavage site of the class IIS restriction enzyme, BspMI. After polymerization, the peptide encoding fragments were inserted into the unique BspMI site cleavage site of a vector, which was used to transform *E. coli*. Clones were screened using the polymerase chain reaction, and then subcloned into prokaryotic expression vectors for production of the peptides in *E. coli*.

Nevertheless, the ability to transfer a desired coding region to a vector with transcription regulatory sequences is often limited by the availability or suitability of restriction enzyme recognition sites. Often multiple restriction enzymes must be employed for the removal of the desired coding region and the reaction conditions used for each enzyme may differ such that it is necessary to perform the excision reactions in separate steps. In addition, it may be necessary to remove a particular enzyme used in an initial restriction enzyme reaction prior to completing remaining restriction enzyme digestions. This requires a time-consuming purification of the subcloning intermediate. It also may be necessary to inactivate restriction enzymes prior to ligation.

Methods for the directional transfer of a target DNA molecule from one vector to another in vitro or in vivo without the need to rely upon restriction enzyme digestions have been described. For example, the Creator™ DNA cloning kit (Clontech Laboratories, Inc.) uses Cre-loxP site-specific recombination to catalyze the transfer of a target gene from a donor vector to an acceptor vector, which is a plasmid containing regulatory elements of the desired host expression system (see also U.S. Pat. No. 5,851,808). Cre, a 38-kDa recombinase protein from bacteriophage P1, mediates recombination between or within DNA sequences at specific locations called loxP sites (Sauer, *Biotechniques*, 16:1086 (1994); Abremski et al., *J. Biol. Chem.*, 259:1509 (1984)). These sites consist of two 13 bp inverted repeats separated by an 8 bp spacer region that provides directionality to the recombination reaction. The 8 bp spacer region in the loxP site has a defined orientation which forces the target gene to be transferred in a fixed orientation and reading frame. Donor vectors in the kit contain two loxP sites, which flank the 5' end of a multiple cloning site (MCS) and the 5' end of the open reading frame for the chloramphenicol resistance gene. Donor vectors also contain the ampicillin gene for propagation and selection in *E. coli*, and the sucrase gene from *B. subtilis* (SacB) for selection of correct recombinants. Acceptor vectors in the kit contain a single loxP site, followed by a bacterial promoter, which drives expression of the chloramphenicol marker after Cre-lox-mediated recombination. The gene of interest, once transferred, becomes linked to the specific expression elements for which the acceptor vector was designed. If the coding sequence for the gene of interest is in frame with the upstream loxP site in the donor vector, it is in frame with all peptides in the acceptor vector.

The Gateway™ Cloning System uses phage lambda-based site-specific recombination. The LR Reaction is a recombination reaction between an entry clone having mutant attL sites and a vector (a Destination Vector, pDEST™) having the corresponding mutant attR site, mediated by a cocktail of recombination proteins (λ recombination proteins Int, Xis, and the *E. coli*-encoded protein IHF), to create an expression clone. The BP Reaction is a recombination reaction between an expression clone (or an attB-flanked PCR product) and a donor vector to create an entry clone. The BP reaction permits rapid, directional cloning of PCR products synthesized with primers containing terminal 25 bp attB sites (+4 Gs). The result is an entry clone containing the PCR fragment. Similarly, DNA segments flanked by attB sites in an expression clone can be transferred to generate entry clones which can be used to move the sequence of interest to one or more destination vectors in parallel reactions to generate expression clones. The resultant 25 bp attB sites (attB1 on the left (N-terminus) and attB2 on the right (C-terminus)) created by the LR reaction are derived from the attL sites (adjacent to the gene), whereas the distal sequences are derived from the attR sites.

However, the protein encoded by Cre-loxP based expression vectors or other site-specific recombinase based vectors, e.g., the Gateway™ Cloning System, has numerous, for instance, 8 to 13, amino acid residues at the N-terminus and C-terminus of the protein, which residues are encoded by the site-specific recombination exchange sites.

Thus, what is needed is an improved method to directionally clone a nucleic acid sequence of interest.

SUMMARY OF THE INVENTION

The invention provides methods and vectors for use in directional cloning. In one embodiment, a vector comprising an open reading frame of interest (a donor vector) comprises at least two restriction enzyme recognition sites ("restriction enzyme sites", "restriction sites" or "recognition sites") flanking the open reading frame (DNA sequence of interest), wherein at least one of the flanking sites is a site for a first restriction enzyme which generates hapaxoterministic ends, e.g., a restriction enzyme with a degenerate recognition sequence or one which cleaves outside of a recognition sequence yielding single-strand ends, and other vector sequences (backbone sequences) for replication and/or maintenance of the vector in a host cell and, optionally, one or more detectable, e.g., selectable, marker genes. In one embodiment, a donor vector comprises at least two restriction enzyme sites flanking the open reading frame, wherein at least one of the flanking sites is for a first restriction enzyme which is a hapaxoterministic restriction enzyme, e.g., a restriction enzyme with a degenerate recognition sequence, which site, once cleaved, does not result in self complementary single-strand DNA overhangs or blunt ends, i.e., the ends are non-self complementary single-strand DNA overhangs. In another embodiment, the donor vector comprises at least two restriction enzyme sites flanking the open reading frame, wherein at least two of the flanking sites are for a first restriction enzyme with a hapaxomeric recognition sequence, and optionally for the same restriction enzyme, which sites, once cleaved, yield a linear DNA fragment which does not have self-complementary single-strand DNA overhangs or blunt ends. Such a vector may be employed as a source of the open reading frame to prepare a vector for expression of the linked open reading frame (a recipient or expression vector). The backbone sequences in the recipient vector are generally provided by an acceptor vector which contains transcriptional regulatory sequences and optionally sequences for the production of fusion proteins. The acceptor vector also comprises non-essential DNA sequences flanked by at least two restriction enzyme sites for a second restriction enzyme with a hapaxomeric recognition sequence, and optionally one or more detectable, e.g., selectable, marker genes. In one embodiment, the two flanking restriction enzyme sites in the acceptor vector for the second restriction enzyme are sites which, once cleaved, do not result in self complementary single-strand DNA overhangs or blunt ends but yield a linear DNA fragment having single-strand DNA overhangs that are complementary with one of the two DNA overhangs generated by the first restriction enzyme. Once the linearized DNA fragments are ligated to form a recipient vector, the recipient vector may be introduced to cells, e.g., prokaryotic cells such as *E. coli* cells, insect cells, plant cells, mammalian cells, or lysates thereof or to in vitro transcription/translation mixtures, so as to yield a transformed cell that expresses a protein encoded at least in part by the open reading frame.

In one embodiment, the invention provides a method for the directional subcloning of DNA fragments. The method includes providing a first vector comprising a first selectable marker gene and a DNA sequence of interest, which DNA sequence of interest is flanked by at least two restriction enzymes sites, wherein at least two of the flanking restriction enzyme sites are sites for a first restriction enzyme which is a hapaxoterministic restriction enzyme, and wherein digestion of the first vector with the first restriction enzyme generates a first linear DNA fragment which lacks the first selectable marker gene but comprises the DNA sequence of interest and a first pair of non-self complementary single-strand DNA overhangs. A second vector for the method is provided which includes a second selectable marker gene which is distinguishable from the first selectable marker gene and non-essential DNA sequences, optionally including a counterselectable gene, which non-essential DNA sequences are flanked by at least two restriction enzyme sites, wherein at least two of the flanking restriction enzyme sites are for a second restriction enzyme which is a hapaxoterministic restriction enzyme, wherein digestion of the second vector with the second restriction enzyme generates a second linear DNA fragment which lacks the non-essential DNA sequences but comprises the second selectable marker gene and a second pair of non-self complementary single-stranded DNA overhangs, and wherein each of the second pair of non-self complementary single-strand DNA overhang is complementary to only one of the single-strand DNA overhangs of the first pair of non-self complementary single-strand DNA overhangs and permits the oriented joining of the first linear DNA fragment to the second linear DNA fragment. The first and second vectors, the first vector and the second linear DNA fragment, or the second vector and the first linear DNA fragment are combined in a suitable buffer with one or more of the restriction enzymes which are hapaxoterministic restriction enzymes and optionally DNA ligase under conditions effective to result in digestion and optionally ligation to yield a mixture optionally comprising a third vector comprising the first and second linear DNA molecules which are joined in an oriented manner via the first and second pairs of non-self-complementary single-strand DNA overhangs. In one embodiment, ligase is added simultaneously with the one or more restriction enzymes, while in another embodiment, ligase is added subsequent to the one or more restriction enzymes. Optionally, the mixture is introduced into a host cell, and optionally the transformed host cells are selected for the expression of second selectable marker gene or against the expression of the counterselectable gene. The method may also include identifying a third vector in which the DNA sequence of interest has been transferred in an oriented manner to the second linear DNA fragment. In one embodiment, the first restriction enzyme is SfiI, SapI or an isoschizomer thereof. In one embodiment, the first restriction enzyme is SfiI or an isoschizomer thereof and the second restriction enzyme is BglI or an isoschizomer thereof. In one embodiment, the second restriction enzyme is EarI or an isoschizomer thereof. In another embodiment, the first and second restriction enzymes are the same. Optionally, the DNA sequence of interest comprises an open reading frame comprising one or more sites for the first or second restriction enzyme. In this embodiment, optionally, prior to digestion with the one or more restriction enzymes, the sites for the one or more restriction enzymes in the open reading frame are protected so as to prevent digestion, e.g., protected by methylation such as with HaeIII methylase, SapI methylase, or SfiI methylase. Alternatively, prior to methylation, the flanking sites for the first or second restriction enzyme are contacted with an oligonucleotide complementary to the flanking restriction enzyme site and RecA. In one embodiment, ligation and oriented joining yields a third vector encoding a N-terminal fusion protein which is encoded by the DNA sequence of interest and nucleic acid sequences 5' to the 3' end of the second linear DNA fragment. In another embodiment, ligation and oriented joining yields a third vector encoding a C-terminal fusion protein which is encoded by the DNA sequence of interest and nucleic acid sequences 3' to the 5' end of the second linear DNA fragment. In yet another embodiment, ligation and oriented joining yields a third vector encoding a fusion protein which is encoded by the DNA sequence of interest and nucleic acid sequences 5' and 3' to the respective 3' and 5' end of the second linear DNA fragment. In a further embodiment, ligation and oriented joining yields a third vector encoding a fusion protein which is encoded by the DNA sequence of interest and the exchange site(s) created by the oriented joining.

Thus, the invention also provides a vector system for cloning. In one embodiment the system includes a first vector comprising a selectable marker gene and a DNA sequence of interest, which DNA sequence of interest is flanked by at least two restriction enzyme sites, wherein at least two of the flanking restriction enzyme sites are for a first restriction enzyme which is a hapaxoterministic restriction enzyme, wherein digestion of the first vector with the first restriction enzyme generates a first linear DNA fragment which does not comprise the first selectable marker gene but comprises the DNA sequence of interest and a first pair of non-self complementary single-strand DNA overhangs, wherein the first restriction enzyme sites are designed such that the first linear DNA fragment can be religated directly to a second vector. The system optionally includes a second vector, which includes a second selectable marker gene which is distinguishable from the first selectable marker and non-essential DNA sequences, optionally including a counterselectable gene, which non-essential DNA sequences are flanked by at least two restriction enzyme sites, wherein two or more of the flanking restriction enzyme sites in the second vector are for a second restriction enzyme which is a hapaxoterministic restriction enzyme, wherein digestion of the second vector with the second restriction enzyme generates a second linear DNA fragment which lacks the non-essential DNA sequences but comprises the second selectable marker gene and a second pair of non-self complementary single-strand DNA overhangs, wherein each of the second pair of non-self complementary single-strand DNA overhangs is complementary to only one of the single-strand DNA overhangs of the first pair of non-self complementary single-strand DNA overhangs and permits the oriented joining of the first linear DNA fragment to the second linear DNA fragment. Further provided is a kit which includes one or more vectors of the vector system.

In one embodiment, at least one restriction enzyme site flanking the open reading frame of interest is for a restriction enzyme that recognizes an internal palindrome, e.g., a type II enzyme such as SfiI or BglI, including but not limited to restriction enzymes that generate more than two types of staggered ends (DNA overhangs) due to the ambiguity in base recognition, for instance, AhdI, AlwNI, ApaBI, BglI, BlpI, BstAPI, BstEII, BstXI, Bsu36I, DraII, DraIII, DrdI, Eam1105I, EcoNI, PflMI, PssI, SauI, SfiI, XcmI, as well as isoschizomers thereof, but not restriction enzymes that generate blunt ends. In another embodiment, at least one restriction enzyme site flanking the open reading frame of interest is for a type IIS enzyme, e.g., SapI or EarI, such as restriction enzymes that generate ends outside of their recognition sites including but not limited to AarI, AceIII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I (EarI), MboII, MlyI, MmeI, MnlI, PleI, PpiI, PsrI, RleAI, SapI, VapK32I, SfaNI, SspD5I, Sth132I, StsI, TaqII, TspDTI, TspGWI, TspRI, Tth111II, as well as isoschizomers thereof. In one embodiment, the open reading frame encodes one or more domains of one or more proteins.

In another embodiment, the invention provides a donor vector comprising an open reading frame of interest flanked by at least two restriction enzyme sites, one of which flanking sites is for a first restriction enzyme that has a low frequency, e.g., fewer than about 25%, for instance, including fewer than about 20%, 10%, 5% or even fewer, e.g., about 1%, of recognition sites in a plurality of, for instance, 3 or more, including 100, 1,000, 10,000 or more, cDNAs or open reading frames for a particular species (an "infrequent cutter") and generates single-strand DNA overhangs, and the other of which flanking sites is for a second restriction enzyme that has a low frequency of recognition sites in a plurality of cDNAs or open reading frames for a particular species, for instance, the same species as for the first restriction enzyme, and generates ends that are not complementary to the overhangs generated by the first restriction enzyme. In one embodiment, the second restriction enzyme generates blunt ends (a "blunt cutter"). The frequency of a particular restriction enzyme recognition site in one or more nucleic acid molecules can be determined by methods well-known to the art. For instance, databases with a plurality of cDNA sequences or open reading frames for a particular organism may be employed to determine such a frequency. A donor vector of the invention may be employed as a source of the open reading frame of interest to prepare a recipient vector of the invention. The backbone sequences in the recipient vector are generally provided by an acceptor vector having transcriptional regulatory sequences of interest and optionally sequences for the production of fusion proteins. The acceptor vector also comprises non-essential DNA sequences flanked by at least two restriction enzyme sites, and one or more detectable marker genes. In one embodiment, one of the flanking sites in the acceptor vector is for a third restriction enzyme which generates single-strand DNA overhangs, which single-strand DNA overhangs are complementary with the single-strand DNA overhangs produced when the donor vector is digested with the first restriction enzyme. The other flanking site in the acceptor vector is for a fourth restriction enzyme which generates ends that are not complementary to the ends generated by the first or third restriction enzyme but are compatible, i.e., can be ligated to, with ends generated by the second restriction enzyme. In one embodiment, the second and fourth recognition enzymes are blunt cutters and the restriction sites for the second and fourth restriction enzymes are not recognized by the same restriction enzyme. In one embodiment, at least one restriction enzyme site flanking the open reading frame of interest is for one of SgfI, PvuI or PacI, restriction enzymes which generate ends compatible with SgfI, e.g., SgfI, PvuI, BstKTI or PacI, or restriction enzymes that yield ends that can be selected to have the proper 3' TA overhang, e.g., AasI, Bce83I, BsiEI, BcgI, BpmI, BpuEI, BseMI, Bse3DI, BseMII, BseRI, BsgI, BspCNI, BsrDI, BstF5I, BseGI, BtsI, DrdI, DseDI, EciI, Eco57MI, Eco57I, Bce83I, GsuI, MmeI, TspDTI, Tth111II, BspKT5I, AcuI, BspKT61, Eco57MI, TaqII, TspGWI, or isoschizomers thereof. In one embodiment, at least one restriction enzyme site flanking the open reading frame of interest is for one of SgfI (AsiSI), PacI, or PvuI (Afa22MI, Afa16RI, BspCI, EagBI, ErhB9I, MvrI, NblI, Ple19I, Psu161I, RshI, XorII).

In another embodiment, at least one restriction enzyme site flanking the open reading frame of interest is for PmeI (MssI), DraI, AhaIII (DraI, PauAII, SruI), NruI (Bsp68I, MluB2I, Sbo13I, SpoI), SnaBI (BstSNI, Eco105I), SrfI, or SwaI (BstRZ246I, BstSWI, MspSWI, SmiI). In another embodiment, at least one restriction enzyme site flanking the open reading frame of interest is for a restriction enzyme that generates a blunt end which can create a stop codon after ligation with another blunt end, for instance, one that can create a stop codon after ligation with an end generated by PmeI, e.g., EcaBC3I (TC^GA), SciI (CTC^GAG), HindIII (GTC^GAC, a version of GTYRAC), HpaI (GTT^AAC), HindIII (GTT^AAC, a version of GTYRAC), DraI (TTT^AAA), SwaI (ATTT^AAAT), or an isoschizomer thereof, or for a restriction enzyme that yields ends that can be selected to have a blunt end such as 5'GA, 5'AG or 5'AA, e.g., BsaBI, Cac8I, Hpy8I, MlyI, PshAI, SspD5I, or an isoschizomer thereof. For example, ligation of ends generated by PmeI and DraI can create a stop site, as would ligation of NTT and GAN, NCT and AGN, or NTT and AAN, wherein each N is A, T, G or C. In one embodiment, the exchange site formed from blunt end ligation of an end generated by PmeI and that of another blunt cutter can yield a coding sequence for a protein fusion. For instance, ligation of an open reading frame terminating in an end generated by PmeI and an end generated by BalI, BfrBI, BsaAI, BsaBI, BsrBI, BtrI, Cac8I, CdiI, CviJI, CviRI, Eco47III, Eco78I, EcoICRI, EcoRV, FnuDII, FspAI, HaeI, HaeIII, Hpy8I, LpnI, MlyI, MslI, MstI, NaeI, NlaIV, NruI, NspBII, OliI, PmaCI, PmeI, PshAI, PsiI, PvuII, RsaI, ScaI, SmaI, SnaBI, SrfI, SspI, SspD5I, StuI, XcaI, XmnI, ZraI, or an isoschizomer thereof, can extend the open reading frame at the 3' end.

In one embodiment, the invention provides a method to directionally clone a DNA sequence of interest which employs a recipient vector comprising a DNA sequence of interest, e.g., optionally encoding a fusion protein, flanked by at least two restriction enzyme sites, one of which is for a first restriction enzyme that has a low frequency of recognition sites in a plurality of cDNAs or open reading frames for a particular species and generates single-strand DNA overhangs, and the other of which flanking sites is for a second restriction enzyme that has a low frequency of recognition sites in a plurality of cDNAs or open reading frames for a particular species and generates blunt ends. An acceptor vector may comprise a counter-selectable marker flanked by at least two restriction enzymes sites. One of the flanking sites in the acceptor vector is for a third restriction enzyme which generates single-strand DNA overhangs which are complementary with the single-strand DNA overhangs produced when the recipient vector is digested with the first restriction enzyme. The other flanking site in the acceptor vector is for a fourth restriction enzyme which generates blunt ends. The method includes contacting the recipient vector with the first and second restriction enzymes and the acceptor vector with the third and fourth restriction enzymes, ligating the resulting linear molecules, transforming a host cell with the ligation mixture, and selecting for host cells with desirable recombinant molecules, i.e., vectors with the DNA sequence of interest and the acceptor vector backbone, e.g., vectors which lack the counter-selectable gene, and optionally include a selectable marker present on the acceptor vector backbone. In one embodiment, the first and third restriction enzymes are the same. In one embodiment, the second and fourth restriction enzymes are the same. In this manner, DNA sequences of interest may be moved from one expression vector to another, for instance, to express a fusion protein encoded by a fusion of acceptor vector sequences, the exchange site(s), and the DNA sequence of interest.

The methods of the invention thus employ one or more restriction enzymes that generate unique ends and optionally ligase to clone an open reading frame of interest. Vectors with one or more restriction enzyme sites for restriction enzymes that provide unique ends are particularly useful in directional cloning and ordered gene assembly. Moreover, the use of the vectors and methods of the invention is easy, inexpensive, fast, automatable, and results in high fidelity. Further, the vectors may be designed to express fusion proteins with no or one to a few, e.g., less than 7, amino acid residues fused to the N-terminus, C-terminus, or both the N- and C-termini. For instance, fusions generated with SfiI sites flanking the DNA sequence of interest may yield fusion proteins with 4 amino acid residues at the N-terminus and C-terminus, while fusions generated with SgfI/PmeI or SapI sites flanking the DNA sequence of interest may yield fusion proteins with a single amino acid residue only at the C-terminus. If SfiI or PmeI sites are added to a DNA sequence of interest, e.g., using an amplification reaction, an additional 3-5 bp flanking the recognition site may be included to increase cleavage efficiency. Moreover, N- and/or C-terminal fusions with fusion partner sequences useful in purification, e.g., immobilization, solubilization, in situ detection, protein domain studies, and protein-protein interactions, e.g., in vitro or in vivo, may be prepared, wherein fusion partner sequences are encoded by acceptor vector sequences and/or exchange sites.

Also provided is a recombinant host cell useful to reduce unintended expression from a vector. In one embodiment, the host cell is deficient in one or more inducible genes, for instance, the host cell does not express one or more rhamnose catalytic genes, e.g., the host cell is rhaBAD$^-$, and comprises an expression vector, e.g., one which is stably introduced to the host cell. The expression vector comprises an inducible promoter for the one or more genes, which promoter has a low level of uninduced expression and preferably has a relatively slow induction profile but high final levels of expression, e.g., a rhaBAD promoter, and which promoter is operably linked to an open reading frame, such as one for a heterologous (non-native) transcription regulatory gene product, e.g., a RNA polymerase. In one embodiment, the recombinant host cell is deficient in rhamnose catabolism, and has a recombinant DNA molecule comprising a rhamnose-inducible promoter operably linked to an open reading frame for a heterologous RNA polymerase. In one embodiment, the host cell is a prokaryotic cell, for instance, an E. coli cell. In one embodiment, the heterologous RNA polymerase is a phage RNA polymerase, such as a T7 RNA polymerase. The recombinant host cell may be contacted with an expression vector comprising a promoter for the heterologous RNA polymerase and an open reading frame of interest, and rhamnose, e.g., either simultaneously or sequentially. In one embodiment, the expression vector comprises a transcription terminator sequence, e.g., rrnB, and a promoter 5' to the open reading frame of interest, which promoter is upregulated by the heterologous transcription regulatory gene product, as well as restriction sites for one or more infrequent cutters flanking the open reading frame, and optionally, in the vector backbone, a selectable marker gene, a sequence which specifies a high vector copy number, and a sequence which reduces vector multimerization, e.g., cer. An expression vector comprising a promoter such as one for a heterologous transcription regulatory gene product, such as a RNA polymerase, which promoter is operably linked to an open reading frame of interest, may also be employed in an in vitro transcription/translation system.

Further provided is an isolated nucleic acid fragment encoding barnase which lacks a secretory domain (signal), a vector comprising the nucleic acid fragment, such as one which comprises a promoter, for instance, a $\lambda P_L$ promoter linked to the nucleic acid fragment, isolated protein encoded by the nucleic acid fragment, and a host cell comprising the vector. Optionally, the host cell expresses barstar. In one embodiment, the host cell expresses barstar from a promoter which is constitutively expressed in prokaryotic cells. Optionally, the host cell is an E. coli cell. In one embodiment, an open reading frame for barstar is expressed from a 4c promoter. In one embodiment, the vector system of the invention includes a second vector comprising a counterselectable gene comprising a nucleic acid fragment encoding a barnase which lacks a secretory domain.

Also provided is a vector comprising an open reading frame 3' to a DNA fragment of no more than 30 base pairs. The DNA fragment comprises a ribosome binding site, a SgfI recognition site, and a sequence which, when present in mRNA, enhances the binding of the mRNA to the small subunit of a eukaryotic ribosome. In one embodiment, the DNA fragment includes AAGGAGCGATCGCCATGX (SEQ ID NO:1), and wherein X is A, T, G or C.

Further provided is a vector comprising a SgfI recognition site, a sequence which comprises ATG and which sequence, when present in mRNA, enhances the binding of the mRNA to the small subunit of a eukaryotic ribosome, and an open reading frame which begins at the ATG in the sequence.

The invention includes a vector comprising a SgfI recognition site 5' to a recognition site for a first restriction enzyme which has infrequent restriction sites in cDNAs or open reading frames from at least one species and generates blunt ends, which vector, once digested with SgfI and the first restriction enzyme and ligated to a DNA fragment comprising an open reading frame flanked by an end generated by a second restriction enzyme that generates a 3' TA overhang and an end generated by a third restriction enzyme that generates blunt ends, yields a recombinant vector comprising the open reading frame. In one embodiment, the first and third restriction enzymes are the same. In another embodiment, the second restriction enzyme is SgfI.

Also provided is a vector comprising a first open reading frame which includes a SgfI recognition site and a recognition site which is not in the open reading frame for a restriction enzyme that has infrequent restriction sites in cDNAs or open reading frames from at least one species and generates blunt ends. The vector, once digested with SgfI and the restriction enzyme which has infrequent restriction sites in cDNAs or open reading frames from at least one species and generates blunt ends, and ligated to a DNA fragment comprising a second open reading flanked by a single-strand 3' TA DNA overhang and a blunt end, yields a recombinant vector comprising a third open reading frame comprising the first and second open reading frames, which third open reading frame encodes a fusion peptide or protein.

The invention also includes a vector comprising a ribosome binding site which optionally overlaps by one nucleotide with a SgfI recognition site and a recognition site which is not in the open reading frame for a restriction enzyme that has infrequent restriction sites in cDNAs or open reading frames from at least one species and generates blunt ends. The vector, once digested with SgfI and the restriction enzyme that has infrequent restriction sites in cDNAs or open reading frames from at least one species and generates blunt ends, and ligated to a DNA fragment comprising an open reading frame encoding a peptide or polypeptide flanked by

```
5'  CGCCATGX₁Y₁        (SEQ. ID No: 2)

3'  TAGCGGTACX₂Y₂      (SEQ. ID No: 71)
``` and a blunt end, yields a recombinant vector which encodes the peptide or polypeptide, wherein $X_1$ is the first codon which is 3' to the start codon for the open reading frame, wherein $X_2$ is the complement of $X_1$, wherein $Y_1$ is the remainder of the open reading frame, and wherein $Y_2$ is the complement of $Y_1$.

Further provided is a vector comprising a first open reading frame which includes a PmeI recognition site and is flanked at the 5' end by a recognition site for a first restriction enzyme that generates complementary single-strand DNA overhangs, which vector, once digested with PmeI and the first restriction enzyme, and ligated to a DNA fragment comprising a blunt end at the 5' end of a second open reading frame and an end generated by a second restriction enzyme which generates single-strand DNA overhangs which are complementary to the single-strand DNA overhangs generated by the first restriction enzyme, yields a recombinant vector comprising a third open reading frame comprising the first and second open reading frames.

The invention further includes a vector comprising a first open reading frame which includes a PmeI recognition site and is flanked at the 5' end by site for a first restriction enzyme that generates complementary single-strand DNA overhangs. The vector, once digested with PmeI and the first restriction enzyme, and ligated to a DNA fragment comprising a blunt end and an end generated by a second restriction enzyme which generates single-strand DNA overhangs which are complementary to the single-strand DNA overhangs generated by the first restriction enzyme, yields a recombinant vector which includes $N_1N_2N_3GTTTN_4N_5$, wherein $N_1N_2N_3GTTT$ is a sequence from the 3' end of the digested expression vector. In one embodiment, the triplet $N_1N_2N_3$ does not code for a stop codon, and $N_4$ and $N_5$=A, or $N_4$=A and $N_5$=G or $N_4$=G and $N_5$=A. In another embodiment, the triplet $N_1N_2N_3$ codes for a stop codon.

The vectors of the invention and methods of the invention which employ the vectors, are particularly useful in directional cloning of open reading frames. However, the vectors and methods of the invention are useful in other applications, for example, they may be employed to prepare probes, e.g., radioactive or nonradioactive probes, for instance, using vectors with promoters specific for a polymerase, such as bacteriophage polymerases, to prepare single-strand sense or antisense probes or therapeutic antisense RNA; or to insert a gene in an antisense orientation such that it is not expressed or expressed only after structural rearrangement (conditional gene inactivation), e.g., via recombination with Cre/lox (U.S. Pat. No. 5,658,772), FLP/FRT, the Gin recombinase of Mu, the Pin recombinase of E. coli, and the R/RS system of the pSR1 plasmid.

Also provided is a method for performing genetic analysis. The method comprises populating a database of genetic data with genetic data to create a plurality of genetic records. The database containing genetic data is queried to identify a first subset of genetic records, wherein each record has at least one recognition site for restriction enzymes included in a set of predetermined restriction enzymes, and a set of statistics associated with the restriction enzyme recognition sites for at least a second subset of genetic records in the first subset is determined.

Further provided is a computer-readable medium having computer executable instructions for performing a method for performing genetic analysis. The medium includes populating a database of genetic data with a plurality of genetic records, querying the database of genetic data to identify a first subset of genetic records, wherein each record has at least one recognition site for one predetermined restriction enzyme or for restriction enzymes included in a set of predetermined restriction enzymes, and determining a set of statistics associated with the restriction enzyme recognition sites for at least a second subset of genetic records in the first subset. Also provided is a computerized system for genetic analysis. The system includes a database of genetic data, a processor, a set of one or more programs executed by the processor causing the processor to query the database of genetic data to identify a first subset of genetic records, wherein each record has at least one recognition site for one predetermined restriction enzyme or for restriction enzymes included in a set of predetermined restriction enzymes, and determine a set of statistics associated with the restriction enzyme recognition sites for at least a second subset of genetic records in the first subset. In one embodiment, the set of statistics includes, e.g., includes determining, a number of genetic records including recognition sites for one predetermined restriction enzyme or for each of the predetermined restriction enzymes in the set. In one embodiment, the set of statistics includes, e.g., includes determining, a number of occurrences of at least one site for the one predetermined restriction enzyme or for the predetermined restriction enzymes in a genetic record in the second subset. In one embodiment, the genetic records comprise nucleic acid sequences. In one embodiment, the method further comprises filtering, or a processor is further operable to filter, the subset of genetic records to include or exclude genetic records having one or more selected characteristics. In another embodiment, the method further comprises filtering, or a processor is further operable to filter, the subset of genetic records to exclude genetic records having a size greater than a predetermined value. In one embodiment, the predetermined value is 21000 characters. In another embodiment, the method further comprises determining, or a processor is further operable to determine, a sequence of specific bases which are present as ambiguous bases within a recognition site or which are present between a recognition site for a restriction enzyme and the position at which the restriction enzyme cleaves DNA containing the recognition site.

BRIEF DESCRIPTION OF THE FIGURES

FIG. 1. Exemplary hapaxomers. (SEQ. ID Nos:16 and 20)

FIGS. 2A-B. Examples of hapaxomers with 3' or 5' overhangs. A) The symmetry of the site recognized by AlwNI, a restriction enzyme that cleaves an interrupted palindrome within the recognition site. If the bases denoted "N" are ignored, the site is symmetrically equivalent to a PvuII site. Arrows indicate the cleavage sites on both strands. Note that a recognition and cleavage site on only one strand must be stipulated owing to the existence of a two-fold axis of symmetry. However, because cleavage by AlwNI results in DNA with overhangs consisting of three bases with four possibilities for each unspecified base, the sequence at the termini will be different depending on the strand. B) The FokI recognition and cleavage sites illustrated in both orientation (SEQ ID NOs: 73-74). Because the site lacks symmetry, there are two ways to write the bases from 5' to 3'. The cleavage sites on both strands, indicated by arrows, must be specified in order to indicate where cutting will occur. Because the cleavage sites are outside the recognition site, the single-stranded overhangs can be any set of four bases. Note that AlwNI generates 3' overhangs, whereas FokI generates 5' overhangs.

FIG. 4. Comparison of the percent of sequences in various organisms which lack (0), have no or one (0-1), or no, one or two (0-2) recognition sites for SapI, SfiI or SgfI/PmeI.

FIG. 5. Site frequencies of selected restriction enzymes in six species (SEQ ID NOs: 20, 55, 75-78, and 94-96).

FIG. 7. Directional cloning using SfiI (SEQ ID NOs: 7 and 80).

FIG. 11. Restriction endonucleases useful for directional cloning with SfiI or other restriction enzymes generating 3 base 3' overhangs (SEQ ID NOs: 7, 12, 14, 20, 79, and 81-82).

FIG. 13. Directional cloning using SapI (SEQ ID NOs: 4 and 16).

FIG. 16. Use of SgfI to generate N-terminal fusions or no fusions at the N-terminus (SEQ ID NOs: 83-85, e.g. SEQ ID NO: 69). For SEQ ID NO. 85, Xaa is Lys, Glu or Gln.

FIG. 17. Use of PmeI to generate C-terminal fusions including fusions with a single amino acid (SEQ ID NOs: 86-88, e.g. SEQ ID NO: 72). For SEQ ID NO. 72 $n_1$-$n_3$ and $Tn_4n_5$ are codons that do not code for a stop codon.

FIGS. 19A-B. N-terminal PacI-SgfI fusion site (SEQ ID NOs: 89-90) and C-terminal PmeI-SwaI fusion site (SEQ ID NO: 91). For SEQ ID NO. 90, Xaa is Lys, Glu or Gln.

DETAILED DESCRIPTION OF THE INVENTION

Definitions

Figure 3:
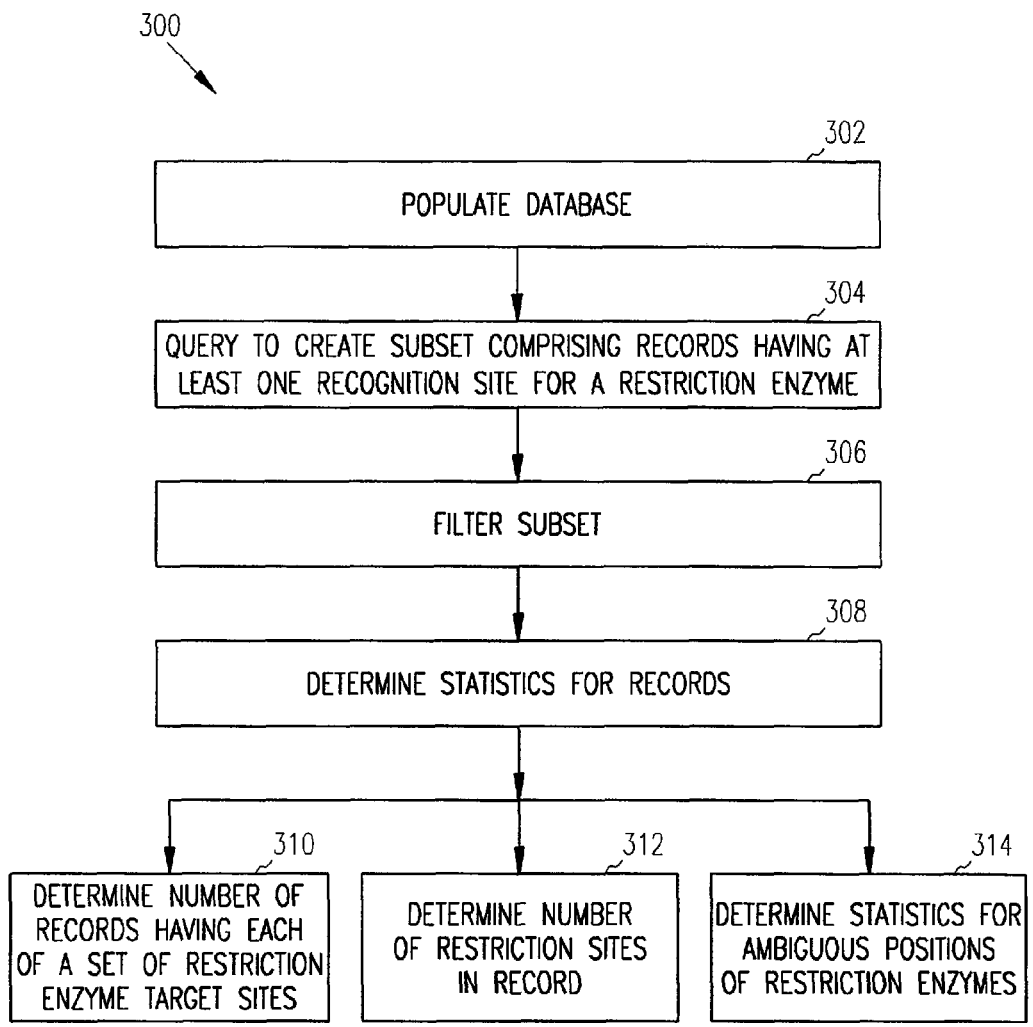
FIG. 3. A flowchart to identify restriction enzymes that have infrequent recognition sites in the genome of a particular organism.

The term "unique restriction enzyme site" indicates that the recognition sequence for a given restriction enzyme appears once within a nucleic acid molecule.

The terms "polylinker" or "multiple cloning site" refer to a cluster of restriction enzyme sites on a nucleic acid construct which are utilized for the insertion and/or excision of nucleic acid sequences such as the coding region of a gene, lox sites, etc.

The term "prokaryotic termination sequence" refers to a nucleic acid sequence which is recognized by the RNA polymerase of a prokaryotic host cell and results in the termination of transcription. Prokaryotic termination sequences commonly comprise a GC-rich region that has a twofold symmetry followed by an AT-rich sequence. Commonly used prokaryotic termination sequences are the T7 and rrnB termination sequences. A variety of termination sequences are known to the art and may be employed in the nucleic acid constructs of the present invention including, the $T_{INT}$, $T_{L1}$, $T_{L2}$, $T_{L3}$, $T_{R1}$, $T_{R2}$, $T_{6S}$ termination signals derived from the bacteriophage lambda and termination signals derived from bacterial genes such as the trp gene of E. coli.

The term "eukaryotic polyadenylation sequence" (also referred to as a "poly A site" or "poly A sequence") as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook et al., *Molecular Cloning: A Laboratory Manual*, Cold Spring Harbor (1989)); numerous vectors contain the SV40 poly A signal. Another commonly used heterologous poly A signal is derived from the bovine growth hormone (BGH) gene; the BGH poly A signal is available on a number of commercially available vectors. The poly A signal from the herpes simplex virus thymidine kinase (HSV tk) gene is also used as a poly A signal on expression vectors.

As used herein, the terms "selectable marker" or "selectable marker gene" refers to the use of a gene which encodes an enzymatic activity that confers the ability to grow in medium lacking what would otherwise be an essential nutrient (e.g., the TRP1 gene in yeast cells); in addition, a selectable marker may confer resistance to an antibiotic or drug upon the cell in which the selectable marker is expressed. A selectable marker may be used to confer a particular phenotype upon a host cell. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers.

As used herein, the term "vector" is used in reference to nucleic acid molecules that transfer DNA segment(s) from one cell to another. The term "vehicle" is sometimes used interchangeably with "vector." A "vector" is a type of "nucleic acid construct." The term "nucleic acid construct" includes circular nucleic acid constructs such as plasmid constructs, plasmid constructs, cosmid vectors, etc. as well as linear nucleic acid constructs (e.g., lambda, phage constructs, PCR products). The nucleic acid construct may comprise expression signals such as a promoter and/or an enhancer (in such a case it is referred to as an expression vector).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in procaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "transformation" and "transfection" as used herein refer to the introduction of foreign DNA into prokaryotic or eucaryotic cells. Transformation of prokaryotic cells may be accomplished by a variety of means known to the art including the treatment of host cells with $CaCl_2$ to make competent cells, electroporation, etc. Transfection of eukaryotic cells may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

As used herein, "recognition site" refers to a sequence of specific bases that is recognized by a restriction enzyme if the sequence is present in double-stranded DNA; or, if the sequence is present in single-stranded RNA, the sequence of specific bases that would be recognized by a restriction enzyme if the RNA was reverse transcribed into cDNA and the cDNA employed as a template with a DNA polymerase to generate a double-stranded DNA; or, if the sequence is present in single-stranded DNA, the sequence of specific bases that would be recognized by a restriction enzyme if the single-stranded DNA was employed as a template with a DNA polymerase to generate a double-stranded DNA; or, if the sequence is present in double-stranded RNA, the sequence of specific bases that would be recognized by a restriction enzyme if either strand of RNA was reverse transcribed into cDNA and the cDNA employed as a template with a DNA polymerase to generate a double-stranded DNA.

An "open reading frame" includes at least 3 consecutive codons which are not stop codons.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5° phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals and the like.

Transcriptional control signals in eukaryotes comprise "promoter" and "enhancer" elements. Promoters and enhancers consist of short arrays of DNA sequences that interact specifically with cellular proteins involved in transcription (Maniatis et al., *Science,* 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss et al., *Trends Biochem. Sci.,* 11:287 (1986) and Maniatis et al., supra (1987)). For example, the SV40 early gene enhancer is very active in a wide variety of cell types from many mammalian species and has been widely used for the expression of proteins in mammalian cells (Dijkema et al., *EMBO J.,* 4:761 (1985)). Two other examples of promoter/enhancer elements active in a broad range of mammalian cell types are those from the human elongation factor 1.0 gene (Uetsuki et al., *J. Biol. Chem.,* 264:5791 (1989), Kim et al., *Gene,* 91:217 (1990) and Mizushima et al., *Nuc. Acids. Res.,* 18:5322 (1990)) and the long terminal repeats of the Rous sarcoma virus (Gorman et al., *Proc. Natl. Acad. Sci. USA,* 79:6777 (1982)) and the human cytomegalovirus (Boshart et al., *Cell,* 41:521 (1985)).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York (1989) pp. 16.7-16.8). A commonly used splice donor and acceptor site is the splice junction from the 16S RNA of SV40.

Efficient expression of recombinant DNA sequences in eucaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene.

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (about 100 copies/cell).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a gene, e.g., a structural gene, and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences; these sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "purified" or "to purify" refers to the removal of contaminants from a sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from two or more amino acid residues to the entire amino acid sequence minus one amino acid.

As used herein, the term "fusion protein" refers to a chimeric protein containing the protein of interest joined to a different peptide or protein fragment. The fusion partner may, for example, enhance the solubility of a linked protein of interest, may provide an epitope tag or affinity domain to allow identification and/or purification of the recombinant fusion protein, e.g., from a host cell which expresses the fusion or a culture supernatant of that cell, or both, or may have another property or activity, e.g., two functional enzymes can be fused to produce a single protein with multiple enzymatic activities. If desired, the fusion protein may be removed from the protein of interest by a variety of enzymatic or chemical means known to the art. Thus, examples of fusion protein producing sequences useful in the vectors of the invention include epitope tag encoding sequences, affinity domain encoding sequences, or other functional protein encoding sequences, and the like. The use of the term "functional protein encoding sequence", as used herein, indicates that the fusion protein producing element of a vector encodes a protein or peptide having a particular activity, such as an enzymatic activity, e.g., luciferase or dehalogenase, a binding activity, and the like, e.g., thioredoxin. For example, a functional protein encoding sequence may encode a kinase catalytic domain (Hanks and Hunter, *FASEB J*, 9:576-595, 1995), producing a fusion protein that can enzymatically add phosphate moieties to particular amino acids, or may encode a Src Homology 2 (SH2) domain (Sadowski, et al., *Mol. Cell. Bio.*, 6:4396, 1986; Mayer and Baltimore, *Trends Cell. Biol.*, 3:8, 1993), producing a fusion protein that specifically binds to phosphorylated tyrosines.

I. Restriction Enzyme Sites and Enzymes Useful in the Vectors and Methods of the Invention The present invention employs two general approaches to directional cloning and ordered gene assembly. In one approach, restriction sites for hapaxoterministic restriction enzymes, e.g., those with degenerate recognition or cleavage sequences (see FIGS. 1-2), are employed. Hapaxoterministic enzymes are enzymes able to generate unique ends (Table 1). FokI, a type IIS enzyme, is included and so is AlwNI, an interrupted palindrome. Because the cleavage site is located among the unspecified bases, the termini are expressed in N's. Unless the complete nucleotide sequence within the interruption or flanking the recognition site is written, the detailed nature of the ends cannot be stated; statistically speaking, all single stranded overhangs will be different. It is also unlikely that these overhangs possess elements of symmetry. In the general case, this means that the protruding bases are not composed of an asymmetric unit followed by its reverse complement; the ends will not be self-complementary; and it will not be possible to form concatamers with a fragment bearing such ends. With nonhapaxoterministic enzymes such as EcoRI the opposite situation prevails; both the recognition site, G↓AATTC, and the overhanging ends produced by cleavage, AATT, always display palindrome-like elements; and the overhang of any fragment is complementary with itself and with the protruding ends of all other fragments generated by the same enzyme.

TABLE 1

```
Alw NI     ↓              Dra       ↓
    CAGNNNCTG             III   CACNNNGTG
    GTCNNNGAC                   GTGNNNCAC
         ↑                           ↑

Bbs I      ↓              Ear       ↓
    GAAGACNN              I     CTCTTCN
    CTTCTGNNNNNN                GAGAAGNNNN
              ↑                         ↑
    (SEQ ID NO: 3)              (SEQ ID NO: 4)

Bbv I      ↓              Esp3      ↓
    GCAGCNNNNNNNN         I     CGTCTCN
    CGTCGNNNNNNNNNNNN           GCAGAGNNNN
                   ↑                      ↑
    (SEQ ID NO: 5)              (SEQ ID NO: 6)

Bgl I      ↓              Fok       ↓
    GCCNNNNNGGC           I     GGATGNNNNNNNNN
    CGGNNNNNCCG                 CCTACNNNNNNNNNNNNN
         ↑                                      ↑
    (SEQ ID NO: 7)              (SEQ ID NO: 8)

Bsa I      ↓              Hga       ↓
    GGTCTCN               I     GACGCNNNNN
    CCAGAGNNNNN                 CTGCGNNNNNNNNN
              ↑                              ↑
    (SEQ ID NO: 9)              (SEQ ID NO: 10)

Bsl I      ↓              Mwo       ↓
    CCNNNNNNNGG           I     GCNNNNNNNGC
    GGNNNNNNNCC                 CGNNNNNNNCG
             ↑                             ↑
    (SEQ ID NO: 11)             (SEQ ID NO: 12)

Bsm AI     ↓              Pfl       ↓
    GTCTCN                MI    CCANNNNNTGG
    CAGAGNNNNN                  GGTNNNNNACC
             ↑                            ↑
    (SEQ ID NO: 13)             (SEQ ID NO: 14)

Bsm FI     ↓              Sap       ↓
    GTCCCNNNNNNNNNN       I     GCTCTTCN
    CAGGGNNNNNNNNNNNNNN         CGAGAAGNNNN
                     ↑                      ↑
    (SEQ ID NO: 15)             (SEQ ID NO: 16)

Bsp MI     ↓              Sfa       ↓
    ACCTGNNNN             NI    GCATCNNNNN
    TGGACGNNNNNNNN              CGTAGNNNNNNNNN
                 ↑                          ↑
    (SEQ ID NO: 17)             (SEQ ID NO: 18)
```

TABLE 1-continued

```
Bst XI     ↓              Sfi       ↓
    CCANNNNNNTGG          I     GGCCNNNNNGGCC
    GGTNNNNNNACC                CCGGNNNNNCCGG
         ↑                           ↑
    (SEQ ID NO: 19)             (SEQ ID NO: 20)
```

Note.
The cleavage sites are indicated by the arrows. Isoschizomers occur in several cases. The enzymes listed and their isoschizomers are as follows: BbsI, Bsc91I; BbvI, BstI, Bst71I; BsaI, Eco31I, BsmAI, Alw26I; EarI, Ksp632I; and PflMI, AccB7I.

Enzymes which generate blunt ends can never be hapaxoterministic. For instance, the restriction site for BsaBI has N's but the enzyme produces blunt end.

There are enzymes that are formally, but not functionally, hapaxomers. In this category are restriction endonucleases that generate overhangs of only one or two unspecified bases such as AlwI and BpmI, respectively (Table 2). Conversely, those type II enzymes which recognize sites with multiple degeneracies are functionally, but not formally, hapaxomers. For example, if a fragment were to be cut at several locations by Bsp1286I (Table 2), an array of single stranded extensions, e.g., GGCC, TGCA, AGCT, GGCA, GGCT, AGCC, AGCA, TGCC, and TGCT, might occur. The first three of these possess an obvious element of symmetry which eliminates them from consideration. The last six protrusions do not possess an element of symmetry and, therefore, are neither self-complementary nor self-ligatable; they have the potential to be unique. On that basis Bsp1286I is a hapaxomer. Hapaxoterminicity is the ability to generate a finite percentage of overhangs lacking in symmetry. The symmetry or lack thereof of the restriction enzyme recognition site is of no consequence.

TABLE 2

```
Alw I         ↓                          A hapaxomer
    GGATCNNNNN                           with an over-
    CCTAGNNNNN                           hang of one
         ↑                               base
    (SEQ ID NO: 21)

BpmI                              ↓      A hapaxomer
    CTGGAGNNNNNNNNNNNNNNNNNN             with an over-
    GACCTCNNNNNNNNNNNNNNNNNN             hang of two
                           ↑             bases
    (SEQ ID NO: 22)

Bsp 1286 I    G     C ↓                  An honorary
            G A G C A C                  hapaxomer
              T     T
              C     G
            C T C G T G
            ↑A      A
```

Bsp1286I has overhangs of four bases on each strand; two bases are uniquely specified and two are restricted to one of three possibilities. Clearly, the statistical probability that the ends are unique is less than that of enzymes which generate two completely unspecified overhanging bases. Such enzymes include BcgI, BpmI, BsaJI, BsgI, BsrDI, DrdI, and Eco57I.

In one embodiment of the invention, a donor vector is obtained or prepared. The donor vector includes a DNA sequence of interest flanked by at least two restriction enzyme sites, at least one of which is for a first restriction enzyme with a degenerate recognition sequence. In another embodiment, the DNA sequence of interest is flanked by two restriction enzyme sites for a restriction enzyme with a degenerate recognition sequence, which sites are not identical and so, once the donor vector is cleaved with that enzyme, yields a linear DNA with non-self complementary single-strand DNA overhangs. The donor vector also contains at least one selectable marker gene which optionally is not the DNA sequence of interest, e.g., the selectable marker gene is part of the vector backbone. The donor vector is useful to transfer the DNA sequence of interest in an oriented manner to an acceptor vector for expression of the DNA sequence of interest in the resulting recipient vector. The acceptor vector contains non-essential DNA sequences flanked by at least two restriction enzyme sites for a second restriction enzyme with a degenerate recognition sequence which yields non-self complementary single-strand DNA overhangs. Those sites, once cleaved, yield single-strand DNA overhangs that are each complementary to only one of the two single-strand DNA overhangs generated by the first restriction enzyme. In one embodiment, the first and second restriction enzymes are the same. In another embodiment, the first and second restriction enzymes are different and are not isoschizomers and so, the resulting ligated sequences (the exchange site) are not cleavable by at least one of restriction enzymes having a degenerate recognition sequence that is employed to transfer the DNA sequence of interest. For example, the fusion of single-strand DNA overhangs generated by BglI and single-strand DNA overhangs generated by SfiI results in an exchange site that is not cleavable by SfiI, but is cleavable by BglI. Similarly, the fusion of single-strand DNA overhangs generated by SgfI and single-strand DNA overhangs generated by PvuI results in an exchange site that is not cleavable by SgfI, but is cleavable by PvuI. Further, the fusion of ends generated by PmeI and ends generated by DraI results in an exchange site that is not cleavable by PmeI, but is cleavable by DraI.

In another approach, a donor vector is obtained or prepared that contains a DNA sequence of interest flanked by at least two restriction enzyme sites, one of which is for a first restriction enzyme which has infrequent restriction sites in cDNAs or open reading frames from at least one species and generates single-strand DNA overhangs, and another of which is for a second restriction enzyme that has infrequent restriction sites in cDNAs or open reading frames from at least one species and generates ends that are not complementary to the overhangs generated by the first restriction enzyme. In one embodiment, the second restriction enzyme generates blunt ends. The donor vector also contains at least one selectable marker gene which optionally is not the DNA sequence of interest. The donor vector is useful to transfer the DNA sequence of interest in an oriented manner to an acceptor vector for expression of the DNA sequence of interest, resulting in a recipient vector. The acceptor vector contains non-essential DNA sequences flanked by at least two restriction enzyme sites. In one embodiment, the non-essential DNA sequences comprise a counter-selectable gene, e.g., a barnase gene, a ccdB gene, or a SacB gene. One of the flanking restriction sites in the acceptor vector is for a third restriction enzyme which generates single-strand DNA overhangs, which overhangs are complementary to the single-strand DNA overhangs produced by digestion of the donor vector with the first restriction enzyme. In one embodiment, the restriction site for the third restriction enzyme is different than the restriction site for the first restriction enzyme and the sites are not cleaved by the same restriction enzyme. In another embodiment, the first and third restriction enzymes are the same. The other flanking restriction site in the acceptor vector is for a fourth restriction enzyme which yields ends that are not complementary to the ends generated by the first or third restriction enzyme. In one embodiment, the second and fourth restriction enzymes generate blunt ends. In one embodiment, the restriction site for the fourth restriction enzyme is different than the restriction site for the second restriction enzyme and the sites are not cleaved by the same restriction enzyme. In this manner, the exchange site is likely not cleavable by the second or fourth restriction enzyme. In another embodiment, the second and fourth restriction enzymes are the same.

Thus, by designing a donor vector and an acceptor vector with selected restriction enzyme sites which are appropriately positioned, once these vectors are digested with the respective restriction enzymes, the DNA sequence of interest can only be oriented in one direction in the acceptor vector backbone.

Restriction enzyme sites useful in the practice of the invention include but are not limited to hapaxomeric sequences, sequences recognized by class II enzymes or class IIS enzymes, as well as restriction enzyme sites recognized by enzymes that yield blunt ends, and including enzymes that are infrequent cutters in one or more species.

Suitable class IIS restriction enzymes include those enzymes that recognize a five-base contiguous sequence, including but not limited to the following enzymes and their isoschizomers, which are indicated in parentheses: Alw26I (BsmAI), AlwI (AclWI, BinI), AsuHPI (HphI), BbvI (Bst71I), BcefI, BstF5I (BseGI, FokI), FauI, HgaI, MboII, PleI, SfaNI, and TspRI; that recognize a six-base contiguous sequence including but not limited to the following enzymes and their isoschizomers: AceIII, BbsI (BbvII, BpiI, BpuAI), Bce83I, BciVI, BfiI (BmrI), BpmI (GsuI), BsaI (Eco31I), BseRI, BsgI, BsmBI (Esp3I), BsmFI, BspMI, BsrDI (Bse3DI), Bsu6I (Earn1104I, EarI, Ksp632I), Eco57I, FauI, MmeI, RleAI, TaqII, and Tth111 II. SapI, and its isoschizomer VapK32I, which recognize a seven-base sequence, and SfiI, which recognizes an eight-base sequence, also can be used. Further examples of useful enzymes include those that recognize a four-base pair split sequence (e.g., Bse4I (BseLI, MsiYI, BslI), MwoI), and enzymes that recognize a six-base pair split sequence (e.g., AccB71 (Esp1396I, PflMI, Van91I), AdeI (DraIII), AhdI (AspEI, Eam1105I, EchHKI, NruGI), AlwNI, ApaBI (BstAPI), AspI (PflFI, Tth111I), BglI, BstXI, DrdI (DseDI), and EcoNI (XagI), XcmI). Additional suitable class IIS restriction enzymes are known to those of skill in the art (see, for example, Szybalski et al., *Gene,* 100:13 (1991)).

There are other enzymes that are not class IIS enzymes, which produce non-palindromic ends. Examples of such enzymes include but are not limited to AvaI (Ama87I, BcoI, BsoBI, Eco88I), AvaII (Eco47I, Bme18I, HgiEI, SinI), BanI (AccB1I, BshNI, Eco64I), BfmI (BstSFI, SfcI), Bpu10I, BsaMI (BscCI, BsmI, Mva1269I), Bsh1285I (BsaOI, BsiEI, BstMCI), Bse1I (BseNI, BsrI, Cfr10I), BsiI (BssSI, Bst2BI), BsiZI (AspS9I, Cfr13I, Sau96I), Bsp1720I (BlpI, Bpu1102I, CelII), Bst4CI, BstDEI (DdeI), CpoI (CspI, RsrII), DsaI (BstDSI), Eco24I (BanII, EcoT38I, FriOI, HgijII), Eco130I (StyI, BssT1I, EcoT14I, ErhI), EspI (BlpI, Bpu1102I, Bsp1720I, CelII), HgiAI (BsiHKAI, Alw21I, AspHI, Bbv12I), HinfI, PspPPI (PpuMI, Psp5II), SanDI, SduI (Bsp1286I, BmyI), SecI (BsaJI, BseDI), SfcI (BfmI, BstSFI), and SmlI.

Other enzymes useful in the invention are those which have few recognition sites in DNA, e.g., cDNAs, of one or more organisms (an "infrequent cutter"). To select restriction enzyme sites for this embodiment of the invention, analyses of sequences for a plurality of mRNAs, open reading frames and/or cDNAs from an organism are conducted, e.g., using computer software, to determine the relative frequency of those sites in that organism (see FIGS. 3-5). For example, SapI has numerous recognition sites in human cDNAs, e.g., 38-43%, while the combination of SgfI and PmeI, and SfiI, have relatively few recognition sites in human cDNAs, for instance, 2 to 3%, and 13 to 14%, respectively. Enzymes which may generate ends complementary to SgfI include but are not limited to Bce83I (BpuEI), BseMII, BseRI, BsgI, BspCNI, BsrDI (Bse3DI, BseMI), BstF5I (BseGI), BtsI, DrdI (AasI, DseDI), EciI, Eco57I (AcuI, BspKT5I), Eco57MI, GsuI (BpmI), MmeI, TaqII, TspDTI, TspGWI, Tth111II, BspKT6I (BstKTI), Pad, PvuI (Afa22MI, Afa16RI, BspCI, EagBI, ErhB9I, MvrI, NblI, Ple19I, Psu161I, RshI, X or II), and SgfI (AsiSI).

Enzymes which generate blunt ends include but are not limited to AhaIII (DraI, PauAII, SruI), AluI (MltI), BalI (MlsI, Mlu31I, MluNI, MscI, Msp20I), BfrBI, BsaAI (BstBAI, MspYI, PsuAI), BsaBI (Bse8I, BseJI, Bsh1365I, BsiBI, BsrBRI, MamI), BsrBI (AccBSI, BstD102I, Bst31NI, MbiI), BtrI (BmgBI), Cac8I (BstC8I), CdiI, CviJI (CviTI), CviRI (HpyCH4V HpyF44III), Eco47III (AfeI, AitI, Aor51HI, FunI), Eco78I (EgeI, EheI, SfoI), EcoICRI (BpuAmI, Ecl136II, Eco53kI, MxaI), EcoRV (CeqI, Eco32I, HjaI, HpyCI, NsiCI), EsaBC3I, FnuDII (AccII, BceBI, BepI, Bpu95I, Bsh1236I, Bsp50I, Bsp123I, BstFNI, BstUI, Bsu1532I, BtkI, Csp68 KVI, CspKVI, FalII, FauBII, MvnI, ThaI), FspAI, HaeI, HaeIII (BanAI, BecAII, Bim19II, Bme361I, BseQI, BshI, BshFI, Bsp211I, BspBRI, BspKI, BspRI, BsuRI, BteI, CltI, DsaII, EsaBC4I, FnuDI, MchAII, MchAII, NgoPII, NspLKI, PalI, Pde133I, PflKI, PhoI, PlaI, SbvI, SfaI, SuaI), HindII (HinJCI, HincII), HpaI (BstEZ359I, BstHPI, KspAI, SsrI), Hpy8I (HpyBII), LpnI (Bme142I), MlyI (SchI), MslI (SmiMI), MstI (Acc16I, AosI, AviII, FdiII, FspI, NsbI, PamI, Pun14627I), NaeI (CcoI, PdiI, SauBMKI, SauHPI, SauLPI, SauNI, SauSI, Slu1777I, SspCI), NlaIV (AspNI, BscBI, BspLI, PspN4I), NruI (Bsp68I, MluB2I, Sbo13I, SpoI), NspBII (MspA1I), OliI (AleI), PmaCI (AcvI, BbrPI, BcoAI, Eco72I, PmlI), PmeI (MssI), PshAI (BoxI, BstPAI), PsiI, PvuII (BavI, BavAI, BavBI, Bsp153AI, BspM39I, BspO4I, Cfr6I, DmaI, EcuI, NmeRI, Pae17kI, Pun14627II, Pvu841I, Uba153AI, UbaM39I), RsaI (AfaI, HpyBI, PlaAII), ScaI (Acc113I, AssI, DpaI, Eco255I, RflFII), SciI, SmaI (CfrJ4I, PaeBI, PspALI), SnaBI (BstSNI, Eco105I), SrfI, SspI, SspD5I, StuI (AatI, AspMI, Eco147I, GdiI, PceI, Pme55I, Sari, Sru30DI, SseBI, SteI), SwaI (BstRZ246I, BstSWI, MspSWI, SmiI), XcaI (BspM90I, BssNAI, Bst1107I, BstBSI, BstZ17I), XmnI (Asp700I, BbvAI, MroXI, PdmI), and ZraI.

In one embodiment, the restriction enzyme site in a vector of the invention is for a restriction enzyme that generates blunt ends and preferably has relatively few recognition sites in a particular organism, e.g., PmeI (MssI), NruI (Bsp68I, MluB2I, Sbo13I, SpoI), SnaBI (BstSNI, Eco105I), SrfI, and SwaI (BstRZ246I, BstSWI, MspSWI, SmiI), as well as HpaI, HincII, PshAI, OliI, AluI, Alw26I, BalI, DraI, DpnI, EcoR47III, EcoRCRI, EcoRV, FokI, HaeIII, HincII, MboI, MspA1I, NaeI, RsaI, PvuII, ScaI, SmaI, SspI, StuI, XmnI, EcaBC3I, SciI, HincII, DraI, BsaBI, Cac8I, Hpy8I, MlyI, PshAI, SspD5I, BfrBI, BsaAI, BsrBI, BtrI, CdiI, CviJI, CviRI, Eco47III, Eco78I, EcoICRI, FnuDII, FspAI, HaeI, LpnI, MlyI, MslI, MstI, NaeI, NlaIV, NruI, NspBII, OliI, PmaCI, PshAI, PsiI, SrfI, StuI, XcaI, XmnI, ZraI or an isoschizomer thereof.

II. Methods to Identify Frequencies of Recognition Sites

FIG. 3 is a flowchart of a method 300 for performing a genetic analysis according to an embodiment of the invention. The method may be performed by one or more computer programs or modules made up of computer-executable instructions. Describing the method by reference to a flowchart enables one skilled in the art to develop such programs or modules including such instructions to carry out the method on suitable computers (the processor or processors of the computer executing the instructions from computer-readable media such as RAM, ROM, CD-ROM, DVD-ROM, hard-drives, floppy drives and other such media). The method illustrated in FIG. 3 is inclusive of acts that may be taken by an operating environment executing an exemplary embodiment of the invention.

A system executing the method begins by populating a database with genetic records obtained from a source database (block 302). Populating a database may be performed using some manual manipulations. In some embodiments, the genetic records comprise gene sequences having open reading frames, e.g., from cDNAs, or a portion thereof. In some embodiments, the database is populated using genetic records that may be obtained from publicly available source databases. For example, in some embodiments human genetic data may be obtained through the Internet using the URL (Uniform Resource Locator) "ftp.ncbinih.gov/refseq/H_sapiens/mRNA_Prot/hs_fna.gz" or the URL mgc.nci.nih.gov/. Genetic data for baker's yeast may be obtained using the URL "genome-ftp.stanford.edu/pub/yeast/data_download/sequence/genomic_sequence/orf_dna." Genetic data for *E. coli* may be obtained from the URL "www.genome.wisc.edu/sequencing/k12.htm." Genetic data for *C. elegans* may be obtained using the URL "ftp.wormbase.org/pub/wormbase/confirmed_genes_current.gz". Genetic data for *Arabidopsis* may be obtained using the URL "tairpub: tairpub@ftp.arabidopsis.org/home/tair/Sequences/blast_datasets/file=ATH1.cds." It should be noted that no embodiment of the invention is limited to any particular source for the genetic data, and that many publicly and privately available sources may be utilized. In one embodiment, the genetic records represent at least 10% or more, e.g., 25%, 50% or more, of the open reading frames in the genome of a selected organism.

The data format for the source data may be different from the format desired for the genetic database. In some embodiments, the source data is converted to a common format for storage in the genetic database.

A query is issued to search for a subset of records in the genetic database that have at least one recognition site for a predetermined restriction enzyme or for a set of predetermined restriction enzymes (block 304). In one embodiment, one or more predetermined restriction enzymes have a 6, 7 or 8 bp recognition site, e.g., a set may include a predetermined restriction enzyme with a 7 bp recognition site and another with a 8 bp recognition site. However, the present invention is not limited to any particular number of restriction enzymes included in the set or to a particular number of by in the recognition site for the one or set of predetermined restriction enzymes. The resulting subset of records may be stored in a temporary table, in a separate results table, or in a separate database.

In some embodiments, the resulting subset of genetic records is filtered to exclude records that may lead to erroneous, skewed, or non-useful results (block 306) or include records with selected characteristics. For example, it has been found that very long sequences in excess of 21,000 bp, a size likely to represent one of the largest open reading frames, typically lead to erroneous, skewed or non-useful results. Other filtering characteristics may also be used and are within the scope of the present invention. Examples of such filtering characteristics include filtering for (to exclude or include) a certain GC content, the presence or absence of introns, specific amino acid compositions in the predicted translation product of the open reading frames, similarity to known genes in specific gene families, a particular isoelectric point of predicted protein products of the open reading frames, and/or predicted membrane spanning proteins in the open reading frames. It should be noted that filtering may occur at any point in the method. For example, the records may be filtered prior to populating the genetic database, or as part of the query to create the subset of records at block 2204.

Next, a set of one or more statistics may be obtained by issuing one or more queries on the subset of records having at least one restriction enzyme recognition site (block 308). In some embodiments, the queries comprise pattern matching queries. The pattern may be specified in any of a number of ways known in the art. For example, wildcard characters may be used to specify one or more positions in the pattern, or regular expressions may be used to specify the pattern. The present invention is not limited to any particular form for specifying a pattern. Additionally, the pattern may be submitted as part of a query to a database engine, or the pattern matching may be executed by a program such as a Visual Basic program on records obtained by a query.

In some embodiments, the number of records having particular restriction enzyme recognition sites is determined and reported (block 310). In some embodiments, in order to be included in the statistics, each record contains recognition sites for all of a predetermined set of restriction enzymes in order to be analyzed.

In alternative embodiments, the number of restriction enzyme target sites occurring in a record is determined and reported (block 312). In some of these alternative embodiments, the record contains recognition sites for all of a predetermined set of restriction enzymes in order to be analyzed.

In further alternative embodiments, statistics regarding the bases at ambiguous positions recognized or cleaved by hapaxomeric restriction enzymes are determined and reported (block 314). The statistics are desirable for determining the distribution of bases in the ambiguous positions of those restriction enzymes. Two examples of such ambiguity are the presence of N's in sites recognized or cleaved by SfiI and SapI as illustrated in FIG. 1. In these alternative embodiments, the identity of any ambiguous bases in the recognition site(s) or bases between the recognition site(s) and the actual cleavage site(s) of some or all of the predetermined restriction enzymes are determined and reported along with one or more statistics on the identity of these bases.

FIGS. 4-5 provide the frequency for various restriction enzyme recognition sites in a variety of organisms determined by the method described herein.

III. Vectors of the Invention

Donor or recipient vectors are used to transfer a DNA sequence of interest, e.g., one in a library, e.g., in a cDNA library, in another vector, e.g., an expression vector, or one obtained from an isolated fragment, e.g., a PCR fragment, which DNA sequence of interest is flanked by desirable restriction enzyme recognition sites, to another vector (an acceptor vector) to generate a recipient (expression) vector, e.g., one useful for expression of the DNA sequence of interest. The presence and position of desirable restriction enzyme recognition sites in the acceptor vector and those flanking the DNA sequence of interest permits the rapid subcloning or insertion of the DNA sequence of interest into the acceptor vector in an oriented manner.

The acceptor vector may include sequences 5' and/or 3' to the desirable restriction enzyme recognition sites which encode a peptide or polypeptide (fusion partner), which sequences, when operably linked to the DNA sequence of interest and expressed in a cell, cell lysate or in vitro transcription/translation system, yield a fusion protein. Such a peptide or polypeptide may be located at either the N- or C-terminus of the fusion protein. Alternatively, the fusion protein may contain a peptide or polypeptide at both the N- and C-terminus, and each peptide or polypeptide may be different. Alternatively, the DNA sequence of interest may itself encode a fusion protein and, once combined with the acceptor vector, result in a recipient vector which encodes a recombinant polypeptide which includes one or more additional residues at the N-terminus, C-terminus, or both the N- and C-termini, which residues are encoded by sequences in the acceptor vector, e.g., those encoded by sequences 5' and/or 3' to the desirable restriction enzyme recognition sites. Moreover, one or more amino acid residues may be encoded by the exchange sites generated by the ligation of the ends of the DNA sequence of interest and the acceptor vector.

In one embodiment, the peptide or polypeptide fusion partner is an epitope tag, affinity domain, e.g., a protease recognition site, or enzyme, e.g., thioredoxin or dehalogenase. An epitope tag is a short peptide sequence that is recognized by epitope specific antibodies. A fusion protein comprising an epitope tag can be simply and easily purified using an antibody bound to a chromatography resin. The presence of the epitope tag further allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), FLAG, c-myc, RYIRS, calmodulin binding domain, the peptide Phe-His-His-Thr-Thr, chitin binding domain, and the like.

Affinity domains are generally peptide sequences that can interact with a binding partner, such as one immobilized on a solid support. DNA sequences encoding metal ion affinity sequences, such as those with multiple consecutive single amino acids, e.g., histidine, when fused to the expressed protein, may be used for one-step purification of the recombinant protein by high affinity binding to a resin column, such as nickel sepharose. An endopeptidase recognition sequence can be engineered between the polyamino acid tag and the protein of interest to allow subsequent removal of the leader peptide by digestion with enterokinase, and other proteases. Sequences encoding peptides or proteins, such as the chitin binding domain (which binds to chitin), GST (which binds to glutathione), biotin (which binds to avidin and strepavidin), maltose binding protein (MBP), a portion of staphylococcal protein A (SPA), a polyhistidine tract ($HIS_n$), and the like, can also be used for facilitating purification of the protein of interest. The affinity domain can be separated from the protein of interest by methods well known in the art, including the use of inteins (protein self-splicing elements, Chong et al., *Gene*, 192:271 (1997). In one embodiment, sequences for more than one fusion partner can be linked to sequences for a peptide or polypeptide of interest, e.g., an affinity domain is linked to a protease cleavage recognition site which is linked to a polypeptide of interest.

To prepare expression vectors intended to generate defined fusions at the 5' end of an open reading frame (e.g., the acceptor vector does not contain sequences 5' of the exchange site that encode a peptide or protein for fusion), a desired restriction enzyme recognition site is placed at the desired start of transcription in the vector. Care is taken to avoid introducing an ATG or start codon upstream of the exchange site that might initiate translation inappropriately. For instance, fusion of an overhang generated by SgfI digestion of an acceptor vector with a compatible overhang which is 5' to a start codon for an open reading frame in a DNA fragment can yield a recombinant vector containing a de novo start site for that open reading frame. Sequences from the acceptor vector which are present in the recombinant vector include sequences 5' to the overhang generated by SgfI digestion, which optionally include a suitably positioned RBS. Optionally, sequences at the 5' end of the open reading frame include a Kozak sequence or a portion thereof which, when present in mRNA, is capable of binding the small subunit of a eukaryotic ribosome.

To prepare expression vectors intended to generate a fusion protein by fusing a vector encoded peptide or protein located at the N-terminus of a fusion protein to a DNA sequence of interest (i.e., a translational fusion), the restriction enzyme recognition site is positioned in the correct reading frame such that 1) an open reading frame is maintained through the restriction enzyme recognition site on the acceptor vector and 2) the reading frame in the restriction enzyme recognition site on the acceptor vector is in frame with the reading frame found on the restriction enzyme recognition site contained within the donor vector. In addition, the appropriate restriction enzyme recognition site on the acceptor vector is designed to avoid the introduction of in-frame stop codons. The DNA sequence of interest contained within the donor vector is thus cloned in a particular reading frame in the acceptor vector so as to facilitate the creation of the desired N-terminal fusion protein. For example, fusion of SgfI sites at the 5' end of a DNA sequence of interest and 3' end of the acceptor vector can provide read through sequences.

Similarly, to prepare expression vectors intended to generate a fusion protein by fusing a vector encoded peptide or protein located at the C-terminus of a fusion protein and a DNA sequence of interest, the restriction enzyme recognition site is positioned in the correct reading frame such that 1) an open reading frame is maintained through the restriction enzyme recognition site on the acceptor vector and 2) the reading frame in the restriction enzyme recognition site on the acceptor vector is in frame with the reading frame found on the restriction enzyme recognition site contained within the donor vector, i.e., a site which flanks the DNA sequence of interest at the 3' end. The DNA sequence of interest contained within the donor vector can thus be cloned in a particular reading frame so as to facilitate the creation of the desired C-terminal fusion protein. For instance, fusion of a PmeI site with a EcoRV or BalI site can yield a C-terminal fusion with at least 2 amino acids added at the C-terminus, while fusion of two PmeI sites or a PmeI site and a DraI site can yield a C-terminal fusion with a single amino acid added at the C-terminus.

In one embodiment, the expression vector encodes a protein with multiple fusion partners, e.g., an affinity tag for purification and a protease cleavage site fused to a protein of interest.

Use of the cloning system herein makes it possible to bring the protein sequence to be expressed in close proximity to the N-terminal and/or C-terminal fusion partner. A particular advantage is that it is possible to select the reading frame. This makes it possible not only to exactly position the DNA sequence of interest but also to define the ends of the fusion gene.

The vectors employed in the practice of the invention also contain one or more nucleic acid sequences that generally have some function in the replication, maintenance or integrity of the vector, e.g., origins of replication, as well as one or more selectable marker genes. Replication origins are unique DNA segments that contain multiple short repeated sequences that are recognized by multimeric origin-binding proteins and which play a key role in assembling DNA replication enzymes at the origin site. Suitable origins of replication for use in expression vectors employed herein include E. coli oriC, colE1 plasmid origin, 2µ and ARS (both useful in yeast systems), sfl, SV40 EBV oriP (useful in mammalian systems), p15 or those found in pSC101 and the like.

Selection marker sequences are valuable elements in vectors as they provide a means to select for or against growth of cells which have been successfully transformed with a vector containing the selection marker sequence and express the marker. Such markers are generally of two types: drug resistance and auxotrophic. A drug resistance marker enables cells to detoxify an exogenously added drug that would otherwise kill the cell. An auxotrophic marker allows cells to synthesize an essential component (usually an amino acid) while grown in media which lacks that essential component.

A wide variety of selectable marker genes are available (see, for example, Kaufman, *Meth. Enzymol.*, 185:487 (1990); Kaufman, *Meth. Enzymol.*, 185:537 (1990); Srivastava and Schlessinger, *Gene*, 103:53 (1991); Romanos et al., in DNA Cloning 2: Expression Systems, 2.sup.nd Edition, pages 123-167 (IRL Press 1995); Markie, *Methods Mol. Biol.*, 54:359 (1996); Pfeifer et al., *Gene*, 188:183 (1997); Tucker and Burke, *Gene*, 199:25 (1997); Hashida-Okado et al., *FEBS Letters*, 425:117 (1998)). Common selectable marker gene sequences include those for resistance to antibiotics such as ampicillin, tetracycline, kanamycin, bleomycin, streptomycin, hygromycin, neomycin, Zeocin™, and the like. Selectable auxotrophic gene sequences include, for example, hisD, which allows growth in histidine free media in the presence of histidinol.

Suitable selectable marker genes include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like.

An alternate approach is to use a selectable marker gene that encodes a mutated enzyme that is less active than the corresponding wild-type enzyme. As an illustration, Munir et al., *Protein Eng.*, 7:83 (1994), describe the design of mutant thymidine kinase enzymes with decreased activity (also see Liu and Summers, *Virology*, 163:638 (1988); Mendel et al., *Antimicrob. Agents Chemother.*, 39:2120 (1995)). Low activity mutants have also been described for adenosine deaminase and dihydrofolate reductase (see, for example, Prendergast et al., *Biochemistry*, 27:3664 (1988); Jiang et al., *Hum. Mol. Genet.*, 6:2271 (1997); Ercikan-Abali et al., *Mol. Pharmacol.*, 49:430 (1996)).

Another type of marker gene is a gene that produces a readily detectable protein, such as green fluorescent protein, red fluorescent protein, an enzyme (e.g., placental alkaline phosphatase, beta-galactosidase, beta-lactamase, or luciferase), or a cell surface protein that can be detected with an antibody (e.g. CD4, CD8, Class I major histocompatibility complex (MHC) protein, etc.). The expression products of such selectable marker genes can be used to sort transfected cells from untransfected cells by such standard means, e.g., FACS sorting or magnetic bead separation technology.

Metallothionein genes encode proteins that have a high affinity for toxic metals, such as cadmium, zinc, and copper (Beach and Palmiter, *Proc. Nat'l Acad. Sci. USA*, 78:2110 (1981); Huang et al., *EXS*, 52:439 (1987); Czaja et al., *J. Cell. Physiol.*, 147:434 (1991)). Accordingly, metallothionein genes provide suitable titratable markers for the methods described herein.

In one embodiment, the acceptor vector includes a counterselectable gene flanked by desirable restriction enzyme sites. Preferred genes in this regard include but are not limited to lethal genes, such as those which are inducible with low to no constitutive activity (and preferably with some immunity factor), e.g., genes such as bar (barstar), those encoding a restriction enzyme (a gene encoding a corresponding methylase), or those encoding nuclease colicins, e.g., E9 DNAse, and colicin RNases and tRNases, or gyrase A, as well as MazF (ChpAK), Doc (Phd), ParE, PasB, StbOrf2, HigB, z, RelE, Txe, YeoB, SacB, KilA, KorA, KorB, Kid (Kis), PemK (PemI), Hok (Sok), Dcc (Pno), CcdB (CcdA), F' plasmid, and the like.

Other selection approaches include the use of regulated transcriptional modulators, e.g., a tertracycline inducible or repressible system (see, for instance, WO 96/01313).

The acceptor vectors employed in the practice of the invention also contain one or more nucleic acid sequences that have some function in the expression of a protein, i.e., transcriptional regulatory sequences, for instance, inducible or repressible control sequences such as promoter or enhancer sequences.

Promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in vectors are transcribed by RNA polymerase II. General transcription factors (GTFs) first bind specific sequences near the start and then recruit the binding of RNA polymerase II. In addition to these minimal promoter elements, small sequence elements are recognized specifically by modular DNA-binding/transactivating proteins (e.g., AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters may be preferred as they are generally particularly strong promoters.

Promoters may be, furthermore, either constitutive or regulatable (i.e., inducible or derepressible). Inducible elements are DNA sequence elements which act in conjunction with promoters and bind either repressors (e.g., lacO/LAC Iq repressor system in $E.$ $coli$) or inducers (e.g., GalI/GAL4 inducer system in yeast rhaBAD/rhanmose in $E.$ $coli$). In either case, transcription is virtually "shut off" until the promoter is derepressed or induced, at which point transcription is "turned-on".

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$, and $P_R$), the trp, reca, lacZ, ladI, araC and gal promoters of $E.$ $coli$, the α-amylase (Ulmanen et al., $J.$ $Bacteriol.$, 162:176 (1985), the araBAD promoter, the rhaBAD promoter, and the sigma-28-specific promoters of $B.$ $subtilis$ (Gilman et al., Gene Sequence, 32:11 (1984), the promoters of the bacteriophages of $Bacillus$ (Gryczan, In: The Molecular Biology of the Bacilli, Academic Press, Inc., NY, 1982), $Streptomyces$ promoters (Ward et at., $Mol.$ $Gen.$ $Genet.$, 203:468 (1986), $Pichia$ promoters (U.S. Pat. Nos. 4,855,231 and 4,808,537), and the like. Exemplary prokaryotic promoters are reviewed by Glick ($J.$ $Ind.$ $Microbiol.$, 1:277 (1987); Cenatiempo ($Biochimie$, 68:505 (1986); and Gottesman ($Ann.$ $Rev.$ $Genet.$, 18:415 (1984). In one embodiment, the promoter is a T7 promoter or a SP6 promoter.

Preferred eukaryotic promoters include, for example, the promoter of the mouse metallothionein I gene sequence (Hamer et al., $J.$ $Mol.$ $Appl.$ $Gen.$, 1:273 (1982); the TK promoter of Herpes virus (McKnight, $Cell$, 31:355 (1982); the SV40 early promoter (Benoist et al., $Nature$ ($London$), 290:304 (1981); the yeast Gall gene sequence promoter (Johnston et al., $Proc.$ $Natl.$ $Acad.$ $Sci.$ ($USA$), 79:6971 (1982); Silver et al., $Proc.$ $Natl.$ $Acad.$ $Sci.$ ($USA$), 81:5951 (1984), a baculovirus promoter, the CMV promoter, the EF-1 promoter, Ecdysone-responsive promoter(s), tetracycline-responsive promoter, and the like.

Suitable prokaryotic vectors include plasmids such as those capable of replication in $E.$ $coli$ (for example, pBR322, ColE1, pSC101, PACYC 184, itVX, pRSET, pBAD (Invitrogen, Carlsbad, Calif.), and the like). Such plasmids are disclosed by Sambrook (cf. Molecular Cloning: A Laboratory Manual, second edition, edited by Sambrook, Fritsch, & Maniatis, Cold Spring Harbor Laboratory, 1989). $Bacillus$ plasmids include pC194, pC221, pT127, and the like, and are disclosed by Gryczan (In: The Molecular Biology of the Bacilli, supra, pp. 307-329). Suitable $Streptomyces$ plasmids include p1J101 (Kendall et al., $J.$ $Bacteriol.$, 169:4177 (1987), and $streptomyces$ bacteriophages such as .phi.C31 (Chater et al., In: Sixth International Symposium on Actinomycetales Biology, Akademiai Kaido, Budapest, Hungary, pp. 45-54, 1986). $Pseudomonas$ plasmids are reviewed by John et al. ($Rev.$ $Infect.$ $Dis.$, 8:693 (1986), and Izaki ($Jpn.$ $J.$ $Bacteriol.$, 33:729 (1978). In one embodiment, the vector backbone for an acceptor vector for expression of linked sequences in $E.$ $coli$ includes an $amp^R$ gene, T7 transcriptional regulatory elements, and sequences for producing a fusion protein such as a GST, thioredoxin or dehalogenase fusion with a protein of interest.

Suitable eukaryotic plasmids include, for example, BPV, EBV, vaccinia, SV40, 2-micron circle, pCI-neo, pcDNA3.1, pcDNA3.1/GS, pYES2/GS, pMT, pIND, pIND (Sp1), pVgRXR (Invitrogen), and the like, or their derivatives. Such plasmids are well known in the art (Botstein et al., Miami $Wntr.$ $Symp.$, 19:265 (1982); Broach, In: The Molecular Biology of the Yeast $Saccharomyces$: Life Cycle and Inheritance, Cold Spring, Harbor Laboratory, Cold Spring Harbor, N.Y. pp. 445-470, 1981; Broach, $Cell$, 28:203 (1982); Dilon et al., $J.$ $Clin.$ $Hematol.$ $Oncol.$, 10:39 (1980); Maniatis, In: Cell Biology: A Comprehensive Treatise, Vol. 3, Gene Sequence Expression, Academic Press, NY, pp. 563-608, 1980. In one embodiment, the vector backbone for an acceptor vector for expression of linked sequences in mammalian cells or an in vitro eukaryotic transcription/translation reaction is pCM-VTnT (Promega Corp.), and sequences for producing a fusion protein such as a GST or dehalogenase fusion with a protein of interest.

Promoters/plasmid combinations are employed with suitable host cells, e.g., prokaryotic cells, such as $E.$ $coli$, $Streptomyces$, $Pseudomonas$ and $Bacillus$, or eukaryotic cells, such as yeast, e.g., $Picchia$, $Saccharomyces$ or $Schizosaccharomyces$, insect cells, avian cells, plant cells, or mammalian cells, e.g., human, simian, parcine, ovine, rodent, bovine, equine, caprine, canine or feline cells, as well as lysates thereof, e.g., TNT, wheat germ lysates or S30 lysates.

In one embodiment, the host cell is a recombinant cell, e.g., a recombinant prokaryotic cell. In one embodiment, the recombinant host cell is deficient in one or more genes in an inducible pathway, e.g., a sugar pathway such as the rhamnose catabolic pathway, and comprises a recombinant DNA comprising an inducible promoter for the one or more genes operably linked to an open reading frame for a heterologous RNA polymerase. The recombinant host cell or a lysate there, or an in vitro transcription/translation mixture supplemented with the heterologous RNA polymerase, is contacted with a vector of the invention comprising a promoter for the heterologous RNA polymerase operably linked to a DNA sequence of interest. In one embodiment, the recombinant host cell is a recombinant *E. coli* cell that is deficient in rhamnose catabolism and comprises a rhaBAD promoter operably linked to a T7 RNA polymerase open reading frame. In the absence of rhamnose, such a cell has no or low levels of T7 RNA polymerase and so is particularly useful to clone toxic genes.

In another embodiment, the recombinant host cell expresses an immunity factor for a gene product that is lethal to the cell. The immunity factor is preferably expressed from a constitutive promoter. An expression vector encoding the lethal gene product may be introduced to the recombinant cell and the transformed cell propagated. In one embodiment the gene product is barnase which has been modified by deleting sequences for the secretory segment (signal peptide) and optionally adding a ATG in place of the last codon for the secretory sequence.

IV. Use of DNA Binding Proteins to Protect Restriction Enzyme Sites

In the process of introducing a DNA sequence of interest to a donor vector, or from a donor vector to an acceptor vector, restriction enzyme sites which flank the DNA sequence of interest, i.e., those useful in cloning, may also be present in either the DNA sequence of interest or vector sequences. To protect sites containing a particular restriction enzyme site from cleavage by the corresponding enzyme, DNA binding proteins and methylation may be employed. For instance, the process of protecting a restriction site with RecA (RecA cleavage and production) is more reproducible, provides better yields and is less cumbersome than partial restriction digests. Other means of protecting a restriction site include using repressor proteins, eukaryotic transcription factors, *E. coli* host integration factor or oligonucleotides capable of forming a triple helix structure, however, the specificity of protection using RecA is entirely from the synthetic single-stranded DNA. In the presence of a nonhydrolyzable ATP analog such as ATP[gamma-S], the RecA protein nonspecifically binds to single-stranded DNA (ssDNA) (approximately one RecA monomer per three nucleotides) to form a structure called a presynaptic filament. This RecA-coated oligonucleotide then anneals with homologous duplex DNA to form a stable triplex DNA-protein complex. The presynaptic filament represents a useful molecular research tool in that: i) the sequence and length of the ssDNA added to the reaction determines the site and span of the presynaptic filament and ii) the presynaptic filament protects the DNA at the hybridization site from modification by DNA methylases and restriction enzymes. These features enable RecA protein-mediated DNA complexes to add a new level of specificity to molecular biology applications that require DNA cleavage at predetermined sites, such as genomic mapping and the subcloning of DNA fragments. Compared to PCR methods, the use of a DNA binding protein is quicker and does not introduce mutations arising from multiple cycles of in vitro amplification.

The general protocols include protecting a restriction site from methylation, making it unique for restriction enzyme cleavage (RecA cleavage), and protecting a restriction site from digestion (RecA protection). The RecA cleavage protocol is based on the RecA Achilles' cleavage procedure of Koob et al. (*Science*, 241, 1084 (1988)), Koob et al. (*Gene*, 74, 165 (1988)), and Koob et al. (*Nucle. Acids Res.*, 20, 5831 (1992)). Additionally, RecA cleavage is useful for generating restriction fragments for subcloning when the desired restriction site is repeated several times within the fragment. However, if only one or two restriction sites are repeated within the desired fragment, RecA protection is preferred. Based on fluorometric analysis of the RecA products after electrophoresis, these two protocols routinely resulted in 70% to 80% protection when a single site was protected. This technique also can be used for DNA embedded in agarose plugs.

TABLE 3

| | |
|---|---|
| Oligonucleotides: Prepared by user to be specific for the intended protected site. Diluted to 160 ng/µl. | Methylase: In theory, any restriction enzyme/methylase pair could be used. In these protocols, 35 µ/µl of EcoRI methylase was used. |
| RecA: 1-3 mg/ml | Restriction enzyme: In these protocols, 12 µ/µl EcoRI was used. |
| SAM: 1.6 mM S-adenosyl methionine. Prepared immediately before use from a 32 mM stock by dilution with ice-cold 5 mM sulfuric acid. | Buffer A: 250 mM Tris-acetate (pH 7.5 at 25° C.), 1 mM magnesium acetate. |
| ATP [gamma-S]: Aliquots of a 10 mM solution (in water) are stored at −70° C. | Buffer B: 166 mM Tris-acetate (pH 7.5 at 25° C.), 37 mM magnesium acetate, 100 mM DTT. 250 mM potassium acetate. |
| 80 mM magnesium acetate. Restriction Enzyme Buffer H (Promega) | |

A. RecA Cleavage or Protection Reactions

The RecA Concentration

To maximize the specificity and efficiency of RecA protection, it may be necessary to manipulate the oligonucleotide:RecA ratio: a concentration of 6.25 µg RecA in a 10 µl reaction works well.

The Oligonucleotide Concentration

The molar stoichiometry (in terms of moles of nucleotides to moles of RecA protein) of the binding of the oligonucleotide to RecA is 3:1. In other words, one RecA protein binds every three nucleotides of any single-stranded DNA. This ratio is independent of oligonucleotide size and corresponds to 160 ng of oligonucleotide per 6.25 µg RecA. A titration series of 40-280 ng in 40 ng increments is useful to determine the optimal concentration of oligonucleotide to use with the RecA. If nonspecific protection is a problem, then 160 ng of oligo(dT) can be added to the reaction after the addition of ATP[gamma-S].

Design of Oligonucleotide

An oligonucleotide of 30 to 36 bases in length is recommended for both RecA cleavage and RecA protection in solution. The protected site was located in the middle of the 30 base oligonucleotide used throughout the development of this protocol (see also *RecA Cleavage and Protection for Genomic Mapping and Subcloning*, from Promega Notes Magazine #50).

Buffer

It may be necessary to adjust the salt concentration to improve the activity of the enzyme after methylation. Acetate salts appear to be less destabilizing to the RecA triplex than chloride salts, and thus potassium acetate rather than potassium or sodium chloride may be employed.

Subcloning the Products of RecA Cleavage

Because the products of a RecA cleavage reaction are methylated, low transformation frequencies may arise from incompatibilities with the host's restriction/modification system. If transformation efficiencies are low, compare the genotype of the host to the known methylation-induced restriction systems to determine if this is the cause.

IV. Exemplary Vector Systems

Figure 6:
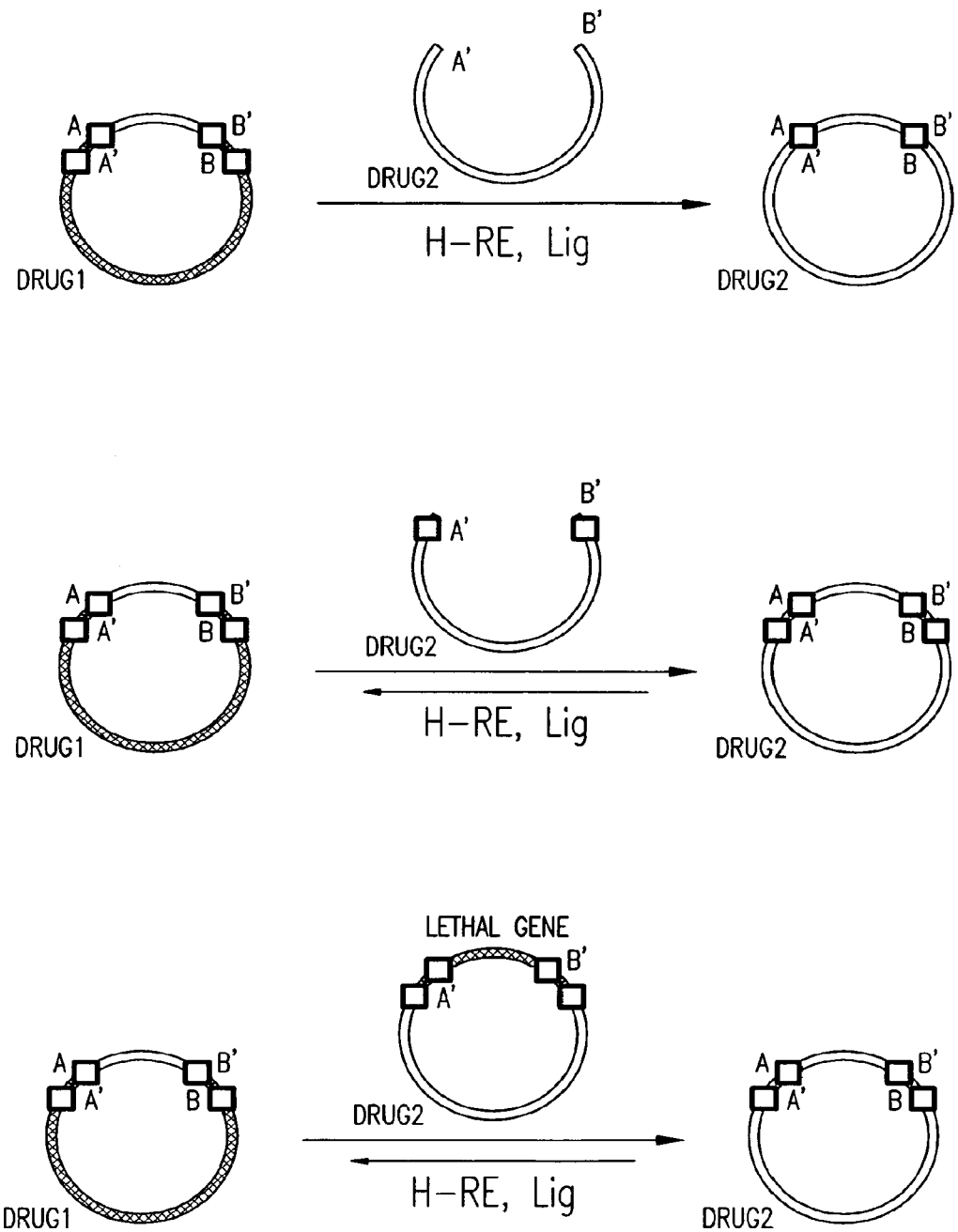
FIG. 6. General overview of the use of interrupted palindromes for directional cloning.

In one embodiment, at least one of the restriction enzyme sites in the donor vector and/or flanking the DNA sequence of interest is for a restriction enzyme with a degenerate recognition sequence, e.g., SfiI is a restriction enzyme with a degenerate recognition sequence that recognizes an interrupted palindromic sequence (FIG. 6). To employ restriction enzymes that recognize an interrupted palindromic sequence and generate single-strand DNA overhangs for use in directional cloning, at least two unique sites for that restriction enzyme and/or unique site(s) for a different restriction enzyme that generates non-self complementary single-strand DNA overhangs that are complementary with the overhangs generated by the first restriction enzyme are employed. Other methods may be used to enhance the frequency of desired vectors, e.g., the use of methylation, and/or selectable and counterselectable genes.

FIG. 7 shows a schematic of the use of donor and acceptor vectors having restriction enzyme sites for a restriction enzyme which recognizes an interrupted palindome (enzyme I; the unique sequences are indicated by A and B, their complements by A' and B', respectively, and the palindromic sequences by boxes). The donor vector has a drug resistance gene 1 and a DNA sequence of interest (light grey box) flanked by one or more restriction enzyme sites for the restriction enzyme which recognizes an interrupted palindome. The acceptor vector has a different drug resistance gene (drug resistance gene 2) and, after digestion with a restriction enzyme with a degenerate recognition sequence, has non-self complementary single-strand DNA overhangs A' and B' which are, respectively, complementary with the non-self complementary single-strand DNA overhangs present after digestion of the donor vector with enzyme I. Thus, after digestion of the donor vector with enzyme I and in the presence of the linearized acceptor vector and ligase, the linearized DNA sequence of interest is joined in an oriented manner to the acceptor vector, to yield a recipient vector. In FIG. 7A, one half site of the restriction site for enzyme I is present at each end of the DNA sequence of interest in the recipient vector. If the ligation regenerates the restriction site, then there is a competing back reaction (FIG. 7B). In FIG. 7C, a counterselectable gene (a lethal gene) is employed in the acceptor vector so that cells with the recipient vector rather than the acceptor vector can be readily identified.

Figure 8:
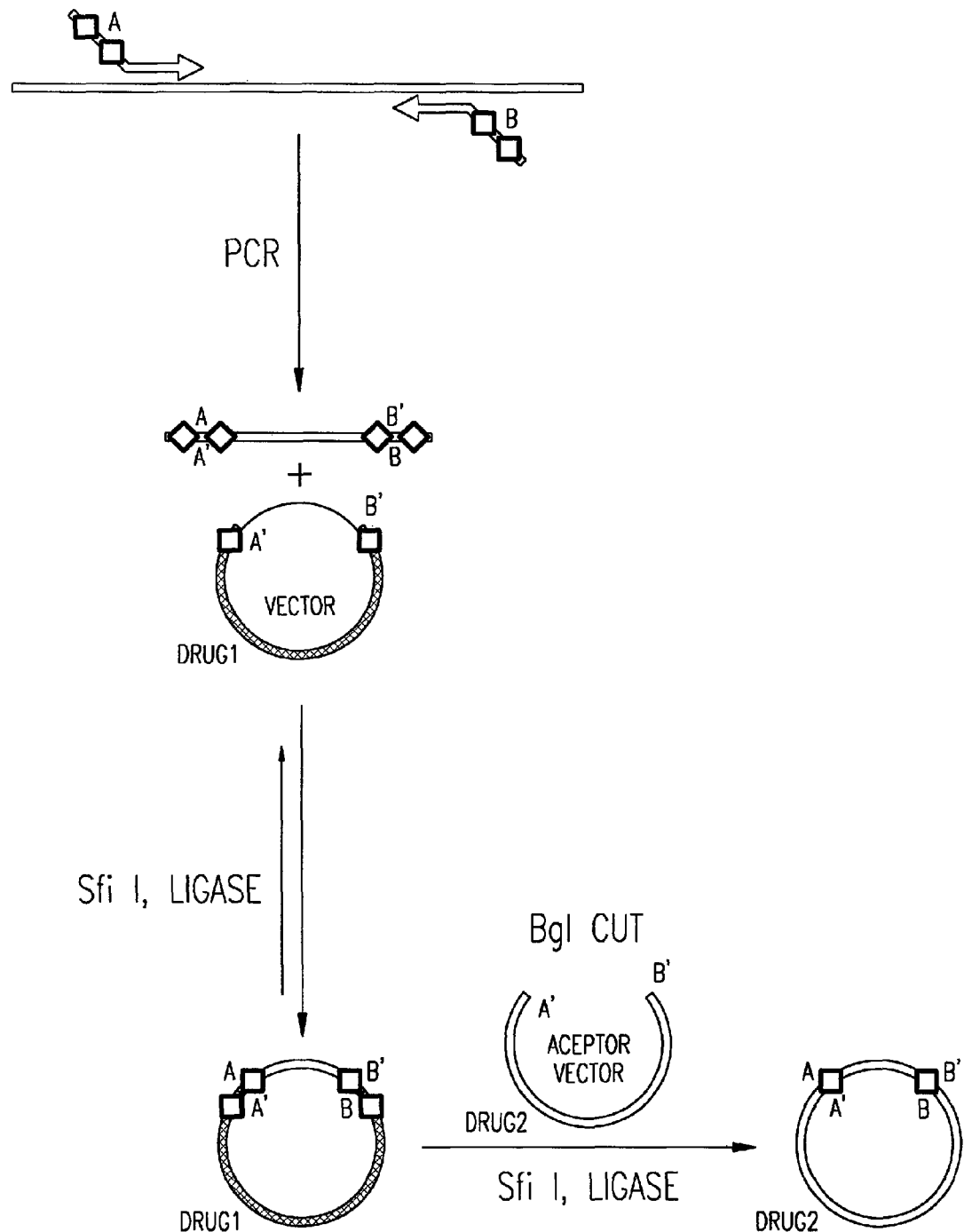
FIG. 8. PCR interrupted palindromes cloning pathways.

FIG. 8 shows one method by which a DNA sequence of interest is modified to contain restriction enzyme sites for a restriction enzyme with a degenerate recognition sequence. Oligonucleotides having unique degenerate sequences for the restriction enzyme at the 5' end, and sequences complementary to one of the strands of the DNA sequence of interest at the 3' end, are employed in an amplification reaction. Those unique sequences are also present in a vector containing a drug resistance gene. The amplified fragment and the vector are digested with the restriction enzyme and ligase added to yield a donor vector of the invention. If the sites are recognized by restriction enzymes which are sensitive to the methylation state of DNA, e.g., at Dcm sites or using a methylase for SfiI, methylation may minimize the back reaction. The donor vector is then digested with a restriction enzyme(s) having degenerate recognition sequences and which releases the DNA sequence of interest, and mixed with an acceptor vector having complementary single-strand DNA overhangs generated by, for example, a different enzyme with a degenerate recognition sequence that generates non-self complementary single-strand DNA overhangs.

Figure 9A:
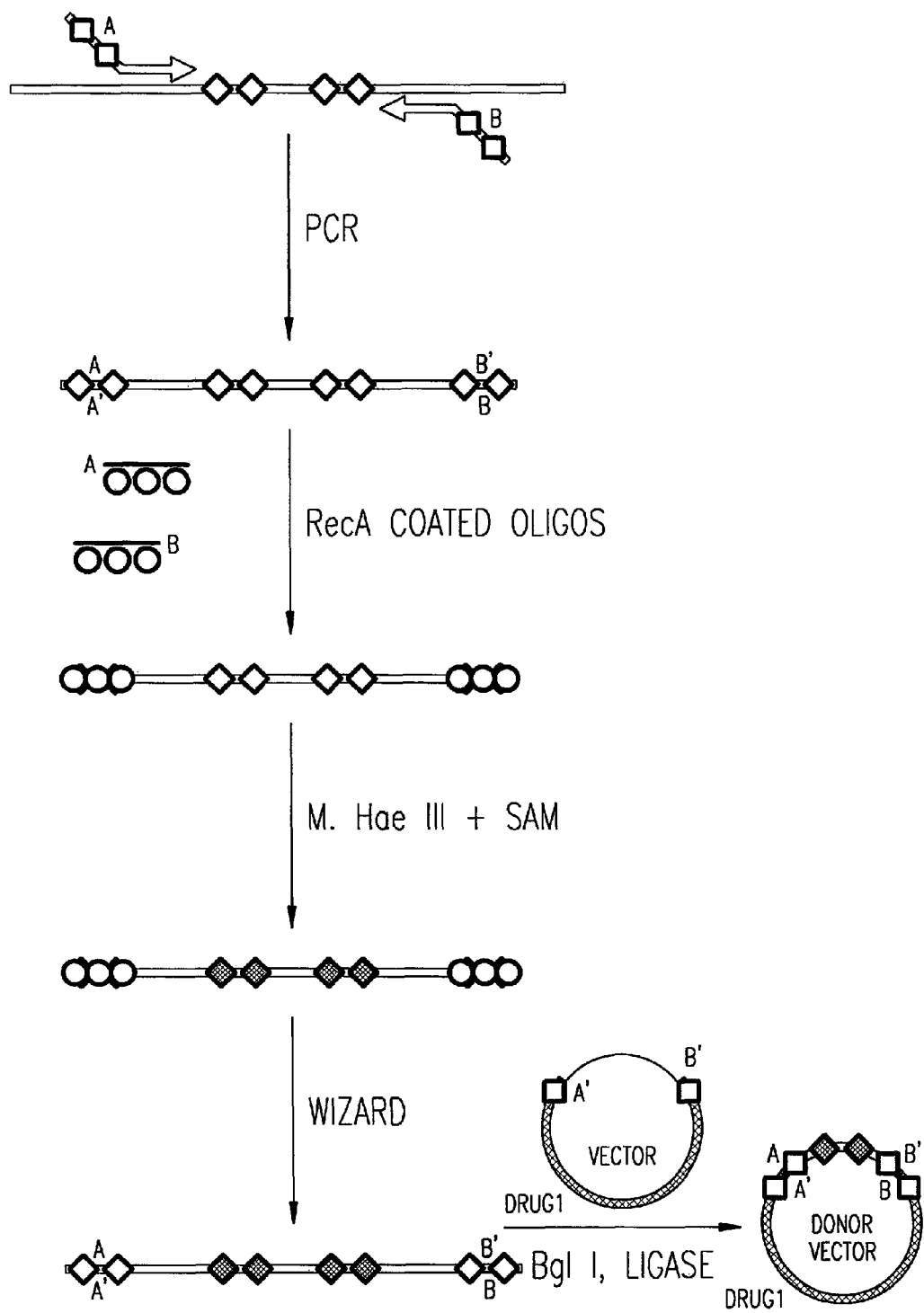
FIGS. 9A-B. PCR interrupted palindromes cloning pathways.
Figure 9B:
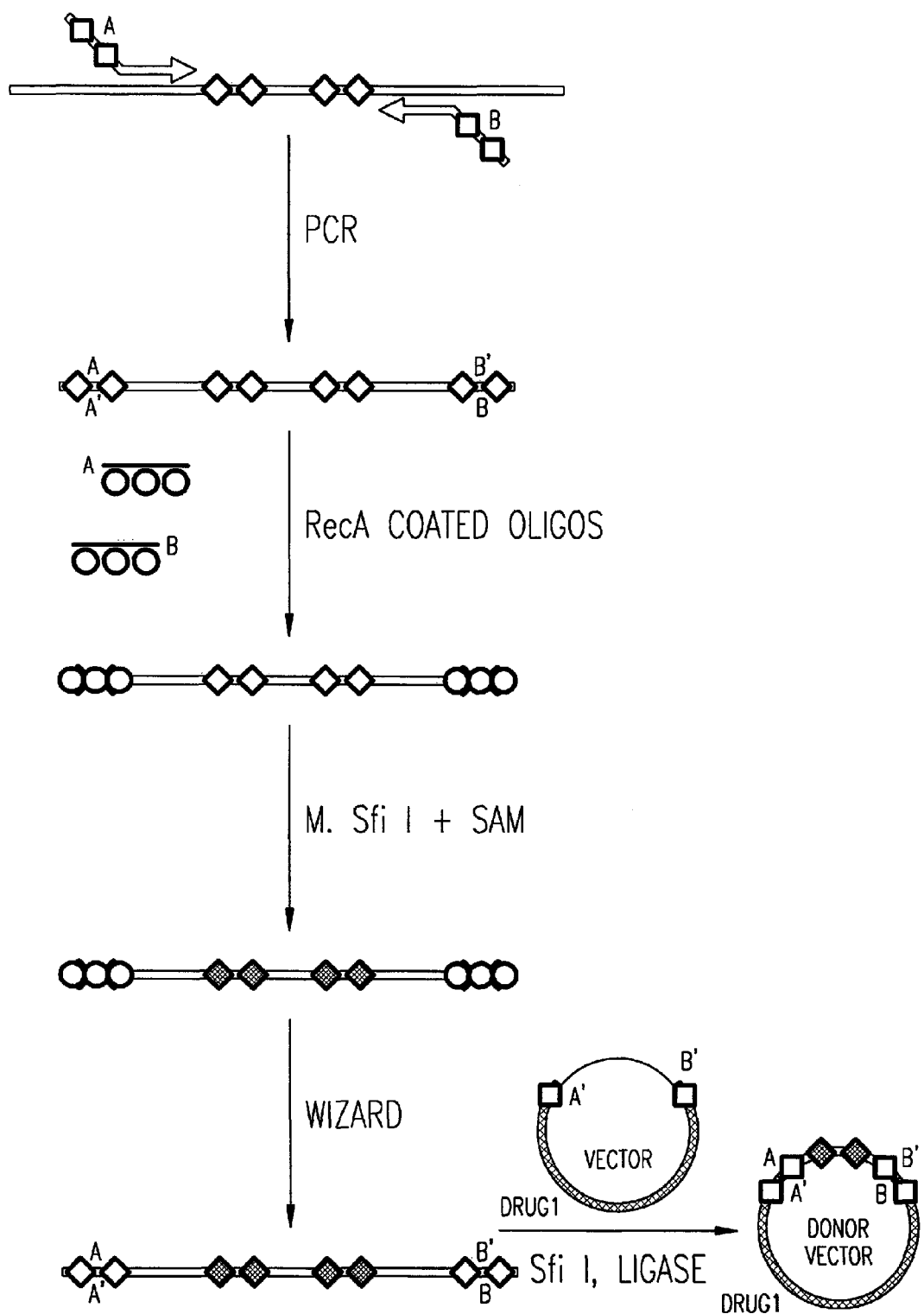

FIGS. 9A-B show another approach to preparing a donor vector of the invention. A DNA sequence of interest is modified to contain restriction enzyme sites for a restriction enzyme with a degenerate recognition sequence. Oligonucleotides having unique degenerate sequences for the restriction enzyme at the 5' end, and sequences complementary to one of the strands of the DNA sequence of interest at the 3' end, are employed in an amplification reaction. The DNA sequence of interest may include internal sites for that restriction enzyme. To protect those internal sites from digestion, they are methylated, while the flanking sites at the ends of the amplified fragment remain unmethylated and therefore sensitive to digestion. To accomplish this, oligonucleotides complementary to the sites which are to remain unmethylated and a DNA binding protein such as RecA are added to the amplified fragment. The internal sites are then methylated with an appropriate methylase. A column may be employed to remove the oligonucleotide-DNA binding protein complexes from the amplified fragment. The sites which were added to the ends of the DNA sequence of interest, once digested, yield non-self complementary single-strand DNA overhangs. Complementary overhangs may be generated in a vector by digestion with a selected restriction enzyme with degenerate recognition sites, which enzyme may be different than the enzyme employed to digest the amplified fragment. The amplified fragment and the vector are then digested with the one or more restriction enzymes, and the resulting linear fragments ligated to form a donor vector containing a drug resistance gene and the DNA sequence of interest flanked by sites generated by the joining of the complementary single-strand DNA overhangs, which sites are recognized by one or more restriction enzymes with a degenerate recognition sequence, e.g., the enzyme employed to digest the amplified fragment.

Figure 10A:
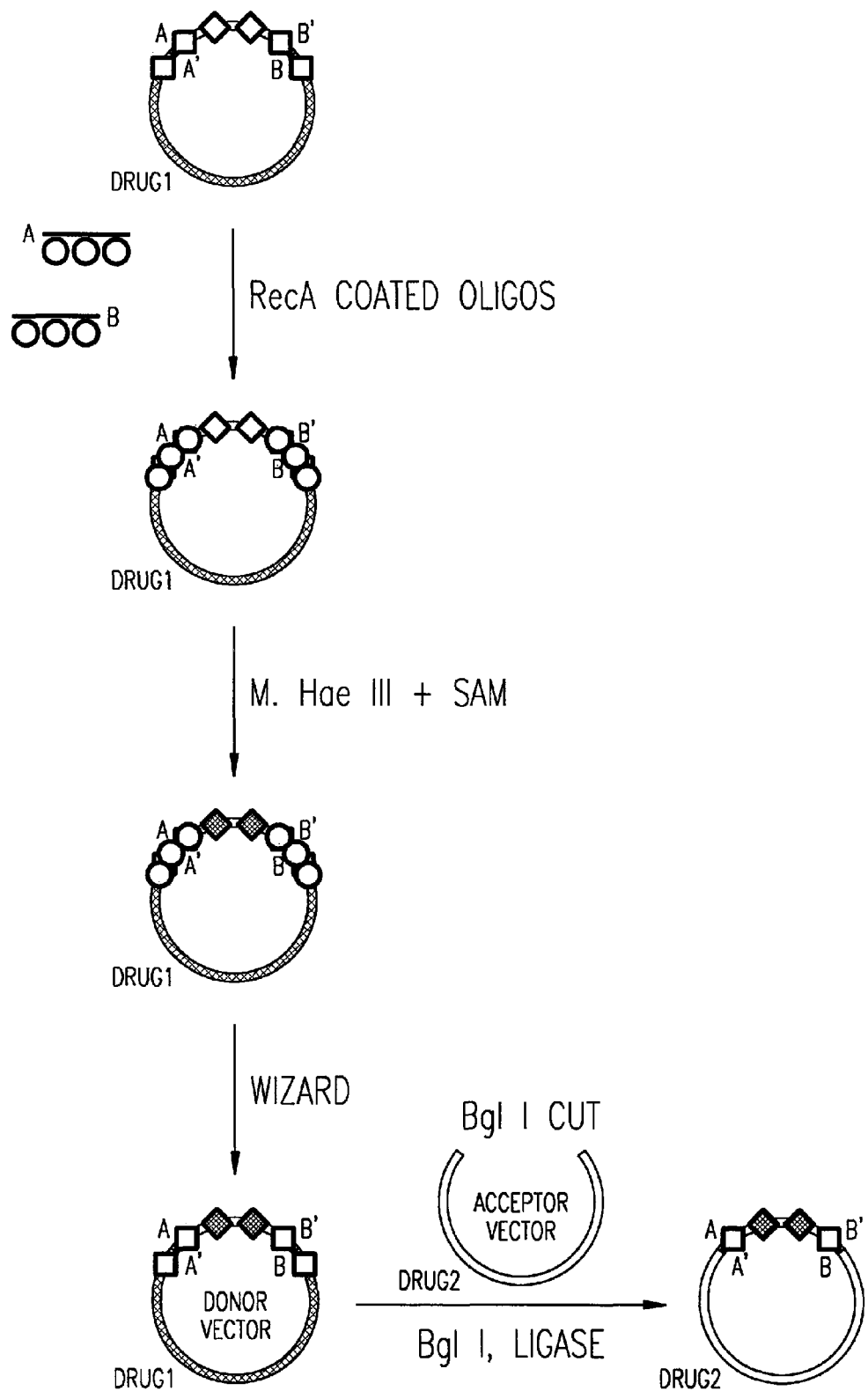
FIGS. 10A-B. PCR interrupted palindromes cloning pathways.
Figure 10B:
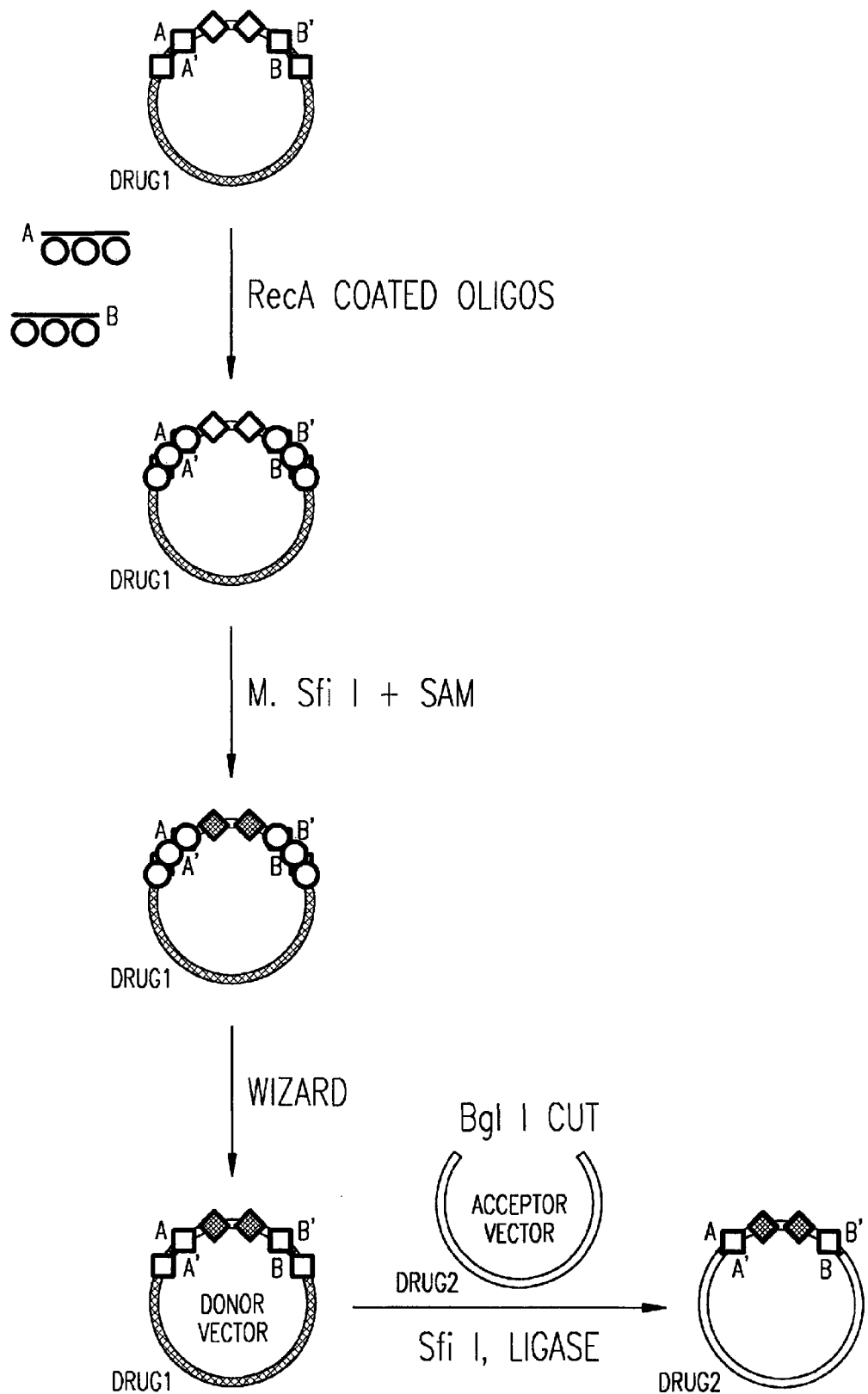

FIGS. 10A-B illustrate an approach to prepare a recipient vector of the invention. In this embodiment, a donor vector comprises a drug resistance gene and a DNA sequence of interest flanked by restriction enzyme sites for an enzyme with a degenerate recognition sequence and containing one or more of those sites internally. To protect those internal sites from digestion, they are methylated. To ensure that the flanking sites remain unmethylated and thus sensitive to digestion, oligonucleotides complementary to the sites which are to remain unmethylated and a DNA binding protein are added to a donor vector. The site(s) for the restriction enzyme which are not bound by the oligonucleotide/DNA binding protein is/are then methylated with an appropriate methylase. A column may be employed to remove the oligonucleotide-DNA binding protein complexes from the donor vector. The donor vector is then added to an acceptor vector having at least two recognition sites for a restriction enzyme with a degenerate recognition sequence, which restriction enzyme produces non-self complementary single-strand DNA overhangs which are complementary to the overhangs generated by digestion of the donor vector with a restriction enzyme that cleaves the unmethylated sites. The acceptor vector preferably comprises a drug resistance gene which is different than the drug resistance gene in the donor vector. In one embodiment, the restriction enzyme used to digest the acceptor vector may be different than the restriction enzyme employed to digest the donor vector. Subsequent ligation of the linearized DNA fragments obtained by digestion of the donor and acceptor vectors yields a recipient vector.

In one embodiment, the restriction enzyme used to linearize the donor vector and the acceptor vector are the same, for instance, the donor vector has unique SfiI sites flanking the DNA sequence of interest, which sites, once digested with SfiI, yield non-self complementary single-strand DNA overhangs that are complementary with the single-strand DNA overhangs generated after digestion of the acceptor vector with SfiI. In another embodiment, the donor vector has unique BglI sites flanking the DNA sequence of interest which sites, once digested with BglI, yield non-self complementary single-strand DNA overhangs that are complementary with the single-strand DNA overhangs generated after digestion of the acceptor vector with BglI. In another embodiment, the restriction enzyme with a degenerate recognition sequence used to linearize the donor vector and the acceptor vector is different, for instance, the donor vector has unique SfiI sites flanking the DNA sequence of interest which sites, once digested with SfiI, yield non-self complementary single-strand DNA overhangs that are complementary with the single-strand DNA overhangs generated after digestion of the acceptor vector with BglI. Restriction enzymes useful with SfiI in preparing donor and acceptor vectors are shown in FIG. 11. Methylases for SfiI and/or BglI may be obtained by well-known methods, see, e.g., U.S. Pat. Nos. 5,179,015, 5,200,333, and 5,320,957. For instance, the preparation of recombinant BglI and its corresponding methylase is disclosed in U.S. Pat. No. 5,366,882. The preparation of recombinant SfiI and a corresponding methylase is provided in U.S. Pat. No. 5,637,476. Other methylases useful with vectors containing SfiI recognition sites include the methylase for HaeIII and Dcm methylase.

Figure 12A:
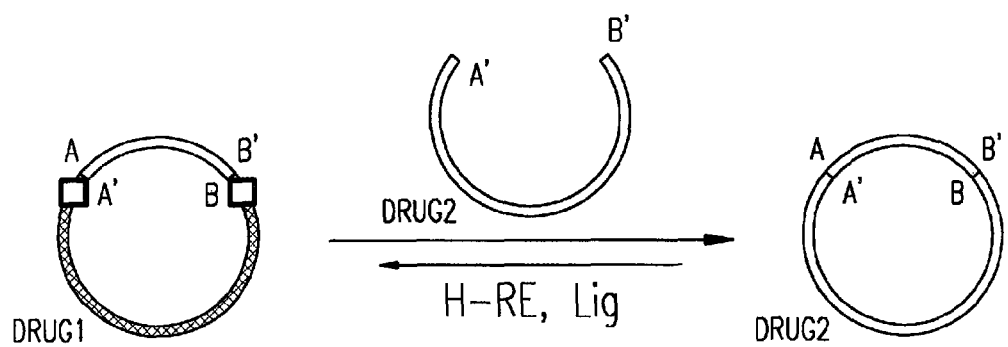
FIG. 12. General overview of the use of Type IIS enzymes for directional cloning.
Figure 12B:
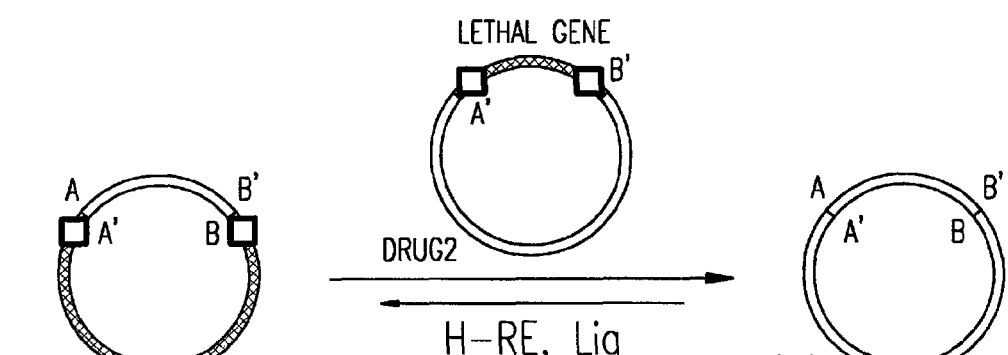

In another embodiment, at least one of the restriction enzyme sites in the donor vector and/or flanking the DNA sequence of interest is a site for a type IIS enzyme, e.g., SapI. FIG. 12 illustrates the preparation of a recipient vector of the invention from a donor vector and an acceptor vector using vectors with recognition sites for type IIS restriction enzymes. To employ sites for type IIS restriction enzymes in directional cloning, at least two unique sites for that restriction enzyme and/or unique site(s) for a different restriction enzyme that generates non-self complementary single-strand DNA overhangs that are complementary with the overhangs generated by the first restriction enzyme are selected. Methylation may be employed to increase the frequency of desired vectors, as well as the use of selectable and counterselectable genes.

In one embodiment, the restriction enzyme used to linearize the donor vector and the acceptor vector are the same, for instance, the donor vector has unique SapI sites flanking the DNA sequence of interest, which sites, once digested with SapI, yield non-self complementary single-strand DNA overhangs that are complementary with the single-strand DNA overhangs generated after digestion of the acceptor vector with SapI. In another embodiment, the donor vector has unique EarI sites flanking the DNA sequence of interest which sites, once digested with EarI, yield non-self complementary single-strand DNA overhangs that are complementary with the single-strand DNA overhangs generated after digestion of the acceptor vector with EarI. In another embodiment, the restriction enzyme used to linearize the donor vector and the acceptor vector is different, for instance, the donor vector has unique SapI sites flanking the DNA sequence of interest, which sites, once digested with SapI, yield non-self complementary single-strand DNA overhangs that are complementary with the single-strand DNA overhangs generated after digestion of the acceptor vector with EarI. The preparation of SapI and a corresponding methylase are disclosed U.S. Pat. No. 5,663,067.

In contrast to the use of SfiI vectors for directional cloning, which yields 12 bases (3 potential codons) at the exchange sites, the use of SapI vectors yields 3 bases (1 potential codon) at the exchange sites. Thus, SapI vectors are particularly useful in recipient vectors as the protein encoded by the DNA sequence of interest in the recipient vector may include only two additional residues, one at the N-terminus and one at the C-terminus, e.g., a codon for methionine at the N-terminus and a residue at the C-terminus which is frequently found at or near the C-terminus of a plurality of proteins. Accordingly, proteins expressed from SapI vectors are very close in composition to their corresponding native protein. Moreover, the overlapping sequences which form the exchange site may be chosen to correspond to codons employed at a certain frequency in a particular organism.

Figures 14A, 14B:
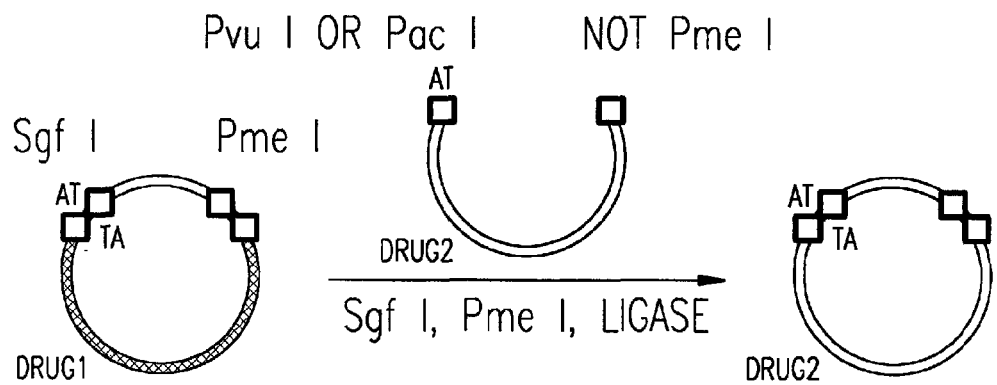
FIGS. 14A-B. Two enzyme approach for directional cloning with an enzyme that generates staggered ends and an enzyme that generates blunt ends, e.g., SgfI and PmeI (e.g. SEQ ID NO: 70). For SEQ ID NO. 70 $n_1$-$n_3$, $n_2n_3G$ or $n_3GC$ is a codon which is not a stop codon.
Figure 15:
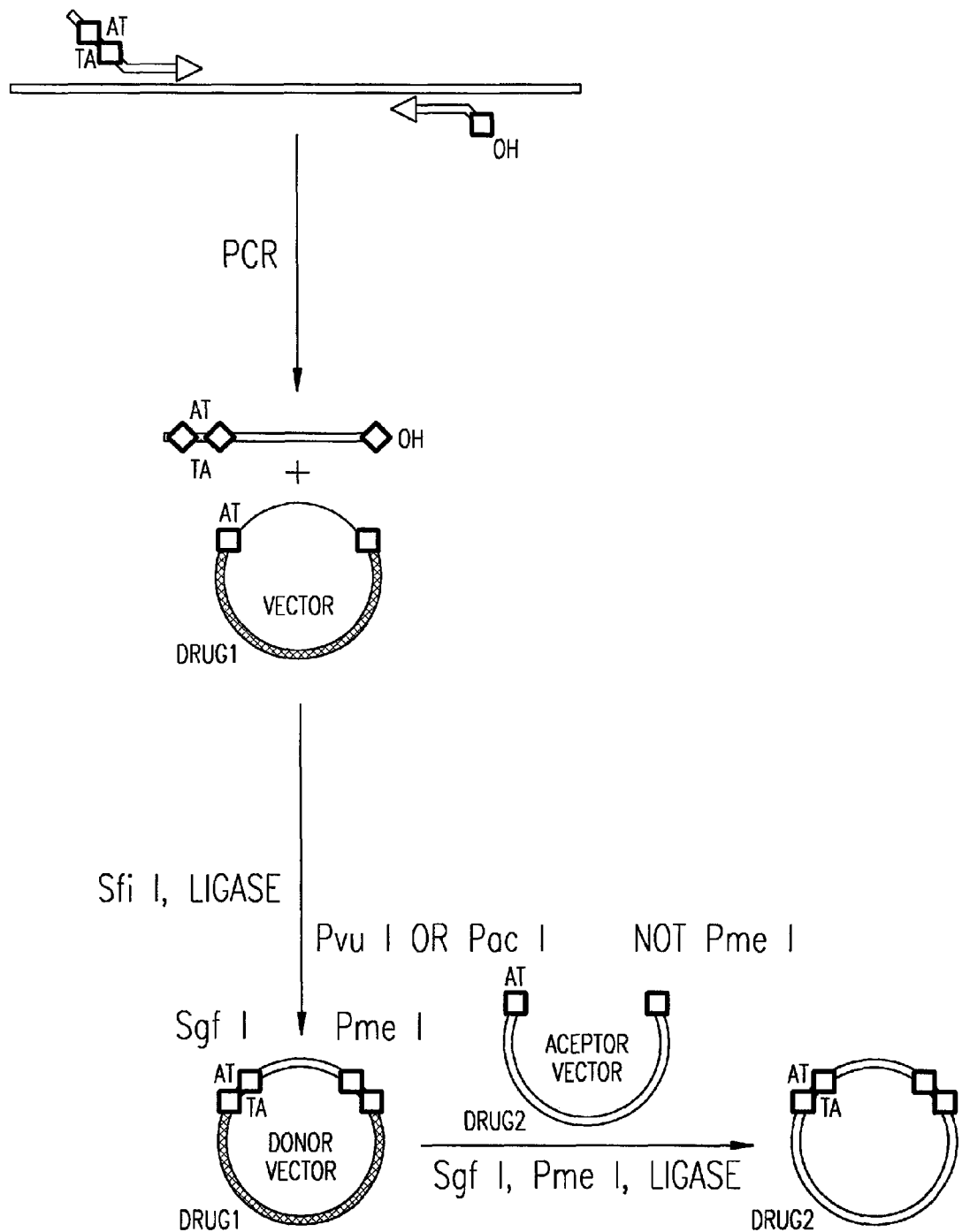
FIG. 15. Two enzyme cloning pathway with PCR entry.

In another embodiment, shown in FIGS. 14-15, a two enzyme approach is used for directional cloning. For the donor vector, the DNA sequence of interest is flanked by at least two restriction enzymes sites. One of the sites is for a first restriction enzyme which is an infrequent cutter of cDNAs or open reading frames in at least one species and generates single-strand DNA overhangs while the other site is for a second restriction enzyme that is also an infrequent cutter of cDNAs or open reading frames in at least one species and generates ends that are not complementary to the ends generated by the first restriction enzyme. In one embodiment, the second restriction enzyme generates blunt ends. For instance, a donor vector has a drug resistance gene 1 and a DNA sequence of interest flanked by a restriction enzyme site for an enzyme (enzyme I) that is an infrequent cutter of human cDNAs or open reading frames and generates a single-strand DNA overhang, e.g., SgfI, and by a site for a restriction enzyme (enzyme II) that in an infrequent cutter in that same species and generates blunt ends, e.g., PmeI. The donor vector which, optionally, is an expression vector, is mixed with an acceptor vector, which has a different drug resistance gene, and at least two restriction enzyme sites, and optionally a counter-selectable gene. One of the sites in the acceptor vector is for a restriction enzyme (enzyme III) that generates single-strand DNA overhangs which are complementary to those generated by enzyme I, e.g., PvuI or PacI, and a restriction enzyme site for an enzyme (enzyme IV) which generates ends which can be ligated to the ends generated by enzyme II, e.g., enzyme IV generates blunt ends, for instance, enzyme IV is PmeI, EcoRV, BalI, or DraI. After digestion with the enzymes, ligation of the linearized donor and acceptors vectors yields a recipient vector comprising the different drug resistance gene and the DNA sequence of interest which is joined to acceptor vector sequences via ligation of the two pairs of complementary single-strand DNA overhangs, or via ligation of complementary single-strand DNA overhangs and blunt ends.

In one embodiment, a DNA sequence of interest is modified to contain restriction enzyme sites for a restriction enzyme which is an infrequent cutter of cDNAs or open reading frames in at least one species and generates single-strand DNA overhangs (enzyme I) and a restriction enzyme that is an infrequent cutter of cDNAs or open reading frames and generates ends that are not complementary to the ends generated by the first restriction enzyme or blunt ends (enzyme II) (FIG. 15). The DNA sequence of interest is mixed with an oligonucleotide having complementary sequences to the site for the infrequent cutter which generates single-strand DNA overhangs and an oligonucleotide having complementary sequences to the site recognized by the enzyme which is an infrequent cutter and generates ends that are not complementary to the ends generated by the first restriction enzyme, e.g., blunt ends, and the mixture is subjected to an amplification reaction, yielding a DNA fragment. In one embodiment, the second restriction enzyme is a blunt cutter. The sites which were added to the ends of the DNA sequence of interest, once digested, yield a single-strand DNA overhang at each end, or a single-strand DNA overhang at one end and a blunt end at the other. Complementary single-strand DNA overhangs to the overhangs generated by enzyme I, or a complementary single-strand DNA overhang to the overhangs generated to enzyme I and a blunt end, are generated in an acceptor vector with restriction enzymes III and IV, respectively, yielding a linearized acceptor vector. The linearized acceptor vector, which comprises a drug resistance gene, is ligated to the digested DNA fragment, to result in a recipient vector. The recipient vector contains the drug resistance gene of the acceptor vector and the DNA sequence of interest flanked by sites generated by the joining of the complementary single-stranded DNA overhangs at each end, or the complementary single-strand DNA overhangs at one end and the blunt ends at the other. The SgfI/PmeI approach can result in a recipient vector which encodes a protein with no additional residues at the N-terminus of the protein, e.g., one positioned 3' to a RBS or Kozak sequence or encoding a fusion protein with an N-terminal or C-terminal fusion of one or more amino acid residues (FIGS. 16-17 and Table I, which shows enzymes which generate blunt ends and the exchange site created by ligation of a blunt end generated by PmeI and a blunt end generated by each of those enzymes).

| Enzymes | Recognition Sequence | Stop Codons w/PmeI | Codon(AA) fusion | Isoschizomers |
|---------|----------------------|--------------------|--------------------|---------------|
| AhaIII | TTT^AAA | TAA | None | DraI PauAII SruI |
| AluI | AG^CT | No | TCT(S) (SEQ ID NO: 24) | MltI |
| BalI | TGG^CCA | No | TCC(S)ANN(IMTNKSR) (SEQ ID NO: 25) | MlsI Mlu31I MluNI MscI Msp20I |
| BfrBI | ATG^CAT | No | TCA(S)TNN(FLSYC) (SEQ ID NO: 26) | — |
| BsaAI | YAC^GTR | No | TGT(C)RNN(IMVTANKDESRG) (SEQ ID NO: 27) | BstBAI MspYI PsuAI |
| BsaBI | GATNN^NNATC (SEQ ID NO: 23) | TAA, TAG, TGA | TNN(FLSYCW)ATC(I) (SEQ ID NO: 28) | Bse8I BseJI Bsh1365I BsiBI BsrBRI MamI |
| BsrBI | CCGCTC (-3/-3) | No | TCT(S)CNN(LPHQR) (SEQ ID NO: 29) | AccBSI BstD102I Bst31NI MbiI |
| BtrI | CACGTC (-3/-3) | No | TGT(C)CNN(LPHQR) (SEQ ID NO: 30) | BmgBI |
| Cac8I | GCN^NGC | TAG | TNG(LSW)CNN(LPHQR) (SEQ ID NO: 31) | BstC8I |
| CdiI | CATCG (-1/-1) | TGA | TGN(C) (SEQ ID NO: 32) | — |
| CviJI | RG^CY | No | TCY(S) (SEQ ID NO: 33) | CviTI |
| CviRI | TG^CA | No | TCA(S) (SEQ ID NO: 34) | HpyCH4V HpyF44III |
| Eco47III | AGC^GCT | No | TGC(C)TNN(FLSYC) (SEQ ID NO: 35) | AfeI AitI Aor51HI FunI |
| Eco78I | GGC^GCC | No | TGC(C)CNN(LPHQR) (SEQ ID NO: 36) | EgeI EheI SfoI |
| EcoICRI | GAG^CTC | No | TCT(S)CNN(LPHQR) (SEQ ID NO: 37) | BpuAmI Ecl136II Eco53kI MxaI |
| EcoRV | GAT^ATC | No | TAT(Y)CNN(LPHQR) (SEQ ID NO: 38) | CeqI Eco32I HjaI HpyCI NsiCI |
| EsaBC3I | TC^GA | TGA | None | — |
| FnuDII | CG^CG | No | TCG(S) (SEQ ID NO: 39) | AccII BceBI BepI Bpu95I Bsh1236I Bsp50I Bsp123I BstFNI BstUI Bsu1532I BtkI Csp68KVI CspKVI FalII FauBII MvnI ThaI |
| FspAI | RTGC^GCAY | No | TGC(C)AYN(IMT) (SEQ ID NO: 41) | — |
| HaeI | WGG^CCW | No | TCC(S)WNN(IMTNKSRFLYC) (SEQ ID NO: 42) | — |
| HaeIII | GG^CC | No | TCC(S) (SEQ ID NO: 43) | BanAI BecAII Bim19II Bme361I BseQI BshI BshFI Bsp211I BspBRI BspKI BspRI BsuRI BteI CltI DsaII |

-continued

| Enzymes | Recognition Sequence | Stop Codons w/PmeI | Codon(AA) fusion | Isoschizomers |
|---|---|---|---|---|
| | | | | EsaBC4I FnuDI McHAII MfoAI NgoPII NspLKI PalI Pde133I PflKI PhoI PlaI SbvI SfaI SuaI |
| HindII | GTY^RAC | TAA, TGA | None | HinJCI HincII |
| HpaI | GTT^AAC | TAA | None | BstEZ359I BstHPI KspAI SsrI |
| Hpy8I | GTN^NAC | TAA, TGA | TYA(FLS)CNN((LPHQR) (SEQ ID NO: 44) | HpyBII |
| LpnI | RGC^GCY | No | TGC(C)YNN(FLSYCLPHQR) (SEQ ID NO: 45) | Bme142I |
| MlyI | GAGTC (5/5) | TAA, TAG, TGA | Any | SchI |
| MslI | CAYNN^NNRTG (SEQ ID NO: 40) | TAA, TAG, TGA | TNN(FLSYCW)RTG(MV) (SEQ ID NO: 46) | SmiMI |
| MstI | TGC^GCA | No | TGC(C)ANN(IMTNKSR) (SEQ ID NO: 47) | Acc16I AosI AviII FdiII FspI NsbI PamI Pun14627I |
| NaeI | GCC^GGC | No | TGG(C)CNN(LPHQR) (SEQ ID NO: 48) | CcoI PdiI SauBMKI SauHPI SauLPI SauNI SauSI Slu1777I SspCI |
| NlaIV | GGN^NCC | No | TNC(FSYC)CNN(LPHQR) (SEQ ID NO: 49) | AspNI BscBI BspLI PspN4I |
| NruI | TCG^CGA | No | TCG(S)ANN(IMTNKSR) (SEQ ID NO: 50) | Bsp68I MluB2I Sbo13I SpoI |
| NspBII | CMG^CKG | No | TCK(S)GNN(VADEG) (SEQ ID NO: 51) | MspA1I |
| OliI | CACNN^NNGTG (SEQ ID NO: 97) | TAA, TAG, TGA | TNN(FLSYCW)GTG(V) (SEQ ID NO: 52) | AleI |
| PmaCI | CAC^GTG | No | TGT(S)GNN(VADEG) (SEQ ID NO: 53) | AcvI BbrPI BcoAI Eco72I PmlI |
| PmeI | GTTT^AAAC | TAA | None | MssI |
| PshAI | GACNN^NNGTC (SEQ ID NO: 54) | TAA, TAG, TGA | TNN(FLSYCW)GTC(V) (SEQ ID NO: 56) | BoxI BstPAI |
| PsiI | TTA^TAA | No | TTA(L)ANN(IMTNKSR) (SEQ ID NO: 68) | — |
| PvuII | CAG^CTG | No | TCT(S)GNN(VADEG) (SEQ ID NO: 57) | BavI BavAI BavBI Bsp153AI BspM39I BspO4I Cfr6I DmaI EclI NmeRI Pae17kI Pun14627II Pvu84II Uba153AI UbaM39I |
| RsaI | GT^AC | No | TAC(Y) (SEQ ID NO: 58) | AfaI HpyBI PlaAII |
| ScaI | AGT^ACT | No | TAC(Y)TNN(FLSYCW) (SEQ ID NO: 59) | Acc113I AssI DpaI Eco255I RflFII |
| SciI | CTC^GAG | TGA | None | — |
| SmaI | CCC^GGG | No | TGG(C)GNN(VADEG) (SEQ ID NO: 60) | CfrJ4I PaeBI PspALI |
| SnaBI | TAC^GTA | No | TGT(S)ANN(IMTNKSR) (SEQ ID NO: 61) | BstSNI Eco105I |
| SrfI | GCCC^GGGC | No | TGG(C)GCN(A) (SEQ ID NO: 62) | — |
| SspI | AAT^ATT | No | TAT(Y)ANN(IMTNKSR) (SEQ ID NO: 63) | — |

-continued

| Enzymes | Recognition Sequence | Stop Codons w/PmeI | Codon(AA) fusion | Isoschizomers |
|---|---|---|---|---|
| SspD5I | GGTGA (8/8) | TAA, TAG, TGA | Any | — |
| StuI | AGG^CCT | No | TCC(S)TNN(FLSYCW) (SEQ ID NO: 64) | AatI AspMI Eco147I GdiI PceI Pme55I SarI Sru30DI SseBI SteI |
| SwaI | ATTT^AAAT | TAA | None | BstRZ246I BstSWI MspSWI SmiI |
| XcaI | GTA^TAC | No | TTA(L)CNN(LPHQR) (SEQ ID NO: 65) | BspM90I BssNAI Bst1107I BstBSI BstZ17I |
| XmnI | GAANN^NNTTC | TAA, TAG, TGA | TNN(FLSYCW)TTC(F) (SEQ ID NO: 66) | Asp700I BbvAI MroXI PdmI |
| ZraI | GAC^GTC | No | TGT(S)CNN(LPHQR) (SEQ ID NO: 67) | — |

Figure 18:
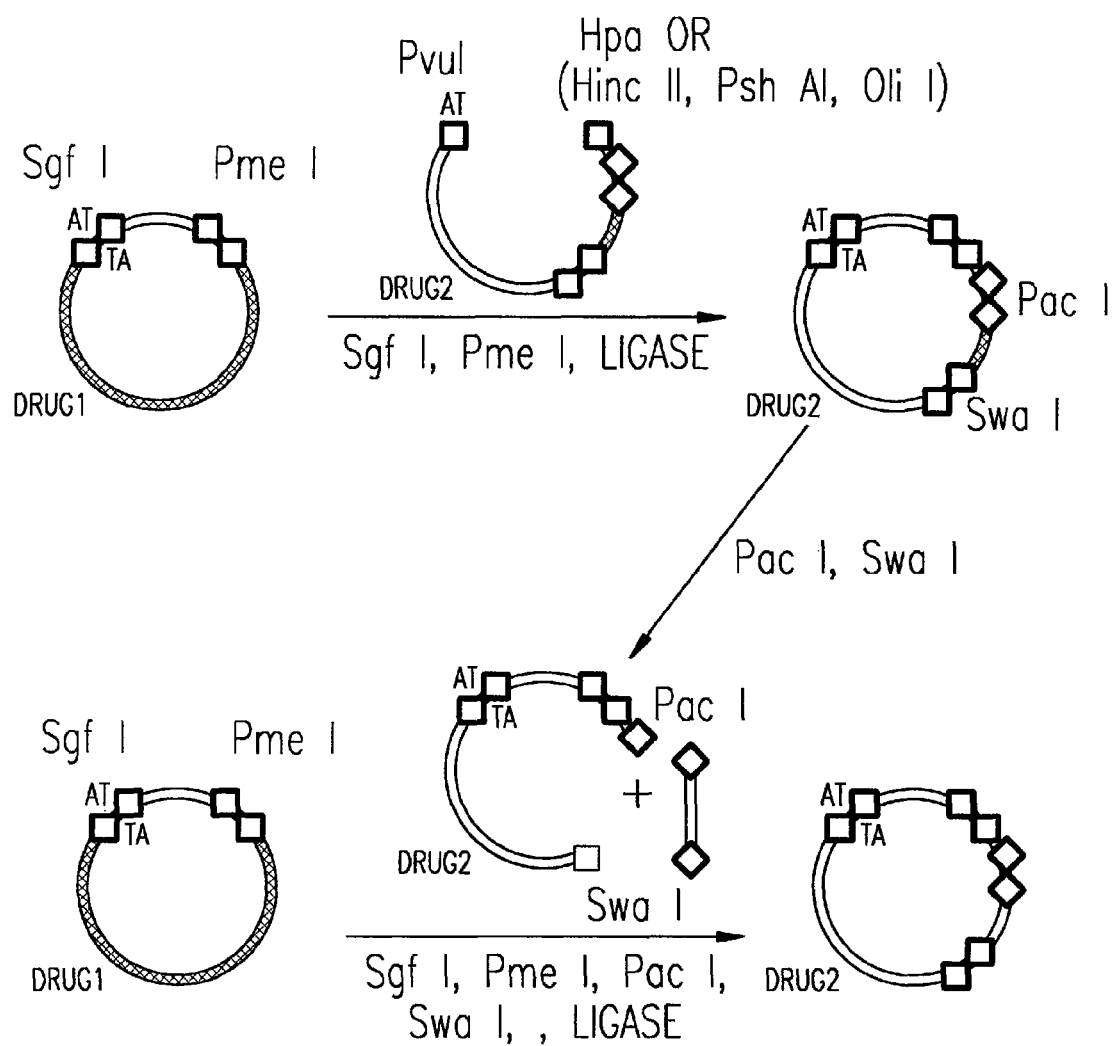
FIG. 18. Use of a combination of SgfI, PmeI, PacI and SwaI to prepare a vector encoding two proteins of interest.

The SgfI/PmeI approach may also be used to introduce two DNA fragments of interest into the same vector (FIGS. 18-19). For example, a donor vector is obtained or prepared that contains a drug resistance gene 1 and a DNA sequence of interest flanked by a restriction site for a restriction enzyme which is an infrequent cutter of cDNAs or open reading frames in at least one species and generates single-strand DNA overhangs (enzyme I), e.g., SgfI, and a site for a restriction enzyme which is an infrequent cutter of cDNAs or open reading frames and generates blunt ends (enzyme II), e.g., PmeI. An acceptor vector is prepared or obtained that contains a drug resistant gene 2, a restriction site for a restriction enzyme (enzyme III) which generates single-strand DNA overhangs that are complementary to the overhangs in a donor vector linearized with enzyme I, which restriction enzyme is different than enzyme I, e.g., PvuI, and a restriction site for an enzyme which generates blunt ends (enzyme IV), and is different than enzyme II, e.g., HpaI. The acceptor vector also includes two additional restriction sites, each of which are 5' or 3' to the DNA sequence of interest in the acceptor vector, one of which is for a restriction enzyme (enzyme V) which generates single-strand DNA overhangs that are complementary to the overhangs generated by enzyme I, which restriction enzyme is different than enzyme I, e.g., PacI, and another for a restriction enzyme that generates blunt ends (enzyme VI), which enzyme is different than enzyme II or enzyme IV, e.g., SwaI. The donor vector is linearized with enzyme I and enzyme II and ligated to an acceptor vector linearized with enzyme III and enzyme IV, to yield a recipient vector having drug resistance gene 2, the DNA sequence of interest, and sites for restriction enzymes V and VI which are both 5' or 3' to the DNA sequence of interest. A second donor vector having a drug resistance gene and a different DNA sequence of interest flanked by a restriction site for enzyme I and another for enzyme II is digested with enzymes I and II, and mixed with the recipient vector, which is linearized with enzymes V and VI, resulting in a second recipient vector having both DNA fragments of interest. Such a recipient vector is useful to study protein-protein interactions, e.g., in two hybrid or colocalization studies, and is particularly useful in systems in which one protein is not expressed or is only expressed at low levels in the absence of expression of a binding protein for that protein.

The invention will be further described by the following non-limiting examples.

Example I

Figure 20A:
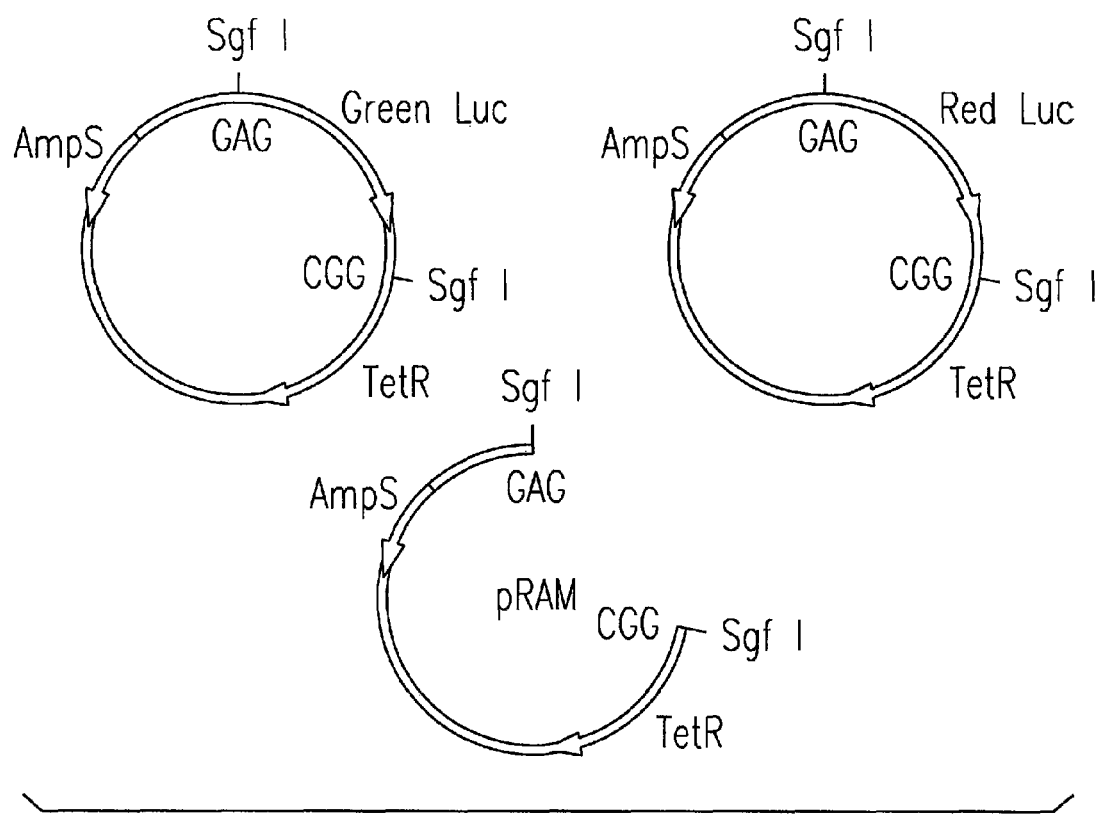
FIG. 20A. Exemplary luciferase donor and acceptor vectors of the invention.

An ampicillin-sensitive donor vector was prepared which has a green light emitting luciferase gene flanked by SfiI sites which, after digestion, do not yield complementary single-strand DNA overhangs (FIG. 20A). An ampicillin resistant acceptor vector was also prepared which has a red light emitting luciferase gene flanked by SfiI sites which, after digestion, do not yield complementary single-strand DNA overhangs but each of which is complementary to one of the single-strand DNA overhangs flanking the green light emitting luciferase gene. These two vectors were digested in T4 DNA ligase buffer with SfiI at 50° C. for 1 hour. The reactions were cooled to room temperature, and T4 DNA ligase added. The ligation reaction was conducted at 22° C. for 30-60 minutes. A portion of the ligation reaction was subjected to gel electrophoresis, while another portion was used to transform JM109. The transformed cells were placed on nitrocellulose and incubated overnight.

Figure 20B:
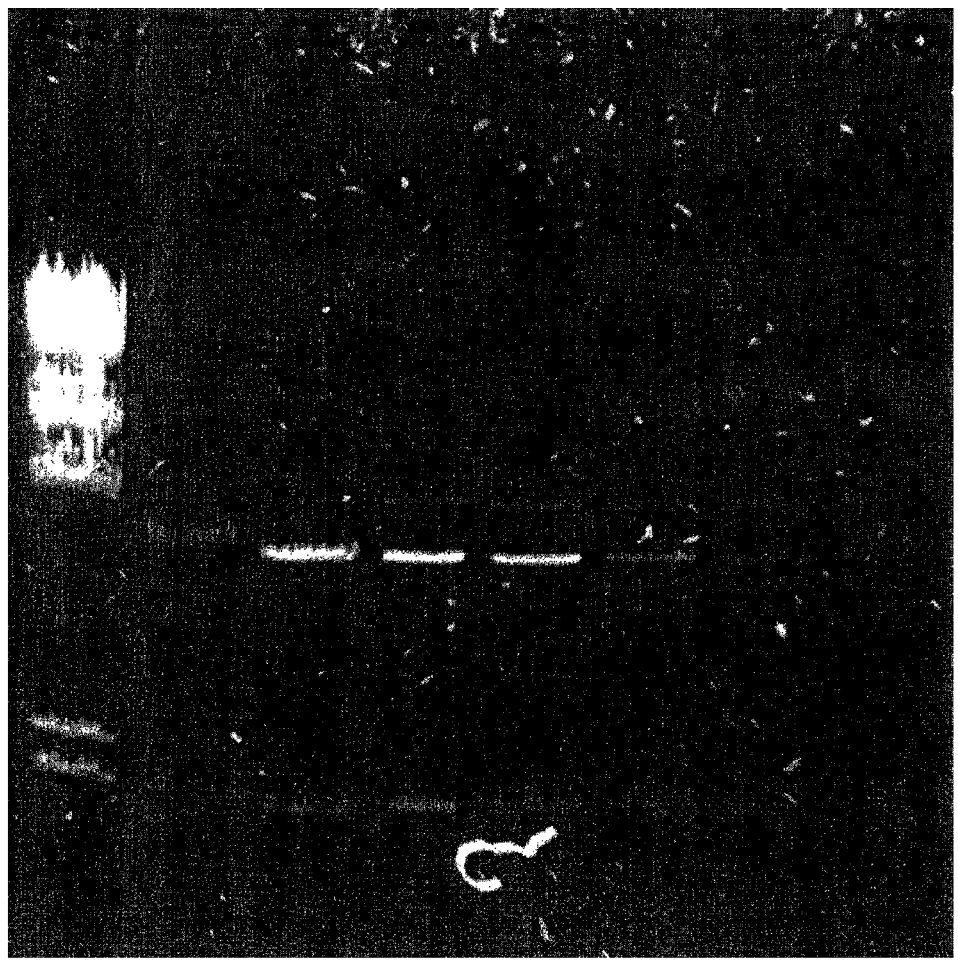
FIG. 20B. Analysis ligation of the donor and acceptor vector sequences having SfiI sites flanking distinguishable luciferase genes.

The filter was floated on 1 ml 100 mM citrate (pH 5.5) with 1 mM luciferin potassium salt at 40° C. An image was then obtained with a CCD digital camera (Minolta Dimage 7; 4 seconds f4.5). The results show that SfiI cuts in ligase buffer, and that the cut ends religate in the presence of T4 DNA ligase (FIG. 20B). To improve the number of desired clones, an acceptor vector containing a counterselectable marker may be employed.

Example II

Vectors

The pDONOR-4 CAT vector was utilized as the source for the chloramphenicol acetyl transferase (CAT) reporter gene with its native promoter between the SgfI and PmeI sites. pDONOR-4 contains a kanamycin resistance gene for bacterial selection, and restriction enzyme sites SgfI and PmeI for directional and flexible cloning.

The pDONOR-6 LacZ vector was utilized as the source for the LacZ reporter gene. pDONOR-6 contains a kanamycin resistance gene for bacterial selection, a T7 bacteriophage promoter, and restriction enzyme sites SgfI and PmeI for directional and flexible cloning.

Figure 21A:
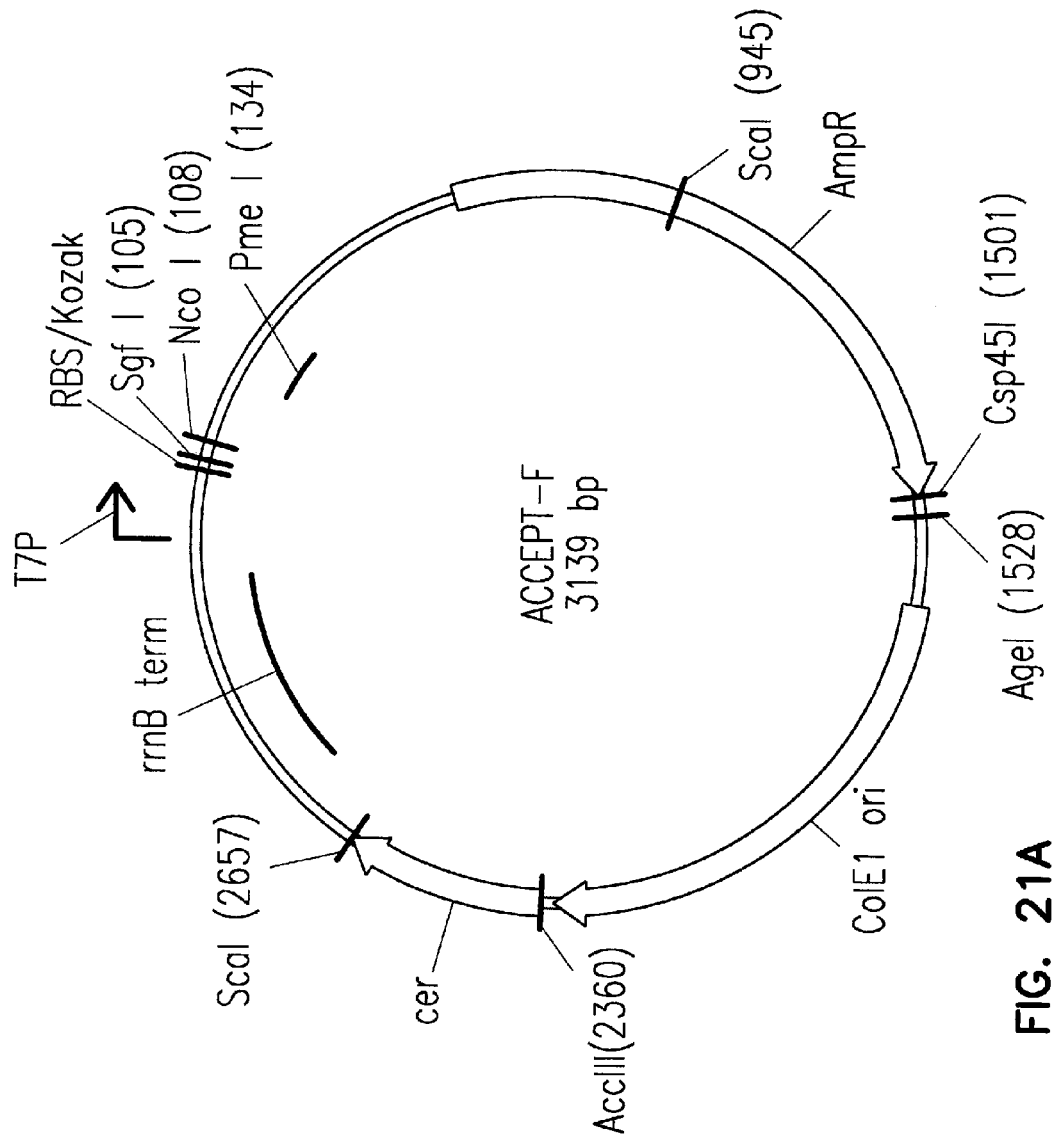
FIG. 21A-E. Exemplary vectors of the invention. KanR=kanamycin resistance gene; AmpR=ampicillin resistance gene; ColE1 ori=origin of replication sequence; cer=XerCD site-specific recombinase target site; rrnB term=bidirectional terminator; T7 P=T7 RNA polymerase promoter; RBS/Kozak=ribosome binding site and Kozak sequences; and T7 term=T7 RNA polymerase termination sequence.
Figure 21B:
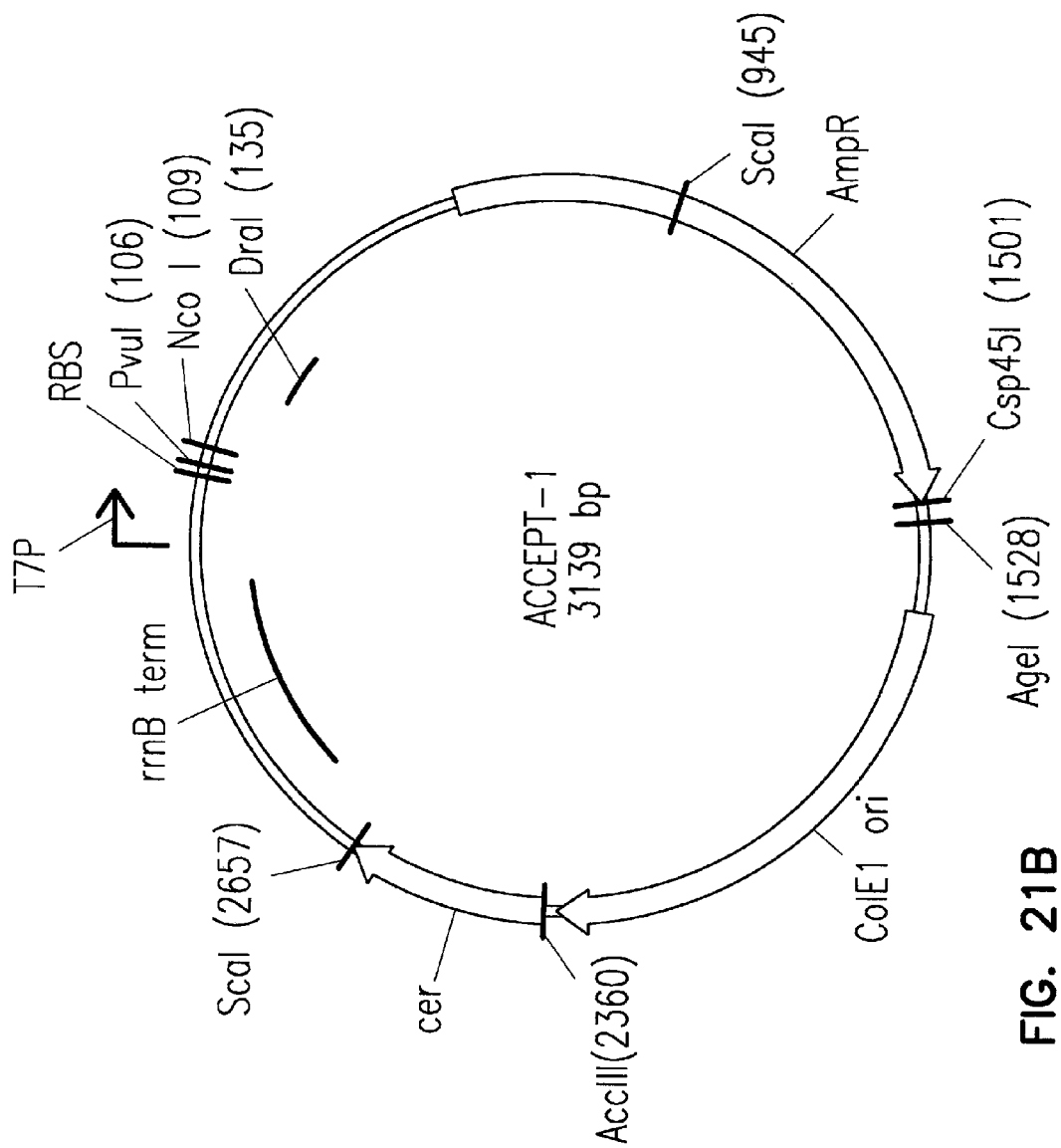
Figure 21C:
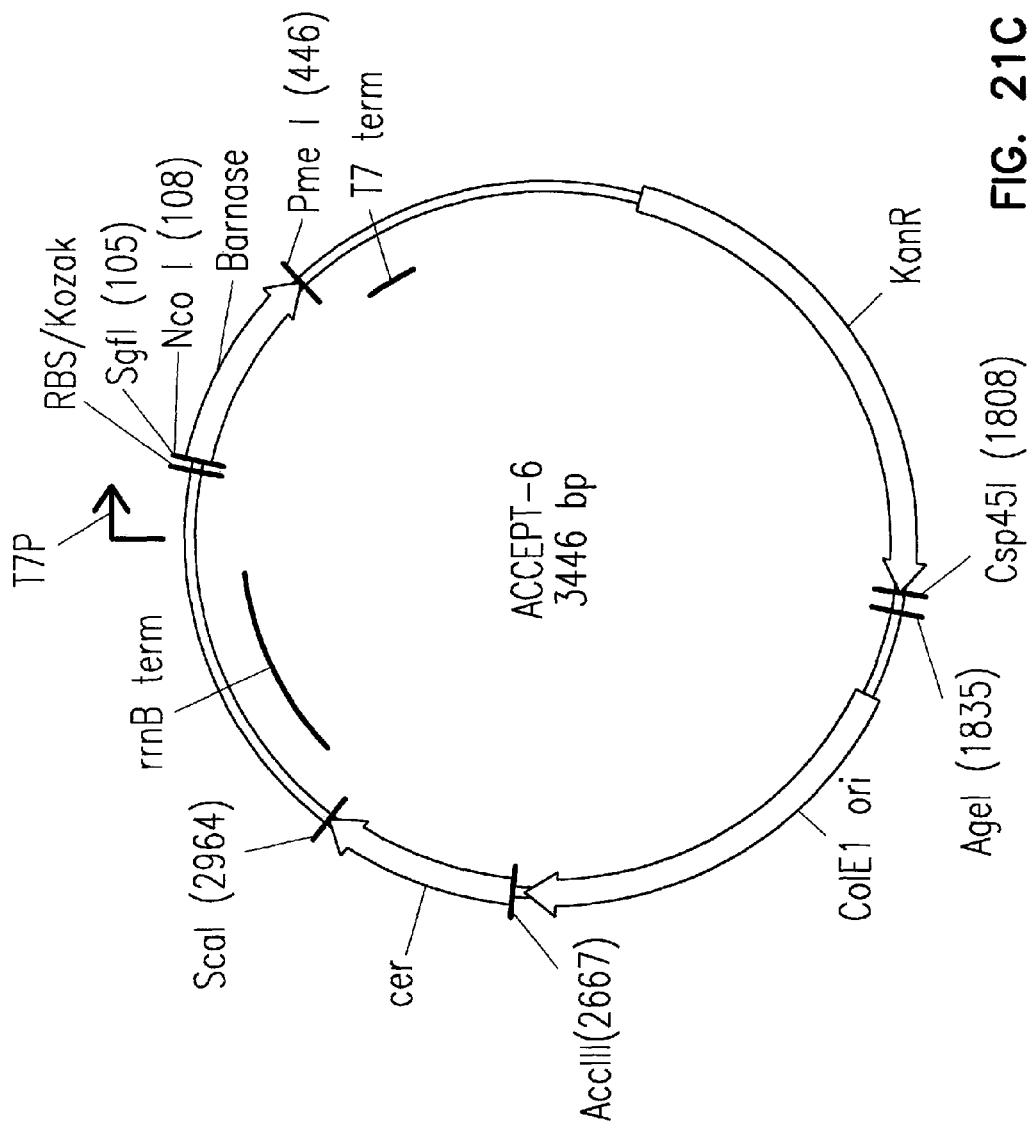
Figure 21D:
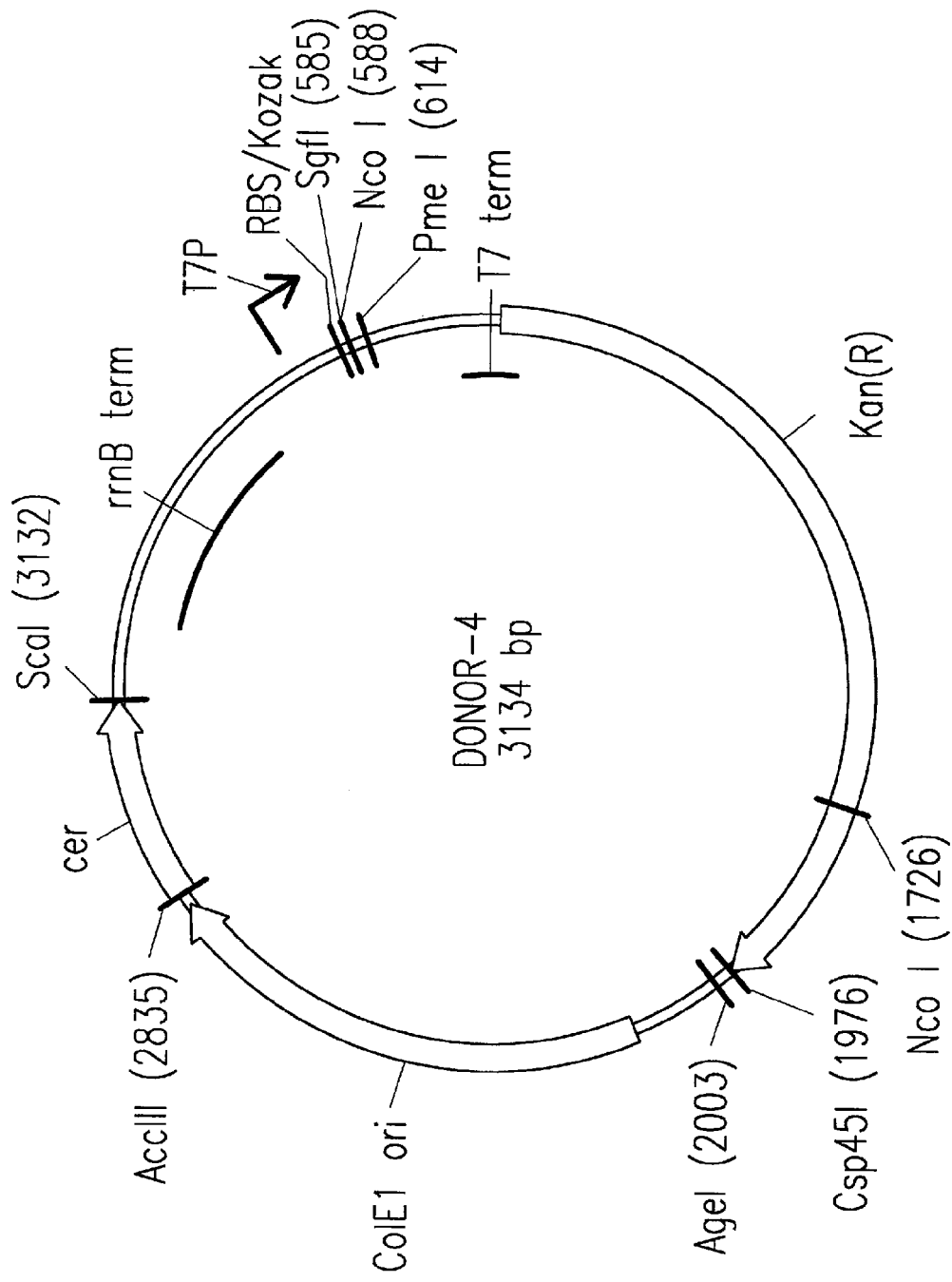
Figure 21E:
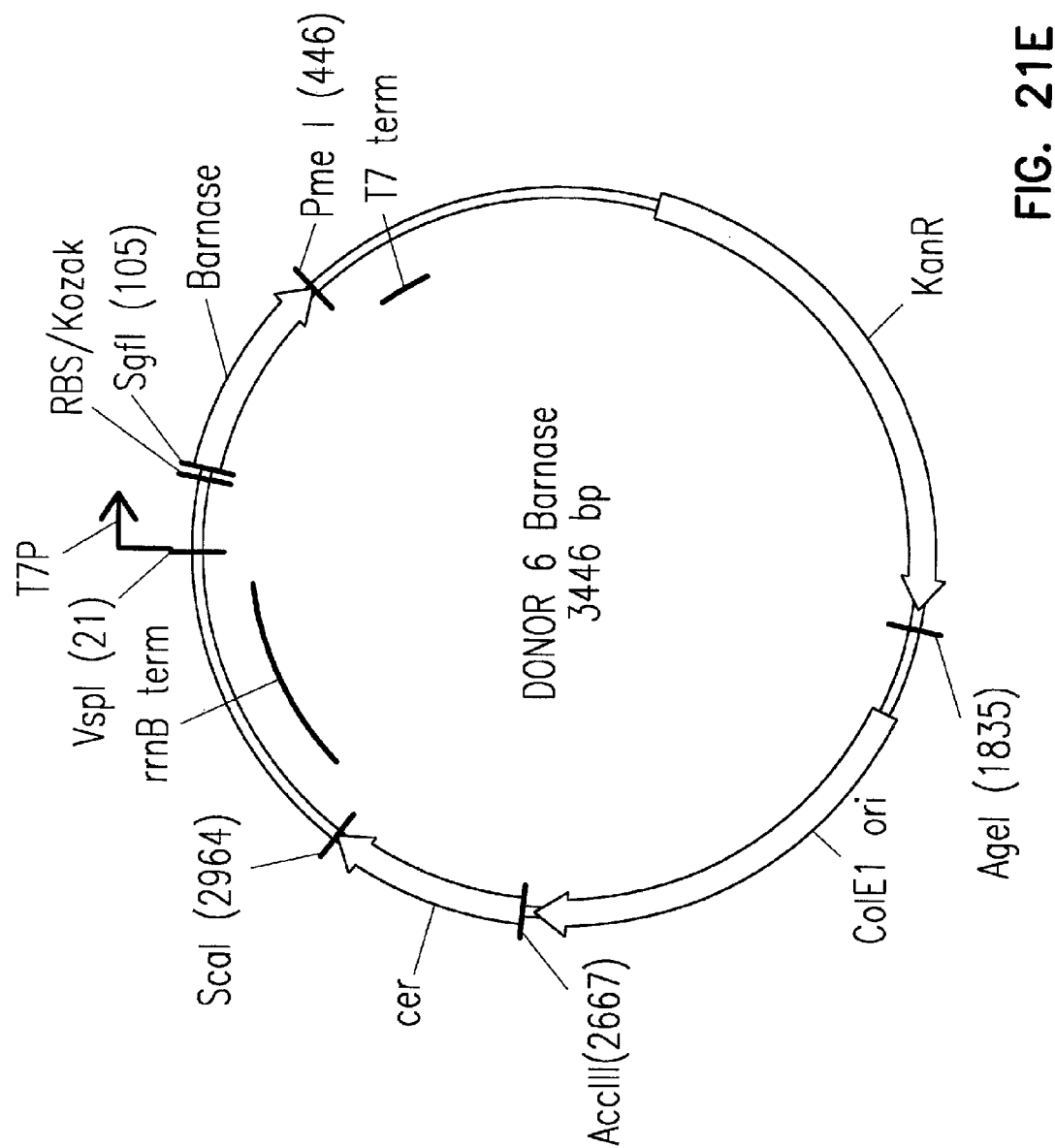

The pACCEPT-F vector (FIG. 21A) was utilized as the source of the backbone sequence for the reporter genes. pACCEPT-F contains an ampicillin resistance gene for bacterial selection, a T7 bacteriophage promoter, and restriction enzyme sites SgfI and PmeI for directional and flexible cloning.

Results

The LacZ reporter gene from pDONOR-6 LacZ was transferred to pACCEPT-F in a two step process. First, pDONOR-6 LacZ was digested with the restriction enzymes SgfI and PmeI in Promega Buffer C with BSA at 37° C. for 1 hour to free the LacZ gene from the vector. Following digestion, the restriction enzymes were inactivated by heating the reaction tube to 65° C. for 20 minutes. Second, linearized pACCEPT-F, T4 DNA ligase, ATP, DTT and additional Buffer C were added to the reaction tube and ligation was initiated by incubating the tube at 22° C. for 1 hour. Following ligation, an aliquot of the reaction was transformed into *E. coli* cells (JM109), and the transformation mixture was plated onto Luria Broth (LB) plates containing ampicillin, X-Gal, and rhamnose. The colonies were visually screened for their ability to utilize X-Gal thereby producing a blue color. Results demonstrated that approximately 90% of the colonies produced a blue color, demonstrating the percent transfer of the LacZ gene from the pDONOR-6 LacZ to the pACCEPT-F vector (percentage was calculated by total # blue colonies/total # colonies×100).

The LacZ reporter gene from pDONOR-6 LacZ was also transferred to the pDEST-F in a two step process. First, vectors pDONOR-6 LacZ and pACCEPT-F were digested in one tube with the restriction enzymes SgfI and PmeI in Promega Buffer C with BSA at 37° C. for 1 hour to free the LacZ gene from the vector. Following digestion, the restriction enzymes were inactivated by heating the reaction tube to 65° C. for 20 minutes. Second, T4 DNA ligase, ATP, DTT and additional Buffer C were added to the reaction tube and ligation was initiated by incubating the tube at 22° C. for 1 hour. Following ligation, an aliquot of the reaction was transformed into *E. coli* cells (JM109), and the transformation mixture was plated onto LB plates containing ampicillin, X-Gal, and rhamnose. Results demonstrated that approximately 81% of the colonies produced a blue color.

The CAT reporter gene from pDONOR-4 CAT was transferred to the pACCEPT-F in a two step process. First, pDONOR-4 CAT was digested with SgfI and PmeI in Promega Buffer C with BSA at 37° C. for 1 hour to free the CAT gene from the vector. Following digestion, the restriction enzymes were inactivated at 65° C. for 20 minutes. Second, linearized pACCEPT-F, T4 DNA ligase, ATP, DTT, and additional Buffer C were added to the reaction tube and ligation was performed at 25° C. for 1 hour. Following ligation, an aliquot of the reaction was transformed into *E. coli* JM109 bacterial cells, and the transformation mixture was plated onto LB plates with ampicillin. Of the resultant colonies, 100 were re-plated onto LB plates with chloramphenicol. Colonies which grew on chloramphenicol contained the CAT gene. Transfer efficiency of the CAT gene from the pDONOR-4 CAT to pACCEPT-F vector was determined to be approximately 94% (percentage was calculated by total # CAT resistant colonies/total # colonies tested×100).

The CAT reporter gene from pDONOR-4 CAT was transferred to the pACCEPT-F in a one step process. To the reaction tube was added pDONOR-4 CAT, linearized pACCEPT-F, restriction enzymes SgfI and PmeI, Promega Buffer C with BSA, T4 DNA ligase, ATP, and DTT. The restriction digest was initiated by incubating the reaction tube at 37° C. for 1 hour. Following digestion, the reaction temperature was lowered to 25° C. for 1 hour to allow for the ligation reaction to occur. Following ligation, an aliquot of the reaction was transformed into *E. coli* JM109 bacterial cells, and the transformation mixture was plated onto LB plates with ampicillin. Of the resultant colonies, 100 were re-plated onto LB plates with chloramphenicol. Colonies which grew on chloramphenicol contained the CAT gene. Transfer efficiency of the CAT gene from the pENTRY-4 CAT to the acceptor vector was determined to be approximately 37%.

Example III

An inducible system useful for cloning including directional cloning includes a recombinant host cell encoding a gene product regulated by an inducible promoter, which gene product specifically increases transcription of a DNA of interest in a vector introduced to the cell. In one embodiment, a first vector includes the open reading frame for a gene of interest operably linked to a promoter, e.g., a T7 promoter, which vector has a transcription terminator sequence, for instance, the rrnB terminator (to reduce aberrant expression), 5' to the promoter, a drug resistance gene, e.g., $kan^R$, sequences which permit the vector to be maintained in a host cell at high copy numbers, optionally sequences which reduce vector multimerization, e.g., cer sequences, as well as restriction enzyme sites flanking the open reading frame. In one embodiment, the restriction enzyme sites flanking the open reading frame are for two different infrequent cutters which do not generate complementary DNA ends (enzyme I and enzyme II) (FIG. 21). The vector in FIG. 21 also includes a T7 transcription terminator 3' of a PmeI site. A second vector having a backbone of interest for the open reading frame, preferably contains a different drug resistance gene, e.g., $amp^R$, and optionally the same transcription terminator sequences, promoter, sequences which permit the vector to be maintained in a host cell at high copy numbers, and optionally sequences which reduce vector multimerization as the vector containing the open reading frame of interest, wherein the transcription terminator sequences and promoter in the second vector are 5' to restriction enzyme sites for two restriction enzymes (enzyme III and enzyme IV) that generate ends that are compatible with ends generated by enzyme I and enzyme II, respectively. For instance, enzyme I is SgfI, enzyme II is PmeI, enzyme III is PvuI, and enzyme IV is DraI. In another embodiment, the restriction sites recognized by enzymes I and III are the same, e.g., sites for SgfI, and the restriction sites recognized by enzymes II and IV are the same, e.g., sites for PmeI. The resulting vector is introduced into a host cell which can be induced to express a gene product which increases transcription of the promoter which is 5' to the open reading frame, e.g., a gene product such as T7 RNA polymerase.

For example, a rhamnose-inducible system including a host cell useful to a clone and express a gene of interest was prepared. For instance, one or more of the rhaBAD catalytic genes in JM109 are deleted, replaced or interrupted via insertional mutagenesis. In one embodiment, the rhaB gene in JM109 was deleted, and a vector with the rhaBAD promoter (e.g., see Egan et al., *J. Mol. Biol.*, 234:87 (1993) and Wilms et al., *Biotech Bioeng.*, 73:95 (2001)) linked to the T7 RNA polymerase open reading frame, stably introduced to those cells, yielding recombinant host cell JM109RX. A vector containing a luciferase gene linked to the T7 promoter was introduced to JM109RX, BL21(DE3) (Novagen), and BL21-AI (Invitrogen) cells. The transformed cells were grown at either 25° C. or 37° C., then contacted with rhamnose (JM109RX), IPTG (BL21(DE3)), or arabinose (BL21-AI), and luciferase activity measured at various time points.

The data showed that there was a much lower level of uninduced luciferase expression in transformed JM109RX cells than in the comparable arabinose inducible system. The rhamnose inducible system may thus be particularly useful to clone toxic genes present in a donor vector or an amplified fragment, although the rhamnose-inducible system is not limited to the cloning of those genes.

Figure 22A:
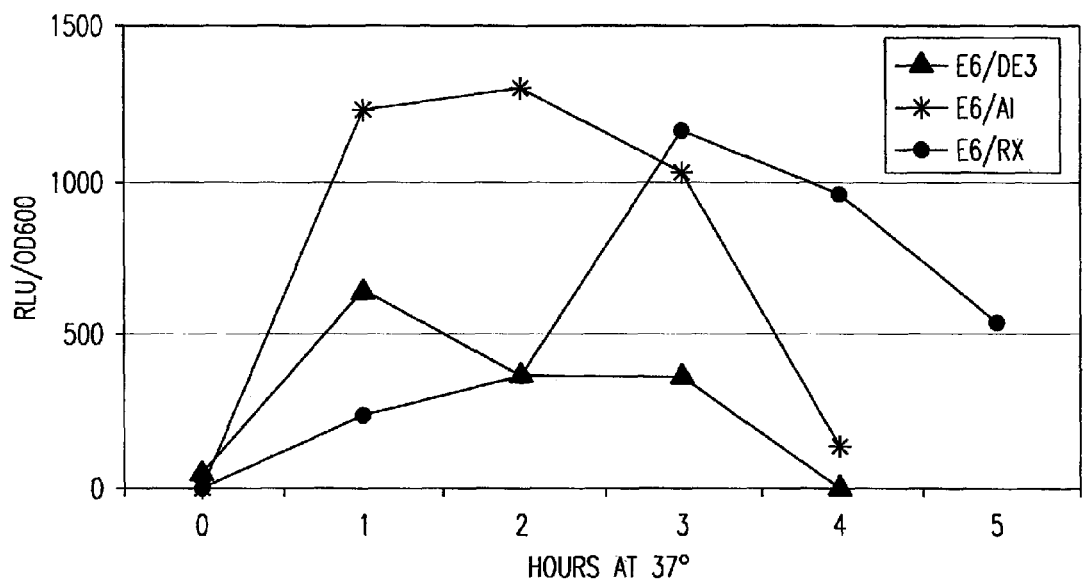
FIG. 22A. Luciferase expression after induction of expression in 3 different hosts at 37° C.
Figure 22B:
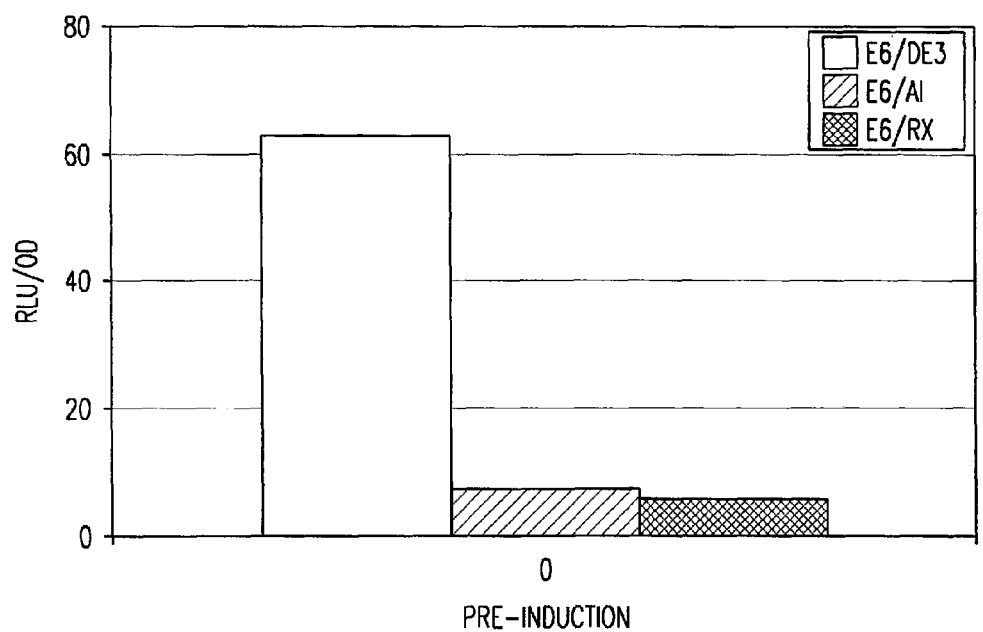
FIG. 22B. Luciferase expression in 3 different hosts at 25° C., t=0.

Moreover, the induction of luciferase activity in transformed JM109RX cells was slow compared to luciferase activity in transformed BL21(DE3) or BL21-AI cells, yet resulted in high final induction levels, e.g., high protein levels, e.g., at times t=4 hours at which RLU were 100× greater (FIG. 22A). Further, the use of a rhamnose-inducible system at 25° C. yielded more luciferase activity than at 37° C., e.g., at least 10-70 fold more at peak (FIG. 22A). The observed expression profile of such a system may allow for increased solubility of the expressed protein, e.g., due to increased time to fold. In addition, the rhamnose-inducible system is glucose repressible. Therefore, combinations of rhamnose and glucose may be employed to finely tune the expression profile of a gene of interest which is linked to a rhaBAD promoter.

Example IV

A system to express a toxic gene was prepared. A stably transformed host cell, JM109, was prepared that contained an expression vector encoding an immunity factor for barnase, barstar, which was expressed from a constitutive promoter, e.g., the 4c promoter, integrated into lamB. A vector containing a lambda $P_L$ promoter linked to a truncated barnase gene (see, e.g., Accession No. X12871 or M14442 (barnase genes from *Bacillus amyloliquefaciens*) or AE007600 (a barnase gene from *Alostridium acetobutylicum*), which lacked the secretory sequence, was introduced to those stably transformed cells.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

SEQUENCE LISTING

```
<160> NUMBER OF SEQ ID NOS: 97

<210> SEQ ID NO 1
<211> LENGTH: 18
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (18)..(18)
<223> OTHER INFORMATION: n is a, c, g, or t

<400> SEQUENCE: 1
aaggagcgat cgccatgn                                                 18

<210> SEQ ID NO 2
<211> LENGTH: 10
<212> TYPE: DNA
<213> ORGANISM: Artificial Sequence
<220> FEATURE:
<223> OTHER INFORMATION: A synthetic DNA fragment, wherein nnn is the
      first codon which is 3' to the start codon followed by the
      remainder of an open reading frame
<220> FEATURE:
<221> NAME/KEY: misc_feature
<222> LOCATION: (8)..(10)
<223> OTHER INFORMATION: n is a, c, g, or t

<400> SEQUENCE: 2 cgccatgnnn                                                          10

<210> SEQ ID NO 3
<211> LENGTH: 12
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(6)
<223> OTHER INFORMATION: n is a, c, g, or t
```

```
-continued

<400> SEQUENCE: 3
nnnnnngtct tc                                                    12

<210> SEQ ID NO 4
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(4)
<223> OTHER INFORMATION: n is a, c, g, or t

<400> SEQUENCE: 4 nnnngaagag                                                       10

<210> SEQ ID NO 5
<211> LENGTH: 13
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (6)..(13)
<223> OTHER INFORMATION: n is a, c, g, or t

<400> SEQUENCE: 5
gcagcnnnnn nnn                                                   13

<210> SEQ ID NO 6
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(5)
<223> OTHER INFORMATION: n is a, c, g, or t

<400> SEQUENCE: 6
nnnnngagac g                                                     11

<210> SEQ ID NO 7
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(8)
<223> OTHER INFORMATION: n is a, c, g, or t

<400> SEQUENCE: 7
gccnnnnngg c                                                     11

<210> SEQ ID NO 8
<211> LENGTH: 14
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (6)..(14)
<223> OTHER INFORMATION: n is a, c, g, or t
```

```
<400> SEQUENCE: 8
ggatgnnnnn nnnn                                                      14

<210> SEQ ID NO 9
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(5)
<223> OTHER INFORMATION: n is a, c, g, or t

<400> SEQUENCE: 9
nnnnngagac c                                                         11

<210> SEQ ID NO 10
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (6)..(10)
<223> OTHER INFORMATION: n is a, c, g, or t

<400> SEQUENCE: 10 gacgcnnnnn                                                           10

<210> SEQ ID NO 11
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (3)..(9)
<223> OTHER INFORMATION: n is a, c, g, or t

<400> SEQUENCE: 11
ccnnnnnnng g                                                         11

<210> SEQ ID NO 12
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (3)..(9)
<223> OTHER INFORMATION: n is a, c, g, or t

<400> SEQUENCE: 12
gcnnnnnnng c                                                         11

<210> SEQ ID NO 13
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(5)
<223> OTHER INFORMATION: n is a, c, g, or t
```

```
<400> SEQUENCE: 13 nnnnngagac                                                         10

<210> SEQ ID NO 14
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(8)
<223> OTHER INFORMATION: n is a, c, g, or t

<400> SEQUENCE: 14
ccannnnntg g                                                       11

<210> SEQ ID NO 15
<211> LENGTH: 15
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (6)..(15)
<223> OTHER INFORMATION: n is a, c, g, or t

<400> SEQUENCE: 15
gtcccnnnnn nnnnn                                                   15

<210> SEQ ID NO 16
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(4)
<223> OTHER INFORMATION: n is a, c, g, or t

<400> SEQUENCE: 16
nnnngaagag c                                                       11

<210> SEQ ID NO 17
<211> LENGTH: 14
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(8)
<223> OTHER INFORMATION: n is a, c, g, or t

<400> SEQUENCE: 17
nnnnnnnngc aggt                                                    14

<210> SEQ ID NO 18
<211> LENGTH: 14
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(9)
<223> OTHER INFORMATION: n is a, c, g, or t
```

```
<400> SEQUENCE: 18
nnnnnnnnng atgc                                                        14

<210> SEQ ID NO 19
<211> LENGTH: 12
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(9)
<223> OTHER INFORMATION: n is a, c, g, or t

<400> SEQUENCE: 19
ccannnnnnt gg                                                          12

<210> SEQ ID NO 20
<211> LENGTH: 13
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (5)..(9)
<223> OTHER INFORMATION: n is a, c, g, or t

<400> SEQUENCE: 20
ggccnnnnng gcc                                                         13

<210> SEQ ID NO 21
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(5)
<223> OTHER INFORMATION: n is a, c, g, or t

<400> SEQUENCE: 21 nnnnngatcc                                                             10

<210> SEQ ID NO 22
<211> LENGTH: 22
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (7)..(22)
<223> OTHER INFORMATION: n is a, c, g, or t

<400> SEQUENCE: 22
ctggagnnnn nnnnnnnnnn nn                                               22

<210> SEQ ID NO 23
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(7)
<223> OTHER INFORMATION: n is a, c, g, or t
```

```
<400> SEQUENCE: 23 gatnnnnatc                                                              10

<210> SEQ ID NO 24
<211> LENGTH: 4
<212> TYPE: PRT
<213> ORGANISM: Artificial Sequence
<220> FEATURE:
<223> OTHER INFORMATION: A synthetic peptide

<400> SEQUENCE: 24

Thr Cys Thr Ser
1

<210> SEQ ID NO 25
<211> LENGTH: 14
<212> TYPE: PRT
<213> ORGANISM: Artificial Sequence
<220> FEATURE:
<223> OTHER INFORMATION: A synthetic peptide

<400> SEQUENCE: 25

Thr Cys Cys Ser Ala Asn Asn Ile Met Thr Asn Lys Ser Arg
1               5                   10

<210> SEQ ID NO 26
<211> LENGTH: 12
<212> TYPE: PRT
<213> ORGANISM: Artificial Sequence
<220> FEATURE:
<223> OTHER INFORMATION: A synthetic peptide

<400> SEQUENCE: 26

Thr Cys Ala Ser Thr Asn Asn Phe Leu Ser Tyr Cys
1               5                   10

<210> SEQ ID NO 27
<211> LENGTH: 19
<212> TYPE: PRT
<213> ORGANISM: Artificial Sequence
<220> FEATURE:
<223> OTHER INFORMATION: A synthetic peptide

<400> SEQUENCE: 27

Thr Gly Thr Cys Arg Asn Asn Ile Met Val Thr Ala Asn Lys Asp Glu
1               5                   10                  15

Ser Arg Gly

<210> SEQ ID NO 28
<211> LENGTH: 13
<212> TYPE: PRT
<213> ORGANISM: Artificial Sequence
<220> FEATURE:
<223> OTHER INFORMATION: A synthetic peptide

<400> SEQUENCE: 28

Thr Asn Asn Phe Leu Ser Tyr Cys Trp Ala Thr Cys Ile
1               5                   10

<210> SEQ ID NO 29
<211> LENGTH: 12
<212> TYPE: PRT
<213> ORGANISM: Artificial Sequence
<220> FEATURE:
<223> OTHER INFORMATION: A synthetic peptide

<400> SEQUENCE: 29
```

Thr Cys Thr Ser Cys Asn Asn Leu Pro His Gln Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: A synthetic peptide

<400> SEQUENCE: 30

Thr Gly Thr Cys Cys Asn Asn Leu Pro His Gln Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: A synthetic peptide

<400> SEQUENCE: 31

Thr Asn Gly Leu Ser Trp Cys Asn Asn Leu Pro His Gln Arg
1               5                   10

<210> SEQ ID NO 32
<211> LENGTH: 4
<212> TYPE: PRT
<213> ORGANISM: Artificial Sequence
<220> FEATURE:
<223> OTHER INFORMATION: A synthetic peptide

<400> SEQUENCE: 32

Thr Gly Asn Cys
1

<210> SEQ ID NO 33
<211> LENGTH: 4
<212> TYPE: PRT
<213> ORGANISM: Artificial Sequence
<220> FEATURE:
<223> OTHER INFORMATION: A synthetic peptide

<400> SEQUENCE: 33

Thr Cys Tyr Ser
1

<210> SEQ ID NO 34
<211> LENGTH: 4
<212> TYPE: PRT
<213> ORGANISM: Artificial Sequence
<220> FEATURE:
<223> OTHER INFORMATION: A synthetic peptide

<400> SEQUENCE: 34

Thr Cys Ala Ser
1

<210> SEQ ID NO 35
<211> LENGTH: 12
<212> TYPE: PRT
<213> ORGANISM: Artificial Sequence
<220> FEATURE:
<223> OTHER INFORMATION: A synthetic peptide

<400> SEQUENCE: 35

Thr Gly Cys Cys Thr Asn Asn Phe Leu Ser Tyr Cys

```
<210> SEQ ID NO 36
<211> LENGTH: 12
<212> TYPE: PRT
<213> ORGANISM: Artificial Sequence
<220> FEATURE:
<223> OTHER INFORMATION: A synthetic peptide

<400> SEQUENCE: 36

Thr Gly Cys Cys Cys Asn Asn Leu Pro His Gln Arg
1               5                   10

<210> SEQ ID NO 37
<211> LENGTH: 12
<212> TYPE: PRT
<213> ORGANISM: Artificial Sequence
<220> FEATURE:
<223> OTHER INFORMATION: A synthetic peptide

<400> SEQUENCE: 37

Thr Cys Thr Ser Cys Asn Asn Leu Pro His Gln Arg
1               5                   10

<210> SEQ ID NO 38
<211> LENGTH: 12
<212> TYPE: PRT
<213> ORGANISM: Artificial Sequence
<220> FEATURE:
<223> OTHER INFORMATION: A synthetic peptide

<400> SEQUENCE: 38

Thr Ala Thr Tyr Cys Asn Asn Leu Pro His Gln Arg
1               5                   10

<210> SEQ ID NO 39
<211> LENGTH: 4
<212> TYPE: PRT
<213> ORGANISM: Artificial Sequence
<220> FEATURE:
<223> OTHER INFORMATION: A synthetic peptide

<400> SEQUENCE: 39

Thr Cys Gly Ser
1

<210> SEQ ID NO 40
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (3)..(3)
<223> OTHER INFORMATION: y = T or C
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (8)..(8)
<223> OTHER INFORMATION: r = A or G

<400> SEQUENCE: 40 caynnnnrtg                                                              10

<210> SEQ ID NO 41
```

```
<211> LENGTH: 10
<212> TYPE: PRT
<213> ORGANISM: Artificial Sequence
<220> FEATURE:
<223> OTHER INFORMATION: A synthetic peptide

<400> SEQUENCE: 41

Thr Gly Cys Cys Ala Tyr Asn Ile Met Thr
1               5                   10

<210> SEQ ID NO 42
<211> LENGTH: 18
<212> TYPE: PRT
<213> ORGANISM: Artificial Sequence
<220> FEATURE:
<223> OTHER INFORMATION: A synthetic peptide

<400> SEQUENCE: 42

Thr Cys Cys Ser Trp Asn Asn Ile Met Thr Asn Lys Ser Arg Phe Leu
1               5                   10                  15

Tyr Cys

<210> SEQ ID NO 43
<211> LENGTH: 4
<212> TYPE: PRT
<213> ORGANISM: Artificial Sequence
<220> FEATURE:
<223> OTHER INFORMATION: A synthetic peptide

<400> SEQUENCE: 43

Thr Cys Cys Ser
1

<210> SEQ ID NO 44
<211> LENGTH: 14
<212> TYPE: PRT
<213> ORGANISM: Artificial Sequence
<220> FEATURE:
<223> OTHER INFORMATION: A synthetic peptide

<400> SEQUENCE: 44

Thr Tyr Ala Phe Leu Ser Cys Asn Asn Leu Pro His Gln Arg
1               5                   10

<210> SEQ ID NO 45
<211> LENGTH: 17
<212> TYPE: PRT
<213> ORGANISM: Artificial Sequence
<220> FEATURE:
<223> OTHER INFORMATION: A synthetic peptide

<400> SEQUENCE: 45

Thr Gly Cys Cys Tyr Asn Asn Phe Leu Ser Tyr Cys Leu Pro His Gln
1               5                   10                  15

Arg

<210> SEQ ID NO 46
<211> LENGTH: 14
<212> TYPE: PRT
<213> ORGANISM: Artificial Sequence
<220> FEATURE:
<223> OTHER INFORMATION: A synthetic peptide

<400> SEQUENCE: 46

Thr Asn Asn Phe Leu Ser Tyr Cys Trp Arg Thr Gly Met Val
1               5                   10
```

```
<210> SEQ ID NO 47
<211> LENGTH: 14
<212> TYPE: PRT
<213> ORGANISM: Artificial Sequence
<220> FEATURE:
<223> OTHER INFORMATION: A synthetic peptide

<400> SEQUENCE: 47

Thr Gly Cys Cys Ala Asn Asn Ile Met Thr Asn Lys Ser Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: A synthetic peptide

<400> SEQUENCE: 48

Thr Gly Gly Cys Cys Asn Asn Leu Pro His Gln Arg
1               5                   10

<210> SEQ ID NO 49
<211> LENGTH: 15
<212> TYPE: PRT
<213> ORGANISM: Artificial Sequence
<220> FEATURE:
<223> OTHER INFORMATION: A synthetic peptide

<400> SEQUENCE: 49

Thr Asn Cys Phe Ser Tyr Cys Cys Asn Asn Leu Pro His Gln Arg
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: A synthetic peptide

<400> SEQUENCE: 50

Thr Cys Gly Ser Ala Asn Asn Ile Met Thr Asn Lys Ser Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: A synthetic peptide

<400> SEQUENCE: 51

Thr Cys Lys Ser Gly Asn Asn Val Ala Asp Glu Gly
1               5                   10

<210> SEQ ID NO 52
<211> LENGTH: 13
<212> TYPE: PRT
<213> ORGANISM: Artificial Sequence
<220> FEATURE:
<223> OTHER INFORMATION: A synthetic peptide

<400> SEQUENCE: 52

Thr Asn Asn Phe Leu Ser Tyr Cys Trp Gly Thr Gly Val
1               5                   10

<210> SEQ ID NO 53
```

```
<211> LENGTH: 12
<212> TYPE: PRT
<213> ORGANISM: Artificial Sequence
<220> FEATURE:
<223> OTHER INFORMATION: A synthetic peptide

<400> SEQUENCE: 53

Thr Gly Thr Ser Gly Asn Asn Val Ala Asp Glu Gly
1               5                   10

<210> SEQ ID NO 54
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(7)
<223> OTHER INFORMATION: n is a, c, g, or t

<400> SEQUENCE: 54 gacnnnngtc                                                              10

<210> SEQ ID NO 55
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(7)
<223> OTHER INFORMATION: n is a, c, g, or t

<400> SEQUENCE: 55 gaannnnttc                                                              10

<210> SEQ ID NO 56
<211> LENGTH: 13
<212> TYPE: PRT
<213> ORGANISM: Artificial Sequence
<220> FEATURE:
<223> OTHER INFORMATION: A synthetic peptide

<400> SEQUENCE: 56

Thr Asn Asn Phe Leu Ser Tyr Cys Trp Gly Thr Cys Val
1               5                   10

<210> SEQ ID NO 57
<211> LENGTH: 12
<212> TYPE: PRT
<213> ORGANISM: Artificial Sequence
<220> FEATURE:
<223> OTHER INFORMATION: A synthetic peptide

<400> SEQUENCE: 57

Thr Cys Thr Ser Gly Asn Asn Val Ala Asp Glu Gly
1               5                   10

<210> SEQ ID NO 58
<211> LENGTH: 4
<212> TYPE: PRT
<213> ORGANISM: Artificial Sequence
<220> FEATURE:
<223> OTHER INFORMATION: A synthetic peptide

<400> SEQUENCE: 58

Thr Ala Cys Tyr
```

```
<210> SEQ ID NO 59
<211> LENGTH: 13
<212> TYPE: PRT
<213> ORGANISM: Artificial Sequence
<220> FEATURE:
<223> OTHER INFORMATION: A synthetic peptide

<400> SEQUENCE: 59

Thr Ala Cys Tyr Thr Asn Asn Phe Leu Ser Tyr Cys Trp
1               5                   10

<210> SEQ ID NO 60
<211> LENGTH: 12
<212> TYPE: PRT
<213> ORGANISM: Artificial Sequence
<220> FEATURE:
<223> OTHER INFORMATION: A synthetic peptide

<400> SEQUENCE: 60

Thr Gly Gly Cys Gly Asn Asn Val Ala Asp Glu Gly
1               5                   10

<210> SEQ ID NO 61
<211> LENGTH: 14
<212> TYPE: PRT
<213> ORGANISM: Artificial Sequence
<220> FEATURE:
<223> OTHER INFORMATION: A synthetic peptide

<400> SEQUENCE: 61

Thr Gly Thr Ser Ala Asn Asn Ile Met Thr Asn Lys Ser Arg
1               5                   10

<210> SEQ ID NO 62
<211> LENGTH: 8
<212> TYPE: PRT
<213> ORGANISM: Artificial Sequence
<220> FEATURE:
<223> OTHER INFORMATION: A synthetic peptide

<400> SEQUENCE: 62

Thr Gly Gly Cys Gly Cys Asn Ala
1               5

<210> SEQ ID NO 63
<211> LENGTH: 14
<212> TYPE: PRT
<213> ORGANISM: Artificial Sequence
<220> FEATURE:
<223> OTHER INFORMATION: A synthetic peptide

<400> SEQUENCE: 63

Thr Ala Thr Tyr Ala Asn Asn Ile Met Thr Asn Lys Ser Arg
1               5                   10

<210> SEQ ID NO 64
<211> LENGTH: 13
<212> TYPE: PRT
<213> ORGANISM: Artificial Sequence
<220> FEATURE:
<223> OTHER INFORMATION: A synthetic peptide

<400> SEQUENCE: 64

Thr Cys Cys Ser Thr Asn Asn Phe Leu Ser Tyr Cys Trp
1               5                   10
```

```
<210> SEQ ID NO 65
<211> LENGTH: 12
<212> TYPE: PRT
<213> ORGANISM: Artificial Sequence
<220> FEATURE:
<223> OTHER INFORMATION: A synthetic peptide

<400> SEQUENCE: 65

Thr Thr Ala Leu Cys Asn Asn Leu Pro His Gln Arg
1               5                   10

<210> SEQ ID NO 66
<211> LENGTH: 13
<212> TYPE: PRT
<213> ORGANISM: Artificial Sequence
<220> FEATURE:
<223> OTHER INFORMATION: A synthetic peptide

<400> SEQUENCE: 66

Thr Asn Asn Phe Leu Ser Tyr Cys Trp Thr Thr Cys Phe
1               5                   10

<210> SEQ ID NO 67
<211> LENGTH: 12
<212> TYPE: PRT
<213> ORGANISM: Artificial Sequence
<220> FEATURE:
<223> OTHER INFORMATION: A synthetic peptide

<400> SEQUENCE: 67

Thr Gly Thr Ser Cys Asn Asn Leu Pro His Gln Arg
1               5                   10

<210> SEQ ID NO 68
<211> LENGTH: 14
<212> TYPE: PRT
<213> ORGANISM: Artificial Sequence
<220> FEATURE:
<223> OTHER INFORMATION: A synthetic peptide

<400> SEQUENCE: 68

Thr Thr Ala Leu Ala Asn Asn Ile Met Thr Asn Lys Ser Arg
1               5                   10

<210> SEQ ID NO 69
<211> LENGTH: 17
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (14)..(14)
<223> OTHER INFORMATION: n is a, c, g, or t

<400> SEQUENCE: 69
aaggagcgat cgcnatg                                                  17

<210> SEQ ID NO 70
<211> LENGTH: 15
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(3)
<223> OTHER INFORMATION: n is a, c, g, or t
```

```
<400> SEQUENCE: 70
nnngcgatcg ccatg                                                   15

<210> SEQ ID NO 71
<211> LENGTH: 12
<212> TYPE: DNA
<213> ORGANISM: Artificial Sequence
<220> FEATURE:
<223> OTHER INFORMATION: A synthetic DNA fragment, wherein the
      complement to the remainder of an open reading frame is present 5'
      to nnn
<220> FEATURE:
<221> NAME/KEY: misc_feature
<222> LOCATION: (1)..(3)
<223> OTHER INFORMATION: n is a, c, g, or t

<400> SEQUENCE: 71
nnncatggcg at                                                      12

<210> SEQ ID NO 72
<211> LENGTH: 12
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(12)
<223> OTHER INFORMATION: n is a, c, g, or t

<400> SEQUENCE: 72 nnngttttnnn nn                                                     12

<210> SEQ ID NO 73
<211> LENGTH: 18
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (6)..(18)
<223> OTHER INFORMATION: n is a, c, g, or t

<400> SEQUENCE: 73
ggatgnnnnn nnnnnnnn                                                18

<210> SEQ ID NO 74
<211> LENGTH: 18
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(13)
<223> OTHER INFORMATION: n is a, c, g, or t

<400> SEQUENCE: 74
nnnnnnnnnn nnncatcc                                                18

<210> SEQ ID NO 75
<211> LENGTH: 15
<212> TYPE: DNA
<213> ORGANISM: Artificial Sequence
<220> FEATURE:
```

```
<223> OTHER INFORMATION: A synthetic DNA fragment
<220> FEATURE:
<221> NAME/KEY: misc_feature
<222> LOCATION: (8)..(15)
<223> OTHER INFORMATION: n is a, c, g, or t

<400> SEQUENCE: 75
cacctgcnnn nnnnn                                                          15

<210> SEQ ID NO 76
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (8)..(11)
<223> OTHER INFORMATION: n is a, c, g, or t

<400> SEQUENCE: 76
gctcttcnnn n                                                              11

<210> SEQ ID NO 77
<211> LENGTH: 13
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (5)..(9)
<223> OTHER INFORMATION: n is a, c, g, or t

<400> SEQUENCE: 77
ggccnnnnng gcc                                                            13

<210> SEQ ID NO 78
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (8)..(11)
<223> OTHER INFORMATION: n is a, c, g, or t

<400> SEQUENCE: 78
gctcttcnnn n                                                              11

<210> SEQ ID NO 79
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (3)..(9)
<223> OTHER INFORMATION: n is a, c, g, or t

<400> SEQUENCE: 79
ccnnnnnnng g                                                              11

<210> SEQ ID NO 80
<211> LENGTH: 13
<212> TYPE: DNA
<213> ORGANISM: Artificial Sequence
<220> FEATURE:
```

```
<223> OTHER INFORMATION: A synthetic DNA fragment
<220> FEATURE:
<221> NAME/KEY: misc_feature
<222> LOCATION: (5)..(9)
<223> OTHER INFORMATION: n is a, c, g, or t

<400> SEQUENCE: 80
ggccnnnnng gcc                                                              13

<210> SEQ ID NO 81
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(8)
<223> OTHER INFORMATION: n is a, c, g, or t

<400> SEQUENCE: 81
gcannnnntg c                                                                11

<210> SEQ ID NO 82
<211> LENGTH: 18
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (7)..(18)
<223> OTHER INFORMATION: n is a, c, g, or t

<400> SEQUENCE: 82
cccacannnn nnnnnnnn                                                         18

<210> SEQ ID NO 83
<211> LENGTH: 19
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(1)
<223> OTHER INFORMATION: v = A, G, or C

<400> SEQUENCE: 83
vaaggagcga tcgccatgg                                                        19

<210> SEQ ID NO 84
<211> LENGTH: 18
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(1)
<223> OTHER INFORMATION: v = A, G, or C

<400> SEQUENCE: 84
vaaggagcga tcgccatg                                                         18

<210> SEQ ID NO 85
<211> LENGTH: 6
<212> TYPE: PRT
<213> ORGANISM: Artificial Sequence
<220> FEATURE:
```

```
<223> OTHER INFORMATION: A synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 85

Xaa Gly Ala Ile Ala Met
1               5

<210> SEQ ID NO 86
<211> LENGTH: 12
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 86
nnngtttaaa cn                                                         12

<210> SEQ ID NO 87
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 87
nnngtttatc n                                                          11

<210> SEQ ID NO 88
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 88
nnngtttcca n                                                          11

<210> SEQ ID NO 89
<211> LENGTH: 19
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
```

```
<222> LOCATION: (1)..(1)
<223> OTHER INFORMATION: v = A, G, or C

<400> SEQUENCE: 89
vaaggattaa tcgccatgg                                                      19

<210> SEQ ID NO 90
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 90

Xaa Gly Leu Ile Ala Met
1               5

<210> SEQ ID NO 91
<211> LENGTH: 12
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 91
nnngtttaaa tn                                                             12

<210> SEQ ID NO 92
<211> LENGTH: 13
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (9)..(9)
<223> OTHER INFORMATION: n is a, c, g, or t

<400> SEQUENCE: 92
gcgatcgcna tgg                                                            13

<210> SEQ ID NO 93
<211> LENGTH: 12
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (9)..(9)
<223> OTHER INFORMATION: n is a, c, g, or t

<400> SEQUENCE: 93
gcgatcgcna tg                                                             12

<210> SEQ ID NO 94
<211> LENGTH: 11
<212> TYPE: DNA
```

```
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (8)..(11)
<223> OTHER INFORMATION: n is a, c, g, or t

<400> SEQUENCE: 94
gctcttcnnn n                                                    11

<210> SEQ ID NO 95
<211> LENGTH: 11
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(8)
<223> OTHER INFORMATION: n is a, c, g, or t

<400> SEQUENCE: 95 gccnnnnnngg c                                                   11

<210> SEQ ID NO 96
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (7)..(10)
<223> OTHER INFORMATION: n is a, c, g, or t

<400> SEQUENCE: 96 ctcttcnnnn                                                      10

<210> SEQ ID NO 97
<211> LENGTH: 10
<212> TYPE: DNA
<213> ORGANISM: Artificial Sequence
<220> FEATURE:
<223> OTHER INFORMATION: A synthetic DNA fragment
<220> FEATURE:
<221> NAME/KEY: misc_feature
<222> LOCATION: (4)..(7)
<223> OTHER INFORMATION: n is a, c, g, or t

<400> SEQUENCE: 97 cacnnnngtg                                                      10
```

What is claimed is:

1. A vector encoding a fusion polypeptide prepared by ligating a DNA fragment comprising a first opening reading frame, a 5' end generated after cleavage of a first recognition site with a first restriction enzyme which generates an end compatible with an end generated after cleavage of a SgfI recognition site by SgfI, and a 3' end generated after cleavage of a second recognition site for a second restriction enzyme which generates a blunt end, and a DNA segment comprising a second open reading frame that begins with an ATG but does not end with an in-frame stop codon, a 3' end generated after cleavage of a third recognition site with a third restriction enzyme which generates an end compatible with an end generated after cleavage of a SgfI recognition site by SgfI, and a 5' end generated after cleavage of a PmeI site with PmeI, wherein the first restriction enzyme is SgfI, the third restriction enzyme is SgfI, or both the first and third restriction enzymes are SgfI, wherein ligation of the blunt end and the 5' end generated after cleavage of the PmeI site provides an in-frame TAA stop codon for the first open reading frame, and wherein ligation of the SgfI compatible ends yields a third open reading frame comprising the first and second open reading frames which encodes the fusion polypeptide.

2. The vector of claim 1 wherein the DNA segment further comprises a promoter 5' to the ATG of the second open reading frame.

3. The vector of claim 1 wherein the first and third recognition sites are cleaved by SgfI and yield an exchange site comprising GCGATCGCnATGG (SEQ ID NO: 92), wherein n is C, A, T or G.

4. The vector of claim 3 wherein n is C.

5. The vector of claim 1 wherein the first and third recognition sites are cleaved by SgfI and yield an exchange site comprising GCGATCGCnATG (SEQ ID NO: 93), wherein n is C, A, T or G.

6. The vector of claim 1 wherein the first and third recognition sites are cleaved by SgfI and yield an exchange site comprising GCGATCGCnATG (SEQ ID NO: 93), wherein n is C.

7. The vector of claim 1, wherein the first open reading frame does not begin with ATG.

* * * * *